(12) United States Patent
Bellamine et al.

(10) Patent No.: US 10,888,571 B2
(45) Date of Patent: Jan. 12, 2021

(54) METHOD AND COMPOSITION FOR INCREASING MUSCLE PROTEIN SYNTHESIS AND/OR FUNCTIONAL STRENGTH IN MAMMALS

(71) Applicant: Lonza Consumer Health Inc., Morristown, NJ (US)

(72) Inventors: Aouatef Bellamine, Pennington, NJ (US); Ilya Zhivkovich, Milford, PA (US); Ulla Freitas, Lorrach (DE)

(73) Assignee: Lonza Consumer Health Inc., Morristown, NJ (US)

(*) Notice: Subject to any disclaimer, the term of this patent is extended or adjusted under 35 U.S.C. 154(b) by 16 days.

(21) Appl. No.: 15/381,731

(22) Filed: Dec. 16, 2016

(65) Prior Publication Data
US 2017/0173050 A1    Jun. 22, 2017

Related U.S. Application Data

(60) Provisional application No. 62/273,880, filed on Dec. 31, 2015, provisional application No. 62/269,573, filed on Dec. 18, 2015.

(51) Int. Cl.

| | | |
|---|---|---|
| *A23K 20/174* | (2016.01) | |
| *A23K 20/142* | (2016.01) | |
| *A23L 33/15* | (2016.01) | |
| *A23L 33/16* | (2016.01) | |
| *A23L 33/17* | (2016.01) | |
| *A23L 2/66* | (2006.01) | |
| *A61K 9/00* | (2006.01) | |
| *A61K 9/16* | (2006.01) | |
| *A61K 9/20* | (2006.01) | |
| *A61K 33/00* | (2006.01) | |
| *A61K 31/198* | (2006.01) | |
| *A61K 31/593* | (2006.01) | |
| *A61K 31/197* | (2006.01) | |
| *A61K 31/205* | (2006.01) | |
| *A61K 45/06* | (2006.01) | |
| *A61P 21/00* | (2006.01) | |
| *A23K 20/20* | (2016.01) | |
| *A23C 9/152* | (2006.01) | |

(52) U.S. Cl.
CPC .......... *A61K 31/593* (2013.01); *A23K 20/142* (2016.05); *A23K 20/174* (2016.05); *A23K 20/30* (2016.05); *A23L 2/66* (2013.01); *A23L 33/15* (2016.08); *A23L 33/16* (2016.08); *A23L 33/17* (2016.08); *A61K 9/16* (2013.01); *A61K 9/20* (2013.01); *A61K 31/197* (2013.01); *A61K 31/198* (2013.01); *A61K 31/205* (2013.01); *A61K 33/00* (2013.01); *A61K 45/06* (2013.01); *A23C 9/1526* (2013.01); *A23V 2002/00* (2013.01)

(58) Field of Classification Search
CPC ..... A23K 20/174; A23K 20/142; A23L 33/15; A23L 33/16; A23L 33/17; A23L 2/66; A61K 9/00; A61K 9/16; A61K 9/20; A61K 33/00; A61K 31/198; A61K 31/593; A61K 31/197; A61K 31/205; A61K 45/06; A61P 21/00

See application file for complete search history.

(56) References Cited

U.S. PATENT DOCUMENTS

| | | | |
|---|---|---|---|
| 4,687,782 A | 8/1987 | Brantman | |
| 4,883,672 A | 11/1989 | Shug et al. | |
| 6,159,942 A | 12/2000 | St. Cyr et al. | |
| 6,232,346 B1* | 5/2001 | Sole | A61K 31/205 514/561 |
| 6,245,378 B1 | 6/2001 | Cavazza | |
| 6,602,512 B1 | 8/2003 | Cavazza | |
| 7,645,742 B2* | 1/2010 | Stohs | A61K 31/19 424/94.1 |
| 7,790,688 B2 | 9/2010 | Wolfe et al. | |
| 8,029,819 B2 | 10/2011 | Bierer et al. | |
| 8,535,708 B2 | 9/2013 | Wedekind et al. | |
| 8,546,369 B2 | 10/2013 | Heuer et al. | |
| 8,784,844 B2 | 7/2014 | Rodriguez et al. | |
| 2001/0043983 A1 | 11/2001 | Hamilton | |
| 2008/0233245 A1* | 9/2008 | White | A23L 2/39 426/73 |

(Continued)

FOREIGN PATENT DOCUMENTS

| | | | | |
|---|---|---|---|---|
| FR | 2938733 A1 | 5/2010 | | |
| WO | WO-9800148 A1 * | 1/1998 | ............. | A61K 33/32 |

(Continued)

OTHER PUBLICATIONS

Derivative, 2018, https://en.wikipedia.org/wiki/Derivative_(chemistry).*
WO9800148—machine-translation, 2019, machine translation of WO9800148.*
Cruz-Jentoft Alfonso J et al., Sarcopenia: European consensus on definition and diagnosis: Report of the European Working Group on Sarcopenia in Older People, Age and Ageing, Bailliere Tindall, London, US, vol. 39, No. 4, Jul. 1, 2010, pp. 412-423.
PCT/US2016/067238 International Search Report and Written Opinion, dated Mar. 17, 2017, 19 pages.
Jeff S. Volek, et al., L-Carnitine L-tartrate supplementation favorably affects markers of recovery from exercise stress, American Journal of Physiology: Endocrinology and Metabolism, American Physiological Society, Bethesda, MD., vol. 282, Jan. 1, 2002, pp. E474-E482.

(Continued)

*Primary Examiner* — Sun Jae Yoo
(74) *Attorney, Agent, or Firm* — Dority & Manning, P.A.

(57) ABSTRACT

A method and composition for preserving muscle mass and function by increasing muscle protein synthesis and/or decreasing muscle protein degradation in mammals is disclosed. In one embodiment, the mammals are administered a protein building composition comprising at least two of an essential amino acid, an amino acid derivative, and a nitrogenous organic acid. In a particular embodiment, the protein building composition comprises leucine, L-carnitine, and creatine. The protein building composition can decrease TNF-α and increase mTOR expression in muscle.

27 Claims, 16 Drawing Sheets

(56) References Cited

U.S. PATENT DOCUMENTS

| | | | |
|---|---|---|---|
| 2009/0181903 A1* | 7/2009 | Wolfe | A61K 31/198 514/23 |
| 2014/0193370 A1 | 7/2014 | Tissot-Favre et al. | |
| 2015/0359769 A1 | 12/2015 | Lopez et al. | |
| 2015/0368192 A1 | 12/2015 | Millo et al. | |

FOREIGN PATENT DOCUMENTS

| WO | WO2008/115563 A1 | 9/2008 |
|---|---|---|
| WO | WO2015/094772 A1 | 6/2015 |

OTHER PUBLICATIONS

Khadijeh Parandak, et al., The Effect of Two-Week L-Carnitine Supplementation on Exercise-Induced Oxidative Stress and Muscle Damage, Asian J Sports Medicine Asian Journal of Sports Medicine, vol. 5 (No. 2) Tehran, Iran, Mar. 1, 2014, pp. 123-128.

William J. Kraemer, et al., L-Carnitine Supplementation: Influence upon Physiological Function, Human performance Labooratory, Department of Kinesiology, Department of Physiology and Neurobilogy, Current Sports Medicine Report, 2008, vol. 7, No. 4, pp. 218-223.

Amy Huang et al., Role of Supplementary L-Carnitine in Exercise and Exercise Recovery, Lamprecht M (ed) Acute Topics in sport Nutrition, Medical Sports Science Basel, Karger, 2013, vol. 59. pp. 135-142.

William J. Kraemer, et al., The Effects of L-Carnitine L-Tartrate Supplementation on Hormonal Responses to Resistance Exercise and Recovery, Journal of Strength and Conditioning Research, 2003, vol. 17, No. 3, pp. 455-462.

William J. Kraemer, et al. ,L-Carnitine Supplementation: A New Paradigm for its Role in Exercise, Monatshefte fur Chemie Chemical Monthly, Published online Jun. 10, 2005, pp. 1383-1390.

Jen-Yu Ho, et al., L-Carnitine L-tartrate supplementation favorably affects biochemical markers of recovery from physical exertion in middle aged men and women, Science Direct, Metabolism Clinical and Experimental 59 (2010) pp. 1190-1199.

William J. Kraemer,et al., Androgenic Responses to Resistance Exercise: Effects of Feeding and L-Carnitine, Medicine & Science in Sports & Exercise, 2006, vol. 38, No. 7, pp. 1288-1296.

Martyn R. Rubin, et al. Safety Measures of L-Carnitine L-Tartrate Supplementation in Healthy Men, Journal of Strength and Conditioning Research, 2001, vol. 15, No, 4 pp. 486-490.

Barry A. Spiering, et al., Effects of L-Carnitine L-Tartrate Supplementation on Muscle Oxygenation Responses to Resistance Exercise, Journal of Strength and Conditioning Research vol. 22, No. 4, Jul. 2008, pp. 11330-1135.

Barry A. Spiering, et al. Responses of Criterion Variables to Different Supplemental Doses of L-Carnitine L-Tartrate, Journal of Strength and Conditioning Research, 2007, vol. 21, No. 1, pp. 259-264.

Jeff S. Volek, et. al., Effects of Carnitine Supplementation on Flow-Mediated Dilation and Vascular Inflammatory Responses to a High Fat Meal in Healthy Young Adults, The American Journal of Cardiology 2008, V01. 102, pp. 1413-1417.

* cited by examiner

The Change in Absolute Total Lean Mass from Baseline to Week 8 for Participants Supplemented with either Placebo, Carnipure product 1, or Carnipure product 2 in the PP Population (N = 39).
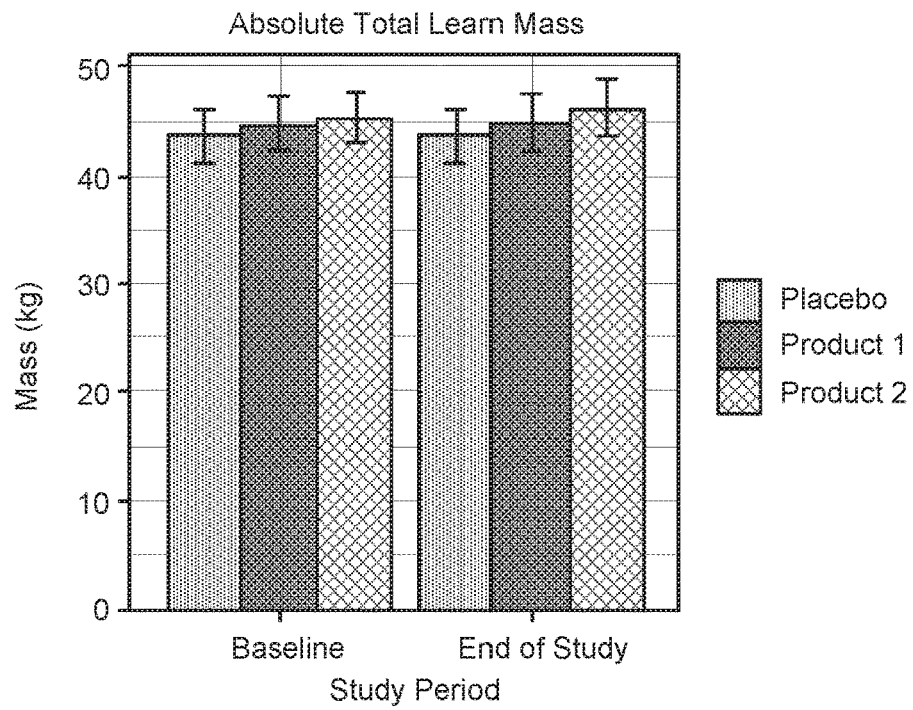
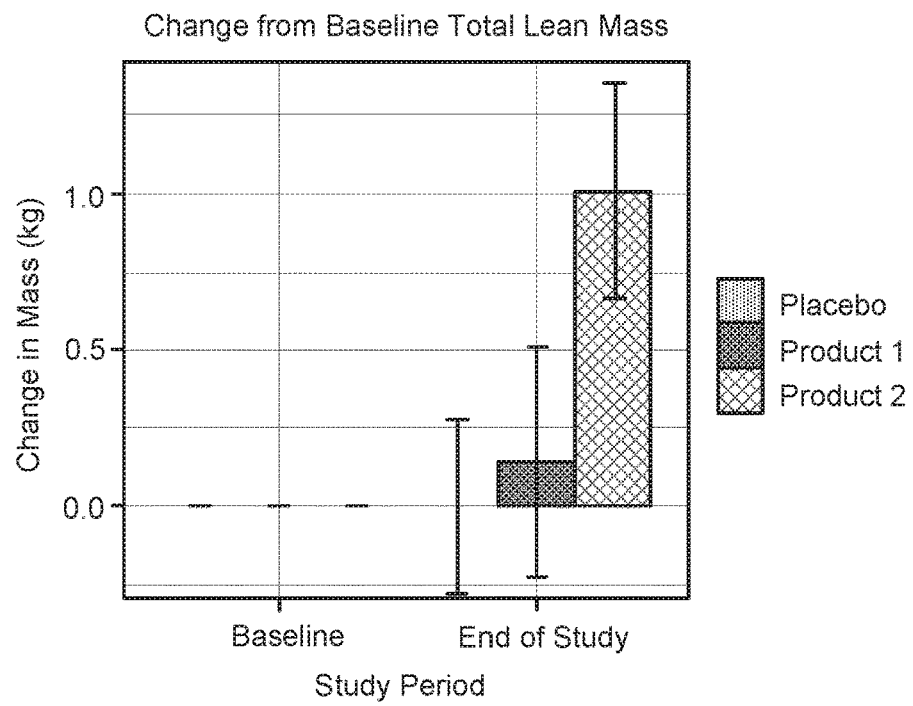
FIG. 1

The Change in Leg Lean Mass from Baseline to Week 8 for Participants Supplemented with either Placebo, Carnipure product 1, or Carnipure product 2 in the PP Population (N = 39).
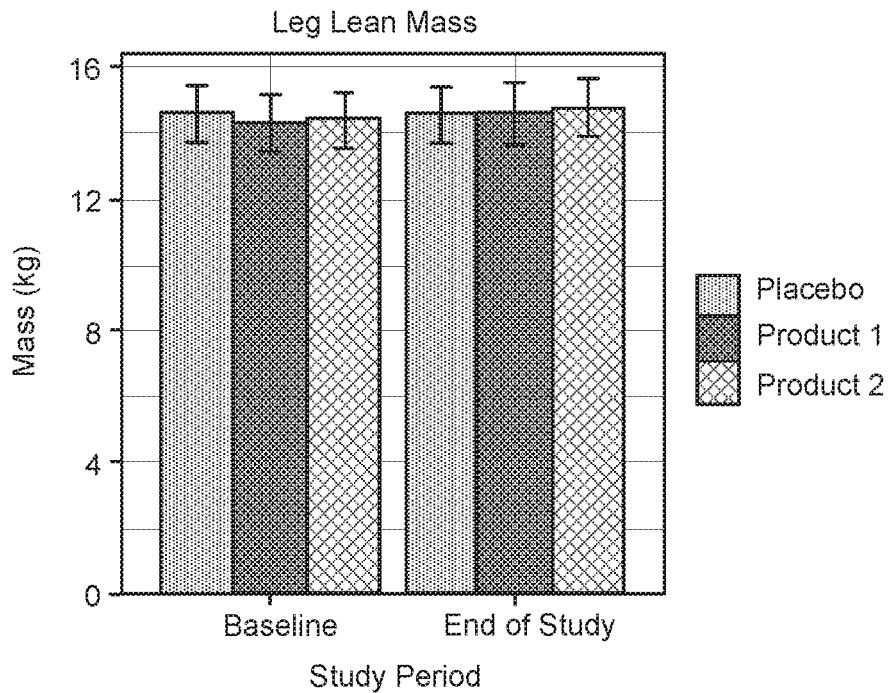
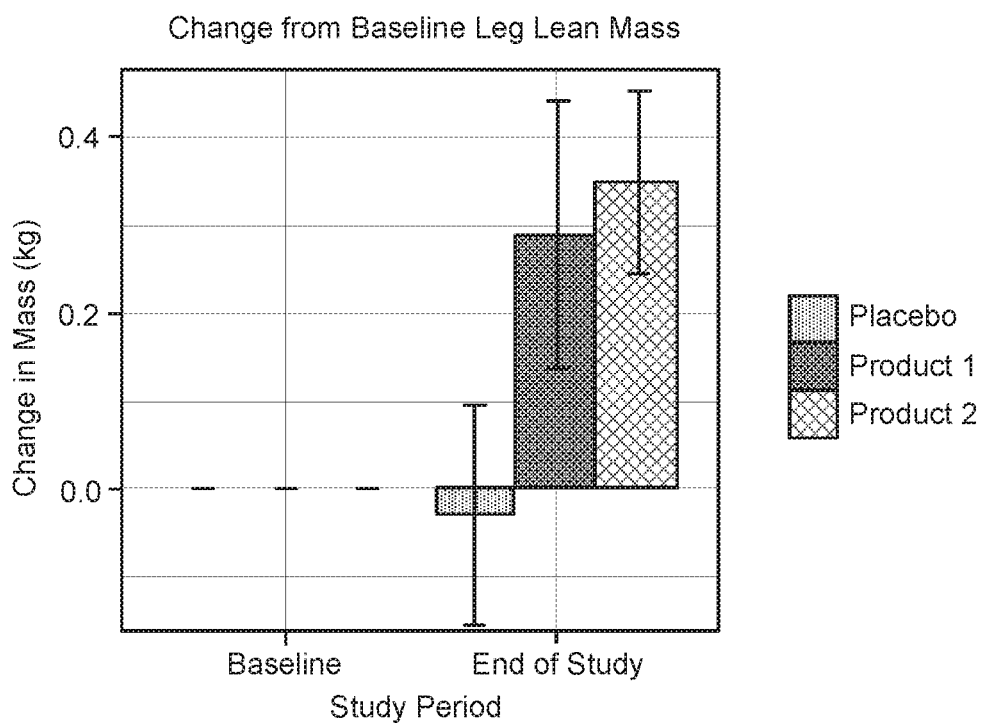
FIG. 3

The Change in Total Non-Trunk Lean Mass from Baseline to Week 8 for Participants Supplemented with either Placebo, Carnipure product 1, or Carnipure product 2 in the PP Population (N = 39).
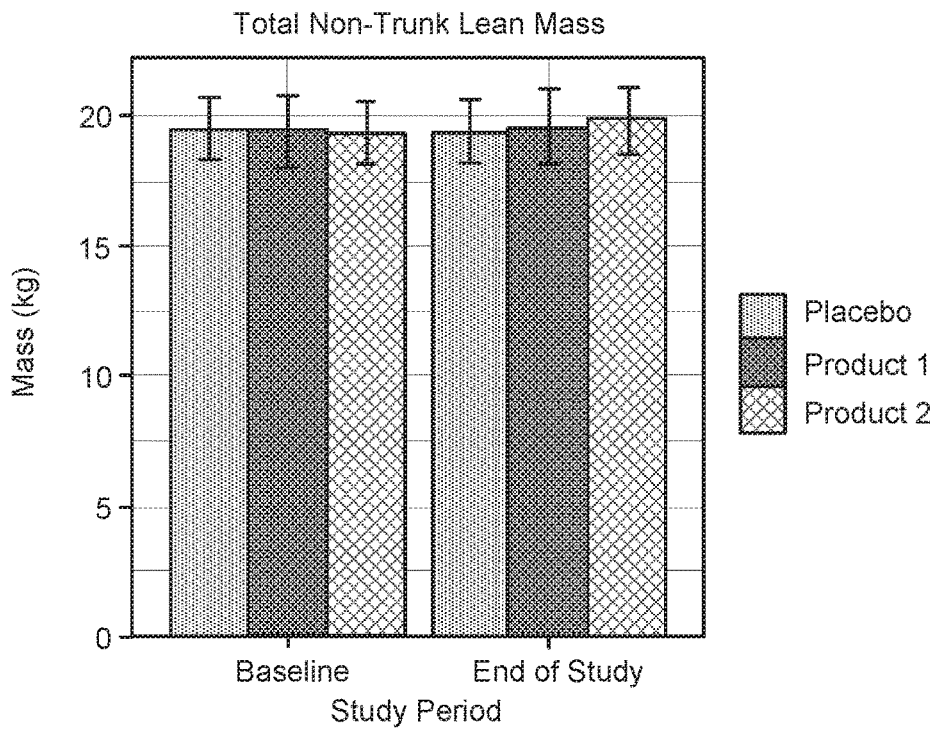
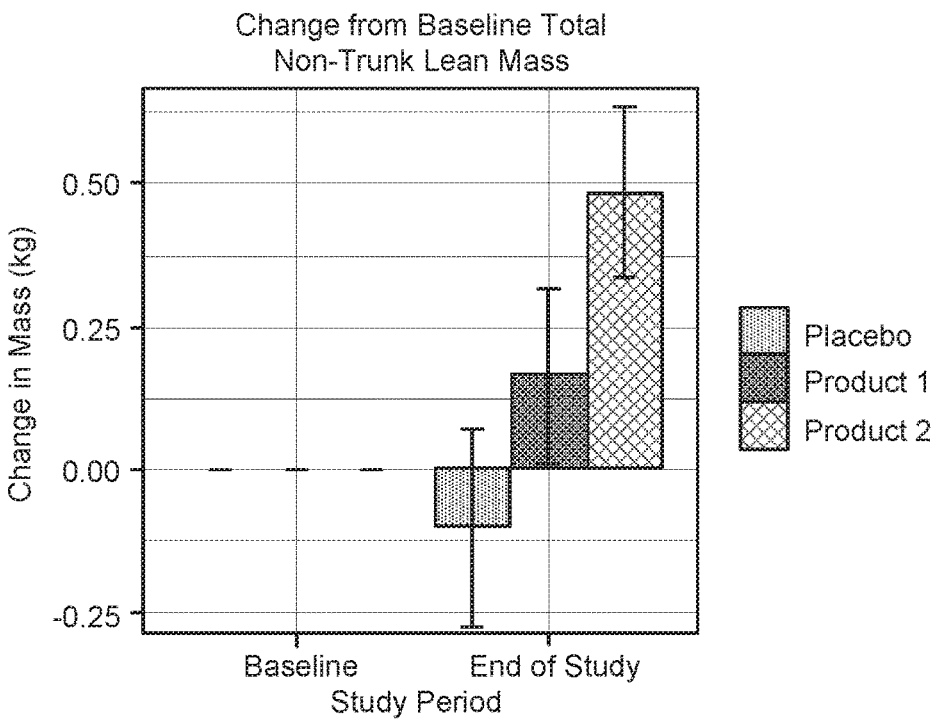
FIG. 4

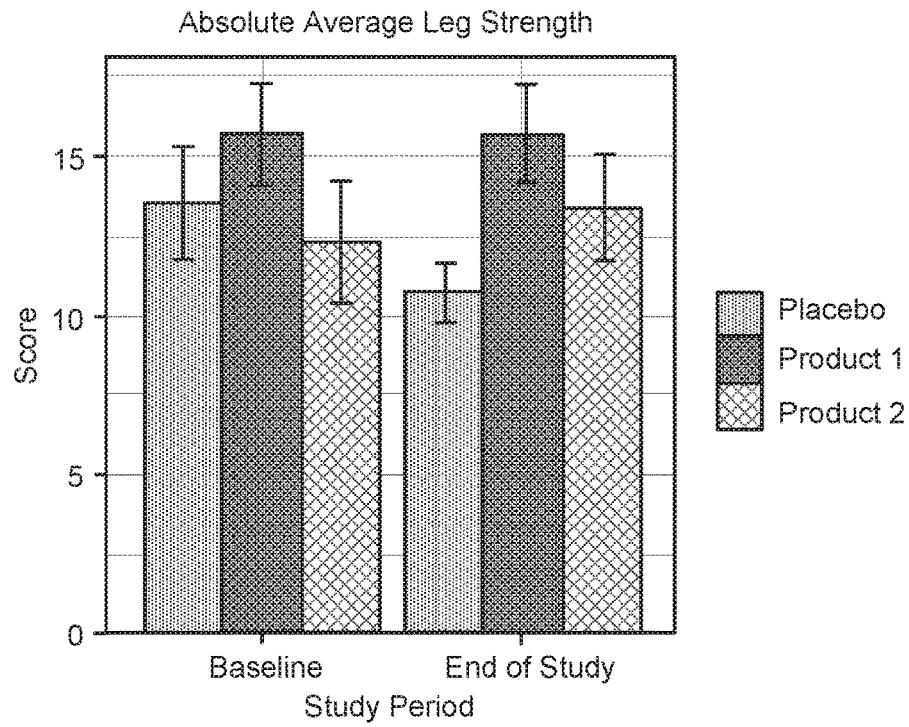
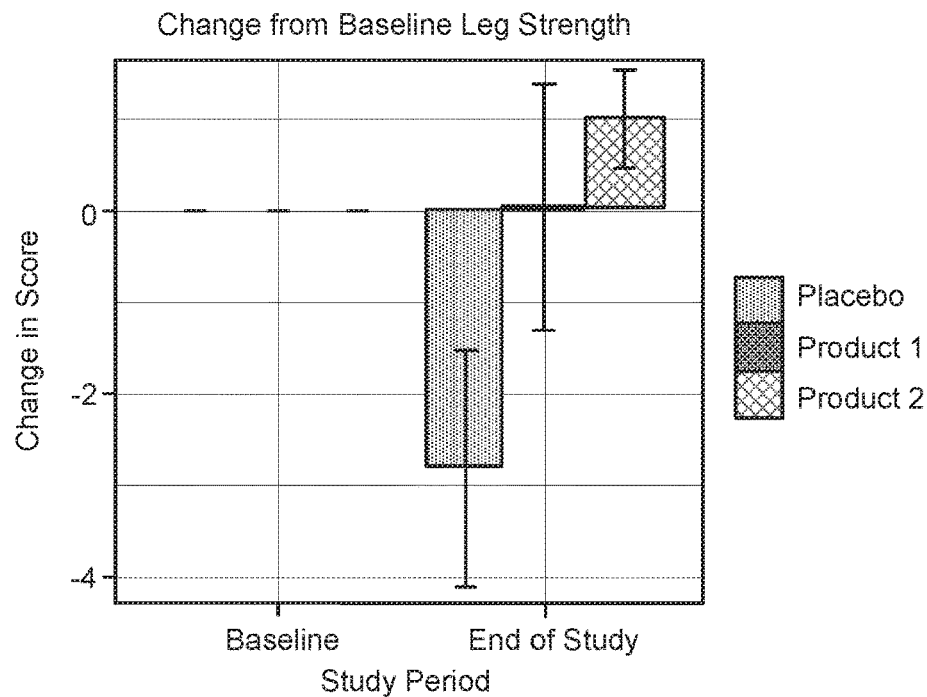
FIG. 5

The AUC per µg of protein for Phospho-mTOR from Baseline to Week 8 Pre and Post Exercise for Participants Supplemented with either Placebo, Carnipure product 1, or Carnipure product 2 in the PP Population (N = 33).

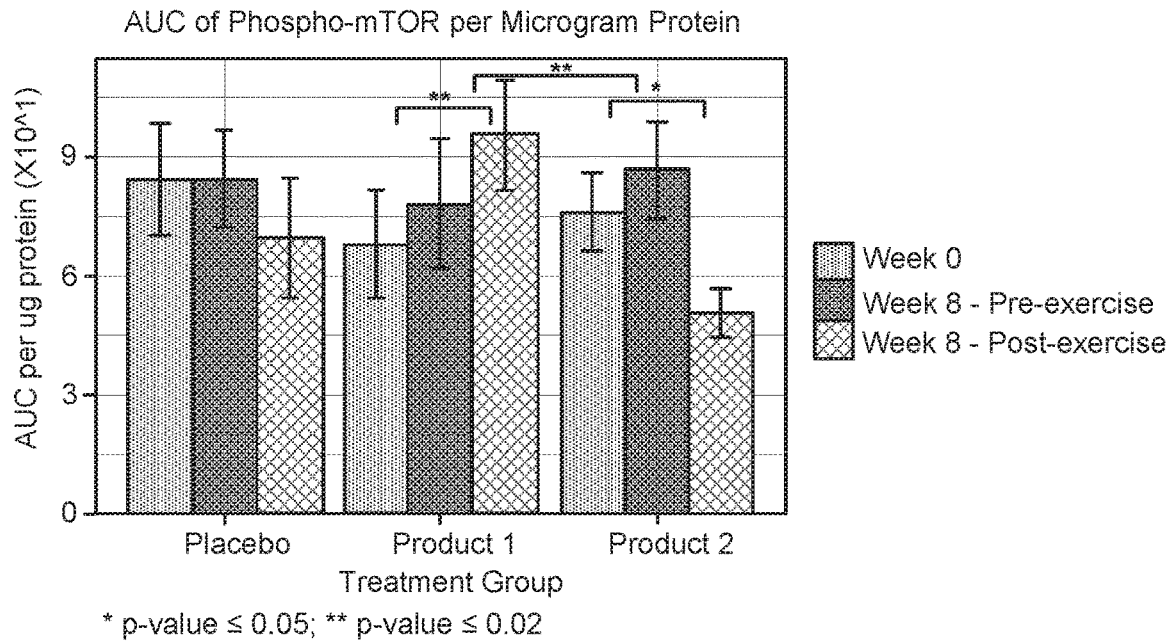

* p-value ≤ 0.05; ** p-value ≤ 0.02

FIG. 6

The Change in Phospho-mTOR from Baseline to Week 8 Pre and Post Exercise for Participants Supplemented with either Placebo, Carnipure product 1, or Carnipure product 2 in the PP Population (N = 33).

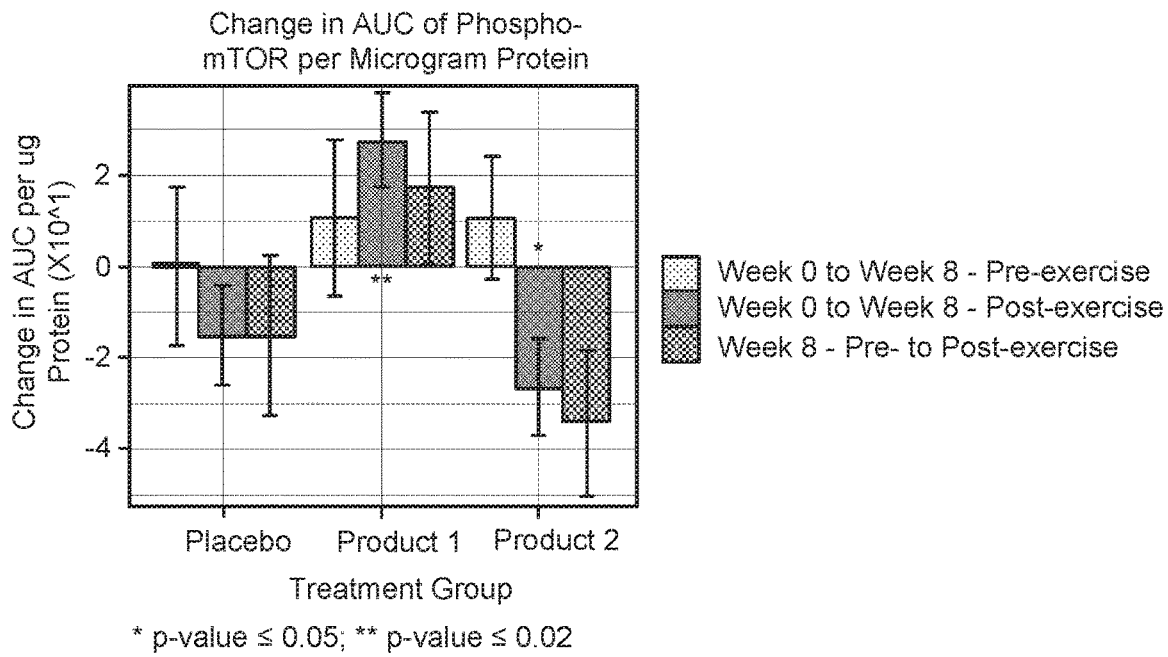

* p-value ≤ 0.05; ** p-value ≤ 0.02

FIG. 7

The AUC per µg of protein for Total-mTOR from Baseline to Week 8 Pre and Post Exercise for Participants Supplemented with either Placebo, Carnipure product 1, or Carnipure product 2 in the PP Population (N = 33).

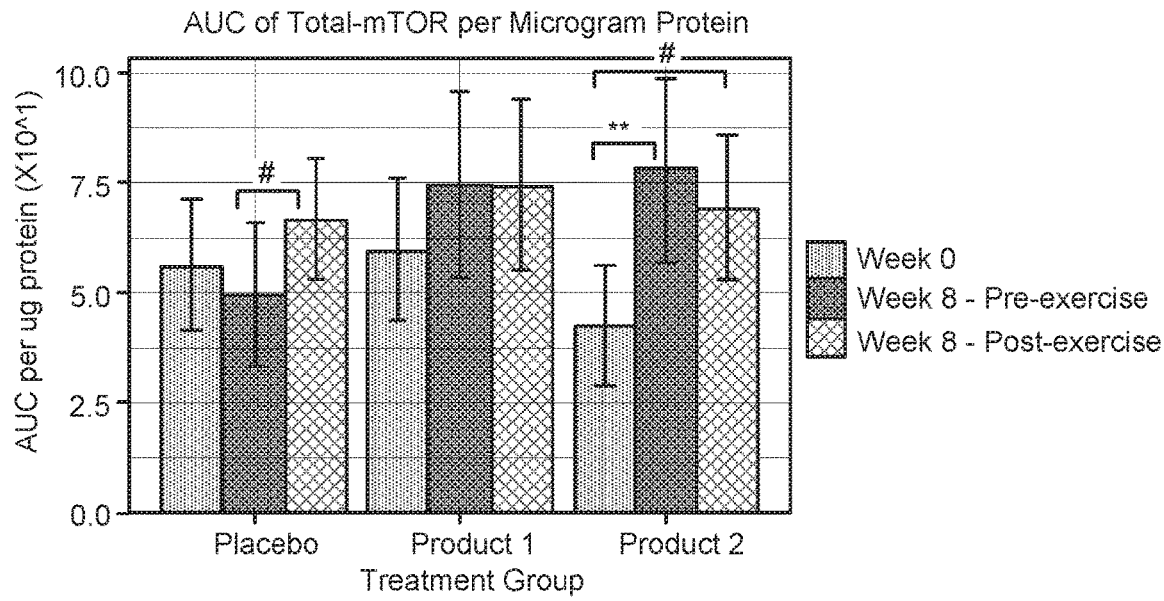

p-value ≤ 0.10; * p-value ≤ 0.05; ** p-value ≤ 0.02

FIG. 8

The Change in Total-mTOR from Baseline to Week 8 Pre and Post Exercise for Participants Supplemented with either Placebo, Carnipure product 1, or Carnipure product 2 in the PP Population (N = 33).

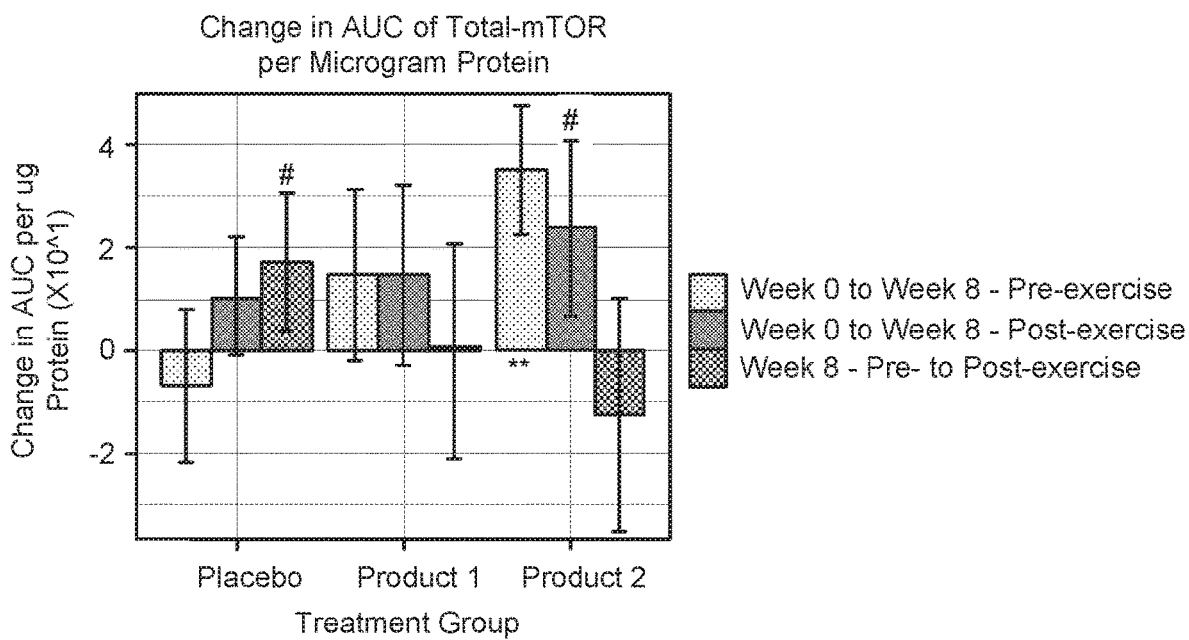

p-value ≤ 0.10; * p-value ≤ 0.05; ** p-value ≤ 0.02

FIG. 9

The AUC per μg of protein for Phospho-S6K from Baseline to Week 8 Pre and Post Exercise for Participants Supplemented with either Placebo, Carnipure product 1, or Carnipure product 2 in the PP Population (N = 33).

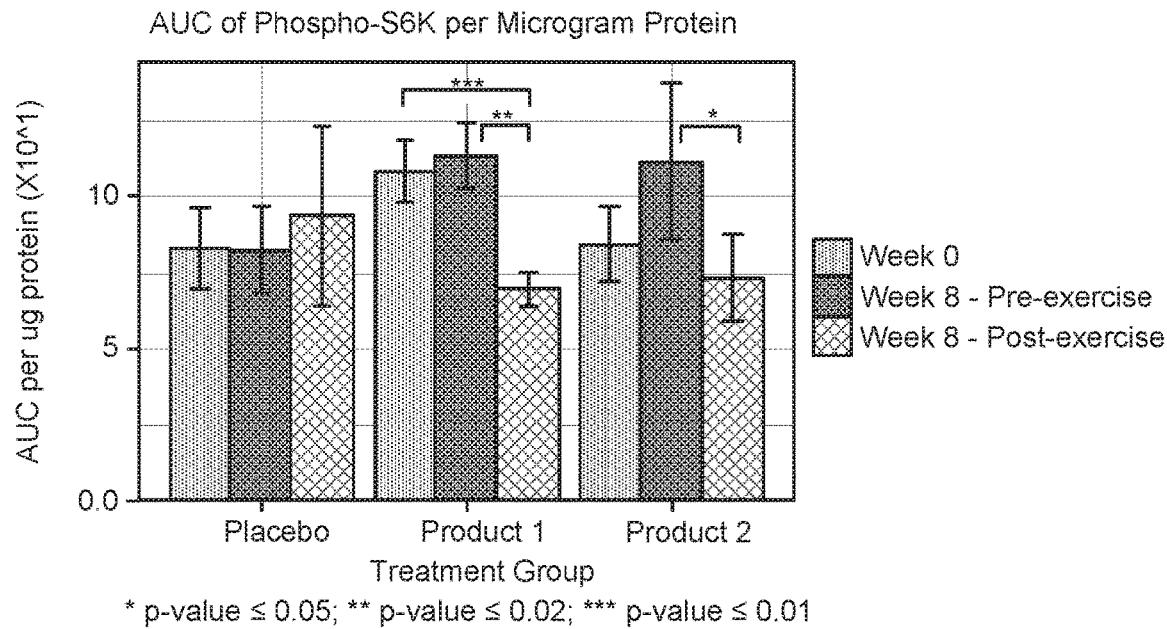

FIG. 10

The Change in Phospho-S6K from Baseline to Week 8 Pre and Post Exercise for Participants Supplemented with either Placebo, Carnipure product 1, or Carnipure product 2 in the PP Population (N = 33).

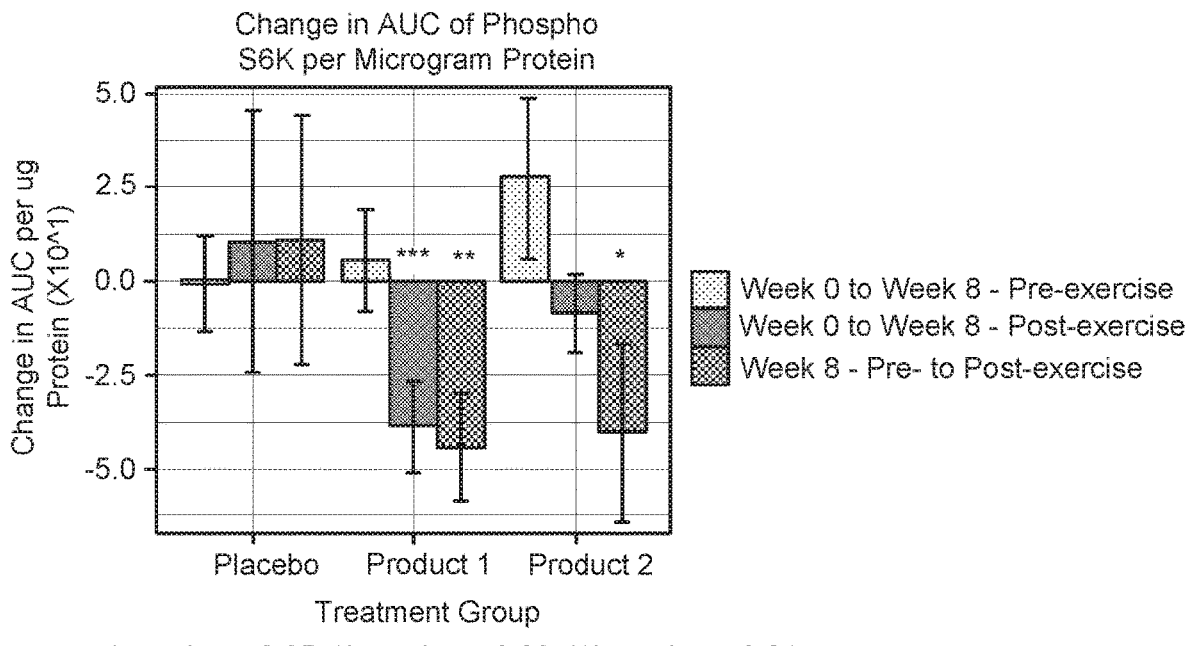

FIG. 11

The AUC per μg of protein for Total-S6K from Baseline to Week 8 Pre and Post Exercise for Participants Supplemented with either Placebo, Carnipure product 1, or Carnipure product 2 in the PP Population (N = 33).

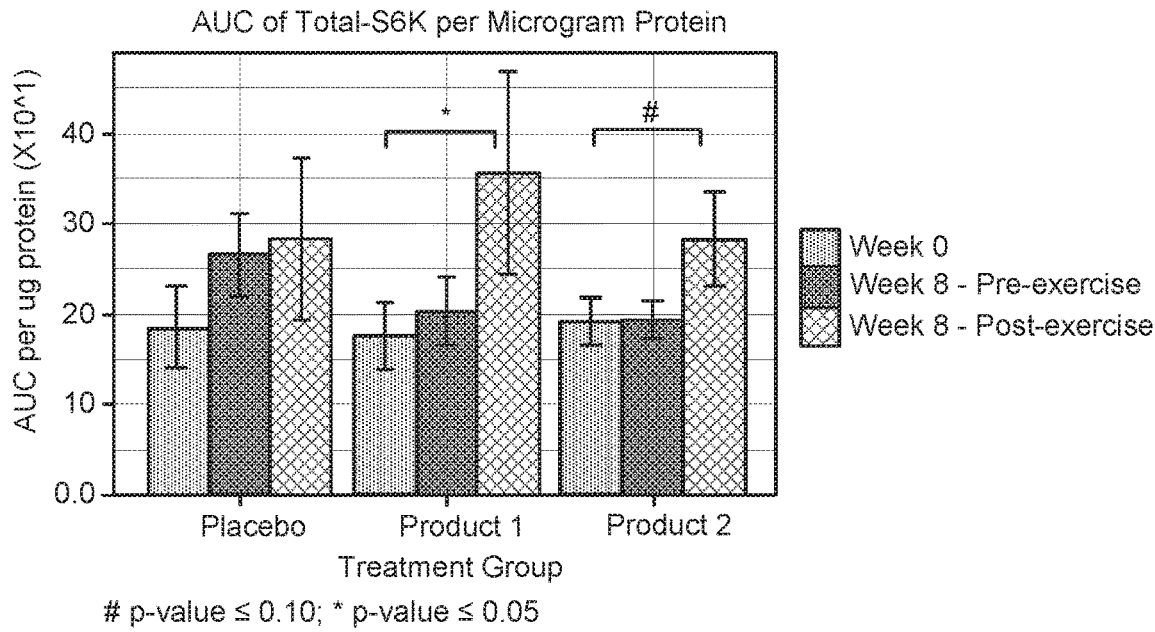

FIG. 12

The Change in Total-S6K from Baseline to Week 8 Pre and Post Exercise for Participants Supplemented with either Placebo, Carnipure product 1, or Carnipure product 2 in the PP Population (N = 33).

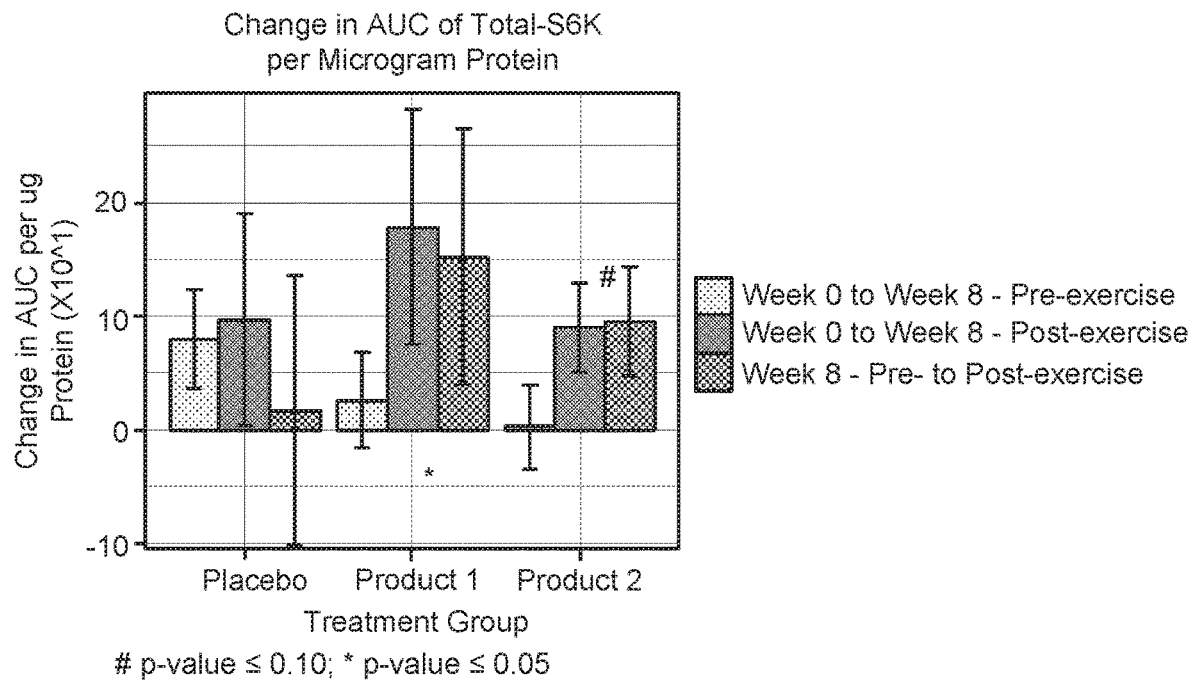

FIG. 13

The AUC per µg of protein for Phospho-4EBP1 from Baseline to Week 8 Pre and Post Exercise for Participants Supplemented with either Placebo, Carnipure product 1, or Carnipure product 2 in the PP Population (N = 33).

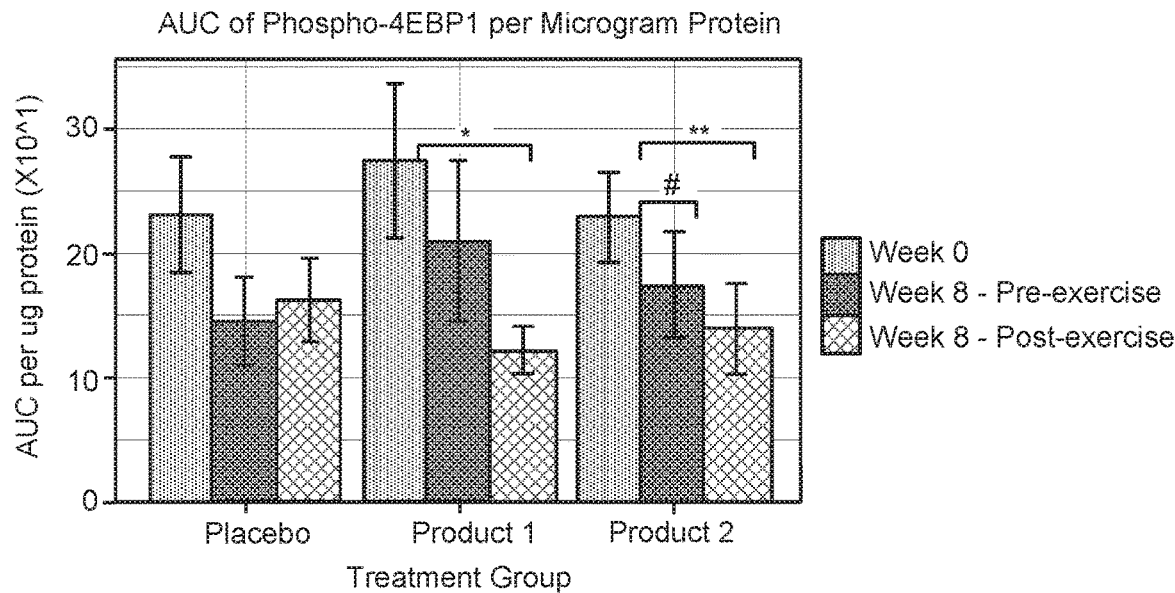

p-value ≤ 0.10; * p-value ≤ 0.05; ** p-value ≤ 0.02

FIG. 14

The Change in Phospho-4EBP1 from Baseline to Week 8 Pre and Post Exercise for Participants Supplemented with either Placebo, Carnipure product 1, or Carnipure product 2 in the PP Population (N = 33).

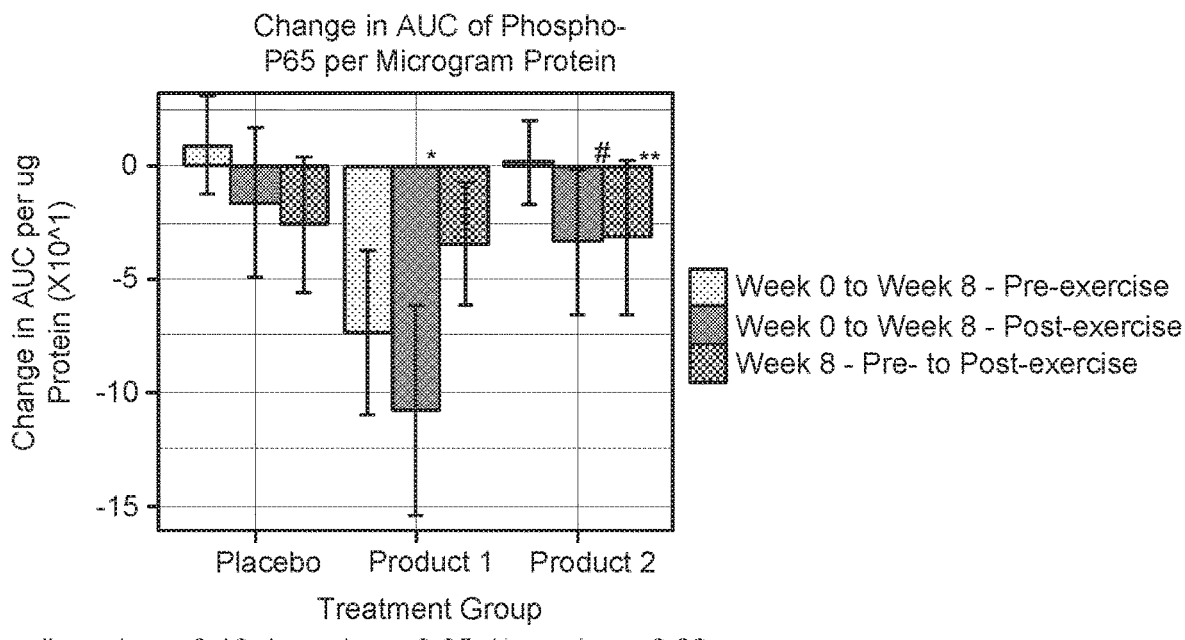

p-value ≤ 0.10; * p-value ≤ 0.05; ** p-value ≤ 0.02

FIG. 15

The AUC per µg of protein for Total-4EBP1 from Baseline to Week 8 Pre and Post Exercise for Participants Supplemented with either Placebo, Carnipure product 1, or Carnipure product 2 in the PP Population (N = 33).

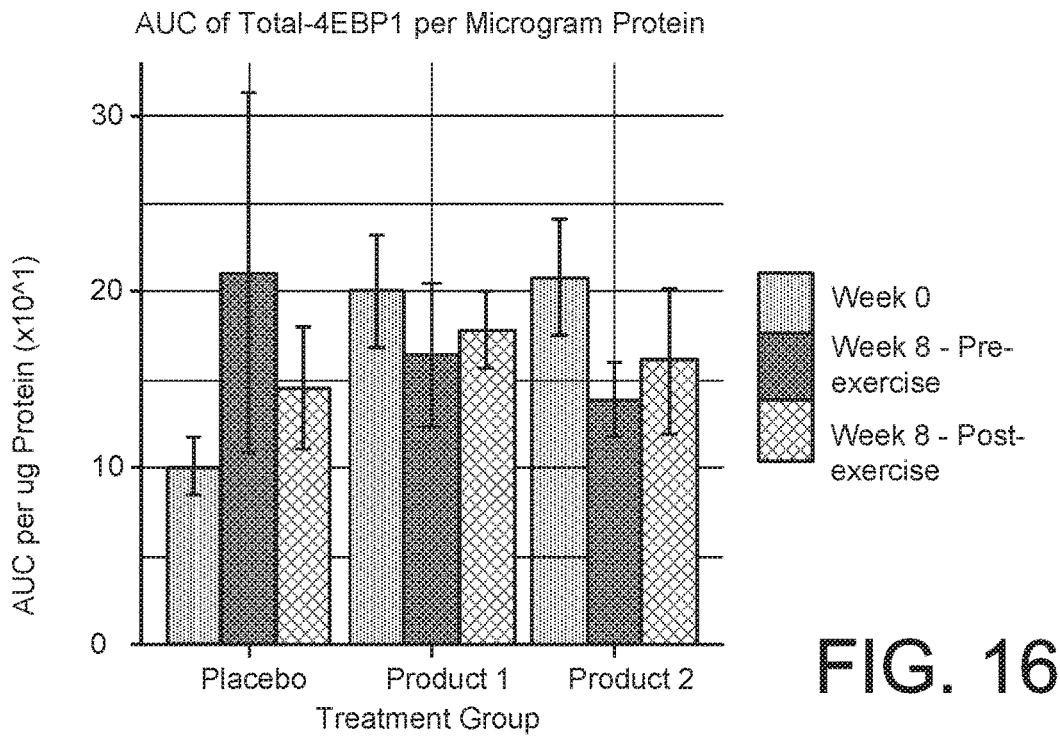

FIG. 16

The Change in Total-4EBP1 from Baseline to Week 8 Pre and Post Exercise for Participants Supplemented with either Placebo, Carnipure product 1, or Carnipure product 2 in the PP Population (N = 33).

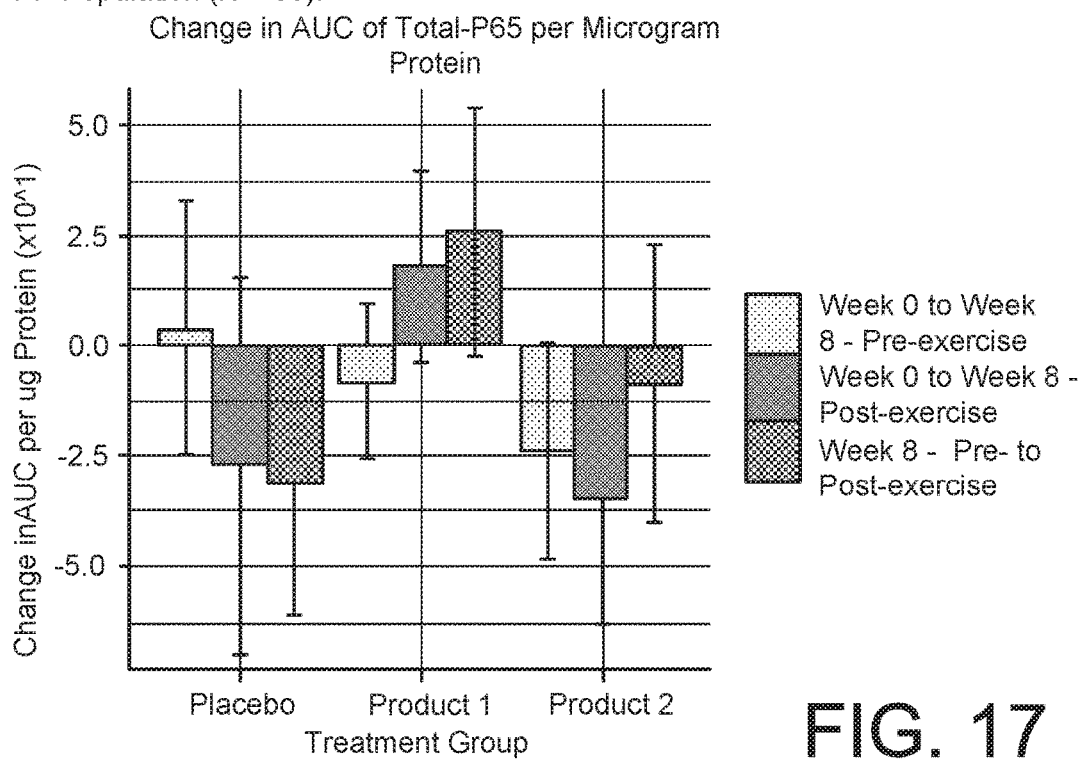

FIG. 17

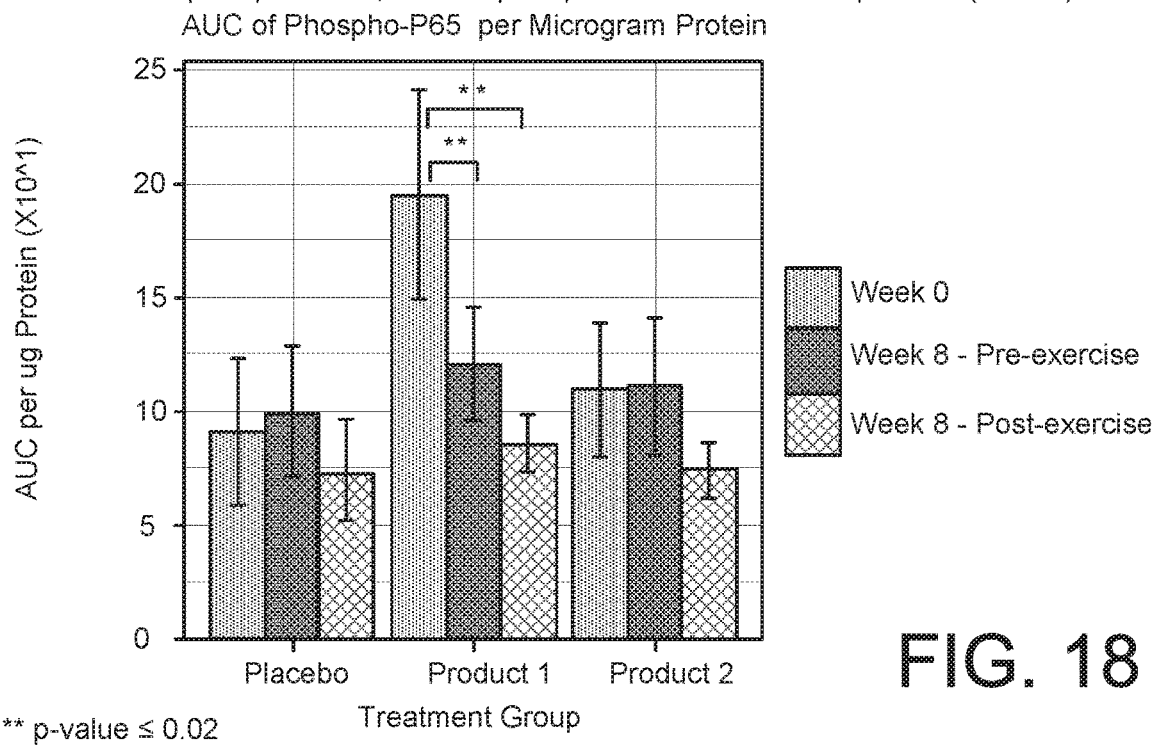

The AUC per μg of protein for Phospho-P65 from Baseline to Week 8 Pre and Post Exercise for Participants Supplemented with either Placebo, Carnipure product 1, or Carnipure product 2 in the PP Population (N = 33).

** p-value ≤ 0.02

FIG. 18

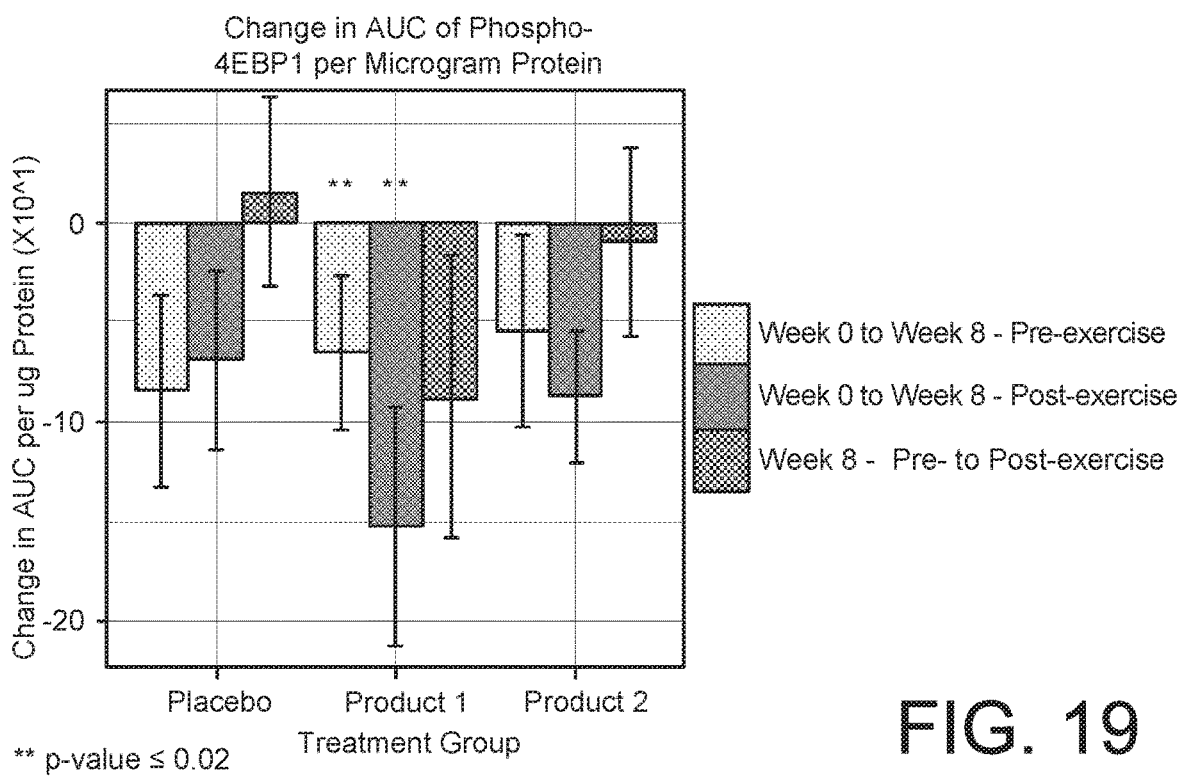

The Change in Phospho-P65 from Baseline to Week 8 Pre and Post Exercise for Participants Supplemented with either Placebo, Carnipure product 1, or Carnipure product 2 in the PP Population (N = 33).

** p-value ≤ 0.02

FIG. 19

The AUC per μg of protein for Total-P65 from Baseline to Week 8 Pre and Post Exercise for Participants Supplemented with either Placebo, Carnipure product 1, or Carnipure product 2 in the PP Population (N = 33).

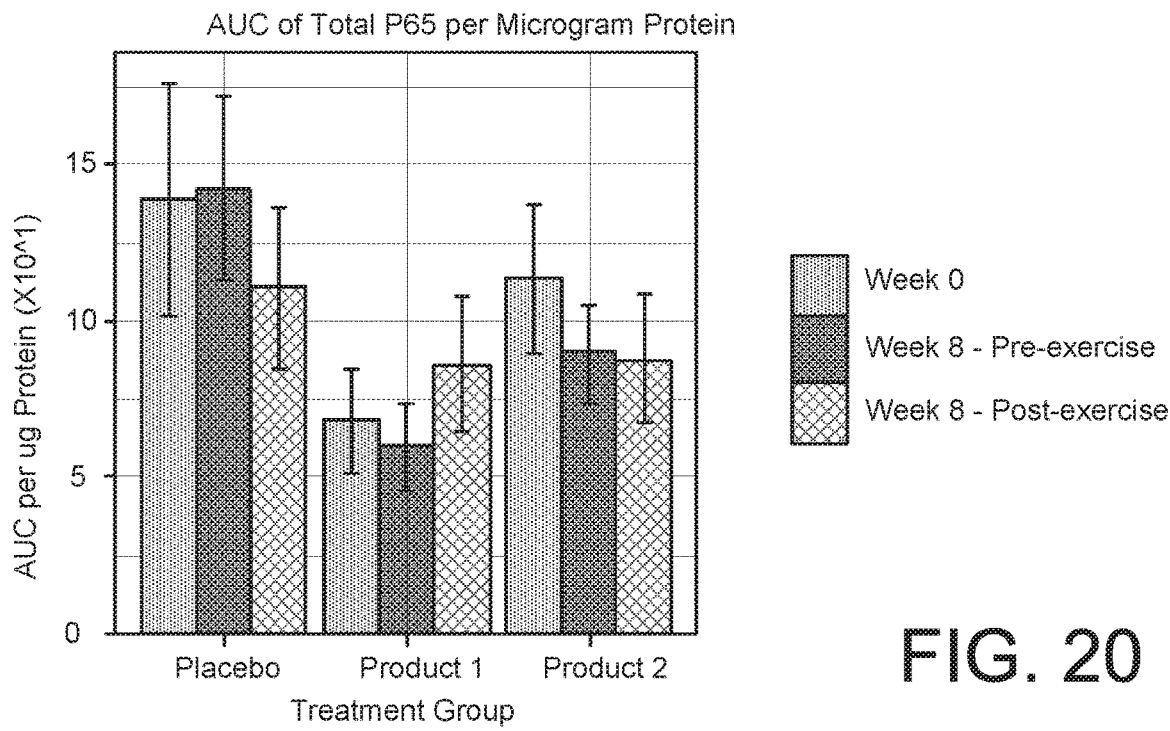

FIG. 20

The Change in Total-P65 from Baseline to Week 8 Pre and Post Exercise for Participants Supplemented with either Placebo, Carnipure product 1, or Carnipure product 2 in the PP Population (N = 33).

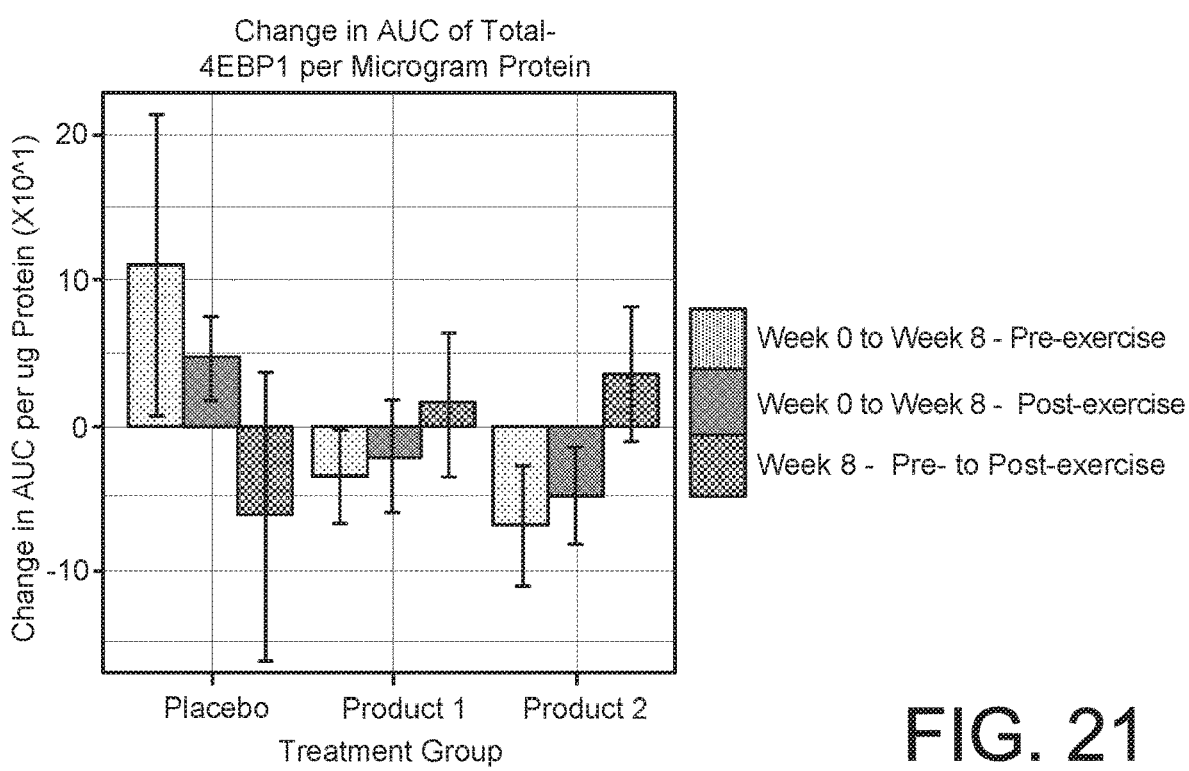

FIG. 21

The AUC per µg of protein for Total-P50 from Baseline to Week 8 Pre and Post Exercise for Participants Supplemented with either Placebo, Carnipure product 1, or Carnipure product 2 in the PP Population (N = 33).

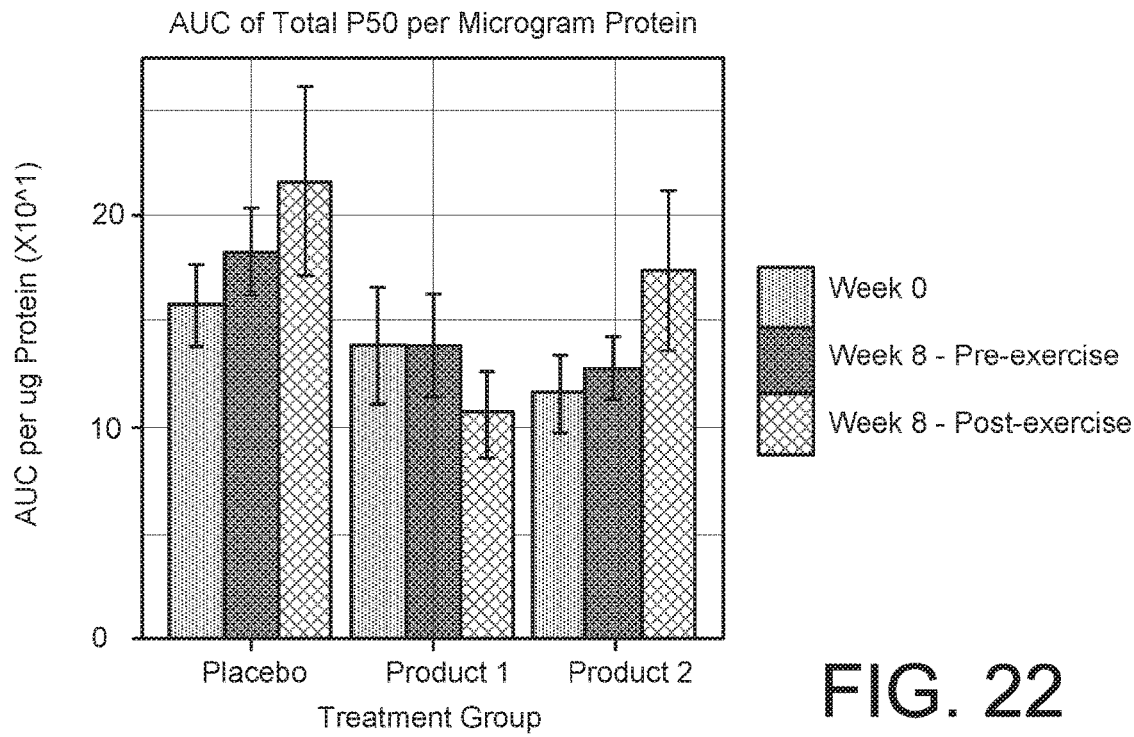

FIG. 22

The Change in Total-P50 from Baseline to Week 8 Pre and Post Exercise for Participants Supplemented with either Placebo, Carnipure product 1, or Carnipure product 2 in the PP Population (N = 33).

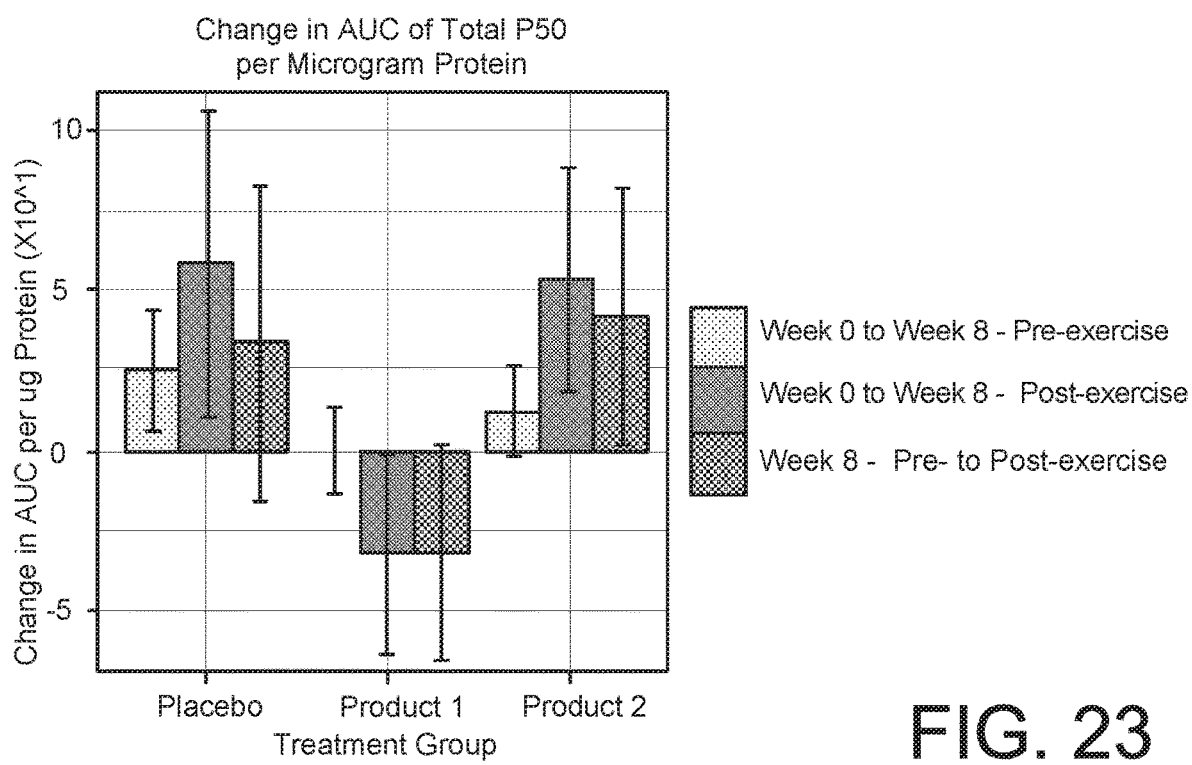

FIG. 23

METHOD AND COMPOSITION FOR INCREASING MUSCLE PROTEIN SYNTHESIS AND/OR FUNCTIONAL STRENGTH IN MAMMALS

RELATED APPLICATIONS

The present application is based on and claims priority to U.S. Provisional Patent application Ser. No. 62/273,880, filed on Dec. 31, 2015, and U.S. Provisional Patent application Ser. No. 62/269,573, filed on Dec. 18, 2015, both of which are incorporated herein by reference.

BACKGROUND

Many mammals may experience functional deterioration as they enter mid to late adulthood. Functional deterioration relates to a decline in the ability to carry out basic functional activities such as eating and walking. Compromised motor function can, in turn, lead to loss of independence and a decreased quality of life.

A major contributor to functional deterioration in both sedentary and physically active mammals is sarcopenia, an age-related condition characterized by a gradual decline in muscle mass, strength, and function. In sarcopenia, the body experiences a global shift from muscle protein synthesis to muscle degradation.

Proteinogenic amino acid molecules can be categorized as essential and non-essential amino acids. Non-essential amino acids, which can be synthesized in the body, include alanine, asparagine, aspartic acid, glutamic acid, arginine, cysteine, glutamine, tyrosine, glycine, proline, and serine. Essential amino acids, such as histidine, isoleucine, leucine, lysine, methionine, phenylalanine, threonine, tryptophan, and valine, cannot be biosynthesized and instead must be consumed via food or supplementation. In muscle protein synthesis, the availability of essential amino acids is rate-limiting. Therefore, supplementation of essential amino acids can potentiate protein synthesis. Muscle protein synthesis is activated by the mammalian target of rapamycin (mTOR) pathway. The mTOR pathway senses and responds to changes in amino acids and growth factors such as insulin-like growth factor (IGF-1). In particular, the mTOR complex phosphorylates ribosomal protein S6K, which in turn phosphorylates ribosomal protein S6 and substrates eIF4B and 4EBP1, consequently promoting mRNA translation and protein synthesis. The proteins involved in the mTOR pathway can serve as biomarkers for protein synthesis.

The NFκβ (p65/p50) pro-inflammatory signaling pathway has also been implicated in regulating muscle functionality. NFκβ protein levels are strongly upregulated in muscle atrophy, while inhibition of the NFκβ (p65/p50) pathway can prevent muscle degradation.

The ubiquitin-proteasome system (UPS) can facilitate muscle degradation, breaking down muscle proteins into peptides and then free amino acids. In the UPS-pathway, target muscle proteins are tagged with a degradation signal and then degraded into peptides by the 26s proteasome. The UPS-pathway can be mediated by atrogin-1 and MuRF-1, two E3 ubiquitin-protein ligases, and by cytokines such as interleukin (IL)-6, IL-8, and tumor necrosis factor (TNF)-α, which produce pro-inflammatory signals. These factors can serve as biomarkers for muscle protein degradation. Protein degradation and functional deterioration may be amplified in mammals with sarcopenia and in older mammals with sedentary lifestyles. Muscle protein building requires both new protein synthesis and prevention of protein degradation. While physical activity, even in light or moderate amounts, can lead to muscle hypertrophy and increased functionality, muscle disuse results in a decrease in protein synthesis and an increase in muscle breakdown. In addition, mTOR activation can be delayed in older adults, leading to decreased protein synthesis. Furthermore, extended periods of inactivity can lead to a decreased protein synthetic response to amino acid supplementation. Sarcopenia-related functional deterioration can be a reinforcing loop, as muscle loss and decreased functionality can interfere with physical activity. In turn, decreased physical activity leads to further muscle loss and decreased functionality.

In the past, leucine and creatine have been administered to mammals in order to increase muscle mass and strength. In particular, many of the supplements administered to elderly mammals for increasing muscle protein synthesis comprise complicated and expensive mixtures of amino acids. For example, U.S. Pat. No. 7,790,688, which is incorporated by reference herein, discloses compositions containing a complex blend of essential amino acids, creatine, and low-glycemic carbohydrates. Further, it is well-known in the art that ingestion of 20 grams or more of essential amino acids is necessary for stimulation of muscle protein synthesis in the elderly. As protein intake increases, however, urea production can increase in some individuals.

Consequently, a need exists for a supplement that can increase muscle protein synthesis, lean mass, functional strength, and/or overall quality of life in mammals without having any substantial adverse effects on other body functions. A need also exists for a simpler and less expensive supplement that can improve muscle mass and/or functional strength leading to increase in physical activity in elderly mammals and mammals with sarcopenia.

SUMMARY

The present disclosure is generally directed to a method and composition for increasing protein synthesis and/or functional strength in mammals. The present disclosure is also directed to a method and composition for slowing down or delaying muscle wasting or sarcopenia in sedentary and physically active mammals.

In accordance with the present disclosure, the method comprises the step of administering to a mammal an effective amount of a protein building composition. Of particular advantage, the protein building composition can increase muscle protein synthesis, lean mass, functional strength, physical activity, and/or overall quality of life in mammals without having any substantial adverse effects on other body functions.

The protein building composition may comprise a supplement, a food product, or a beverage. For instance, the protein building composition can be incorporated into milkshake drinks, juices, cereal bars, vitamins including gummy vitamins, powders, foods or may be in the form of a supplement.

In one embodiment, the protein building composition may be administered to a mammal that has an age of more than 50% of its expected life span. In an alternate embodiment, the protein building composition may be administered to a mammal that has an age of less than 50% of its expected life span. The mammal may regularly participate in physical activity. In another embodiment, the mammal may participate mainly or exclusively in sedentary behavior. In a particular embodiment, the mammal is a human.

In one embodiment, the protein building composition may comprise at least two of any essential amino acid components, amino acid derivatives, and/or nitrogenous organic acids, such as creatine. The essential amino acid component may comprise leucine and derivatives and/or salts thereof. The amino acid derivative may comprise carnitine and derivatives and/or salts thereof. In one embodiment, the protein building composition comprises an amino acid derivative combined with an amino acid component. In an alternative embodiment, the protein building composition may comprise an amino acid derivative combined with a nitrogenous organic acid. In still another embodiment, the protein building composition may comprise a mixture of an amino acid derivative, an amino acid component, and a nitrogenous organic acid.

In one embodiment, the amino acid derivative comprises L-carnitine. In a particular embodiment, the amino acid derivative comprises L-carnitine L-tartrate. In a further embodiment, the protein building composition may contain a nitrogenous organic acid and derivatives and/or salts thereof. In one embodiment, the protein building composition may comprise creatine and derivatives and/or salts thereof.

In one embodiment, leucine and salts, metabolites, and/or derivatives thereof may be present in the amino acid component at a concentration greater than about 5% by mass. In one embodiment, a metabolite of leucine, such as β-Hydroxy β-methylbutyric acid (HMB), may be present in the amino acid component. In one embodiment, leucine is present in a concentration of about 10% to 90% by mass, such as about 20% to 80% by mass, such as about 30% to 70% by mass. In a preferred embodiment, leucine is present in a concentration of about 35 to 65% by mass.

In one embodiment, L-carnitine may be present in the amino acid component at a concentration greater than about 5% by mass. L-carnitine may be present in a substantially pure crystalline form or as salts, metabolites, and/or lipid and non-lipid derivatives of L-carnitine. In one embodiment, L-carnitine is present in a concentration of about 10% to 90% by mass, such as about 20% to 80% by mass, such as about 25% to 75% by mass, such as about 30% to 60% by mass. In a preferred embodiment, L-carnitine is present in a concentration of about 40% to 70% by mass.

In one embodiment, creatine and salts, metabolites, and/or derivatives thereof may be present in the supplement composition at a concentration of greater than about 0.5% by mass, such as greater than about 1% by mass, such as greater than about 5% by mass, such as greater than about 10% by mass, such as greater than about 20% by mass, such as greater than about 40% by mass, such as greater than about 60% by mass, such as greater than about 80% by mass, such as greater than about 90% by mass, such as greater than about 99% by mass. In a preferred embodiment, creatine is present in the composition at a concentration of about 30% to about 45% by mass. In one embodiment, creatine may comprise creatine monohydrate and chelated creatine, such as magnesium-chelated creatine and other metal-chelated creatine. The protein building composition can be administered to the mammal regularly or occasionally. For instance, the protein building composition can be administered to the mammal at least every one to three days, such as daily. In one embodiment, a daily portion may be taken in one or several servings. Each dose may be from about 5 milligrams to about 30,000 milligrams, such as from about 5 milligrams to about 20,000 milligrams, such as from about 50 milligrams to about 10,000 milligrams. Each dose may be from about 1 milligram per kilogram body weight per day to about 10,000 milligrams per kilogram per day, such as from about 5 milligrams per kilogram per day to about 5,000 milligrams per kilogram per day. The protein building composition can be administered orally and can be combined with a food composition.

In one embodiment, the pharmaceutical composition of the present disclosure is combined with various additives and ingredients in order to improve various properties. For instance, the protein building composition of the present disclosure may be combined with a stabilizer package for reducing the hydroscopic properties of the composition. The stabilizer package can also make the composition easier to handle and/or pour, especially when the composition comprises a granular composition.

In one embodiment, for instance, the present disclosure is directed to a pharmaceutical composition comprising a protein building composition combined with a polymer binder and a stabilizer package. The stabilizer package may comprise oxide particles, such as silica, combined with a salt of a carboxylic acid. The salt of a carboxylic acid may comprise a salt of a fatty acid, such as a fatty acid having a carbon chain length of from about 6 carbon atoms to about 40 carbon atoms, such as from about 12 carbon atoms to about 28 carbon atoms. In one embodiment, the salt of the carboxylic acid comprises a stearate salt, such as calcium stearate, sodium stearate, magnesium stearate, mixtures thereof, and the like. The polymer binder, on the other hand, may comprise a polysaccharide and/or a film-forming polymer. The polymer binder, for instance, may comprise starch such as a modified starch, maltodextrin, gum arabic, arabinogalactan, a gelatin, or mixtures thereof.

In one embodiment, the pharmaceutical composition may further contain a coating material. The coating material may comprise a fat. The coating material may form a continuous or a discontinuous coating over the pharmaceutical composition. In one embodiment, the coating material comprises a hydrogenated palm oil combined with palm stearine. For instance, the hydrogenated palm oil and palm stearine may be combined at a weight ratio of from about 10:1 to about 1:1, such as from about 5:1 to about 3:1.

The present disclosure is also directed to a method of producing a pharmaceutical composition containing the protein building composition. The method includes the steps of combining the protein building composition with a polymer binder and a stabilizer package. In one embodiment, for instance, the protein building composition is first combined with the polymer binder via a spray dry process and then combined with the stabilizer package which may comprise a dry mix (i.e. a powder or granular material). The method may further include the step of optionally applying a coating material to the mixture containing the protein building composition, the polymer binder, and the stabilizer package. The coating material may comprise a fat, such as a hydrogenated oil.

In one embodiment, the pharmaceutical composition contains the oxide particles, such as the silica particles, in an amount from about 0.01% to about 1.5% by weight, the salt of the carboxylic acid in an amount from about 0.5% to about 5% by weight and the polymer binder in an amount from about 8% to about 40% by weight. When present, the coating material may be contained in the polymer composition in an amount from about 5% to about 35% by weight.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which:

FIG. 1 shows results obtained by the procedure described in Example 1;
FIG. 3 shows results obtained by the procedure described in Example 1;
FIG. 4 shows results obtained by the procedure described in Example 1;
FIG. 5 shows results obtained by the procedure described in Example 1;
FIG. 6 shows results obtained by the procedure described in Example 1;
FIG. 7 shows results obtained by the procedure described in Example 1;
FIG. 8 shows results obtained by the procedure described in Example 1;
FIG. 9 shows results obtained by the procedure described in Example 1;
FIG. 10 shows results obtained by the procedure described in Example 1;
FIG. 11 shows results obtained by the procedure described in Example 1;
FIG. 12 shows results obtained by the procedure described in Example 1;
FIG. 13 shows results obtained by the procedure described in Example 1;
FIG. 14 shows results obtained by the procedure described in Example 1;
FIG. 15 shows results obtained by the procedure described in Example 1;
FIG. 16 shows results obtained by the procedure described in Example 1;
FIG. 17 shows results obtained by the procedure described in Example 1;
FIG. 18 shows results obtained by the procedure described in Example 1;
FIG. 19 shows results obtained by the procedure described in Example 1;
FIG. 20 shows results obtained by the procedure described in Example 1;
FIG. 21 shows results obtained by the procedure described in Example 1;
FIG. 22 shows results obtained by the procedure described in Example 1;
FIG. 23 shows results obtained by the procedure described in Example 1.

Figure 2:
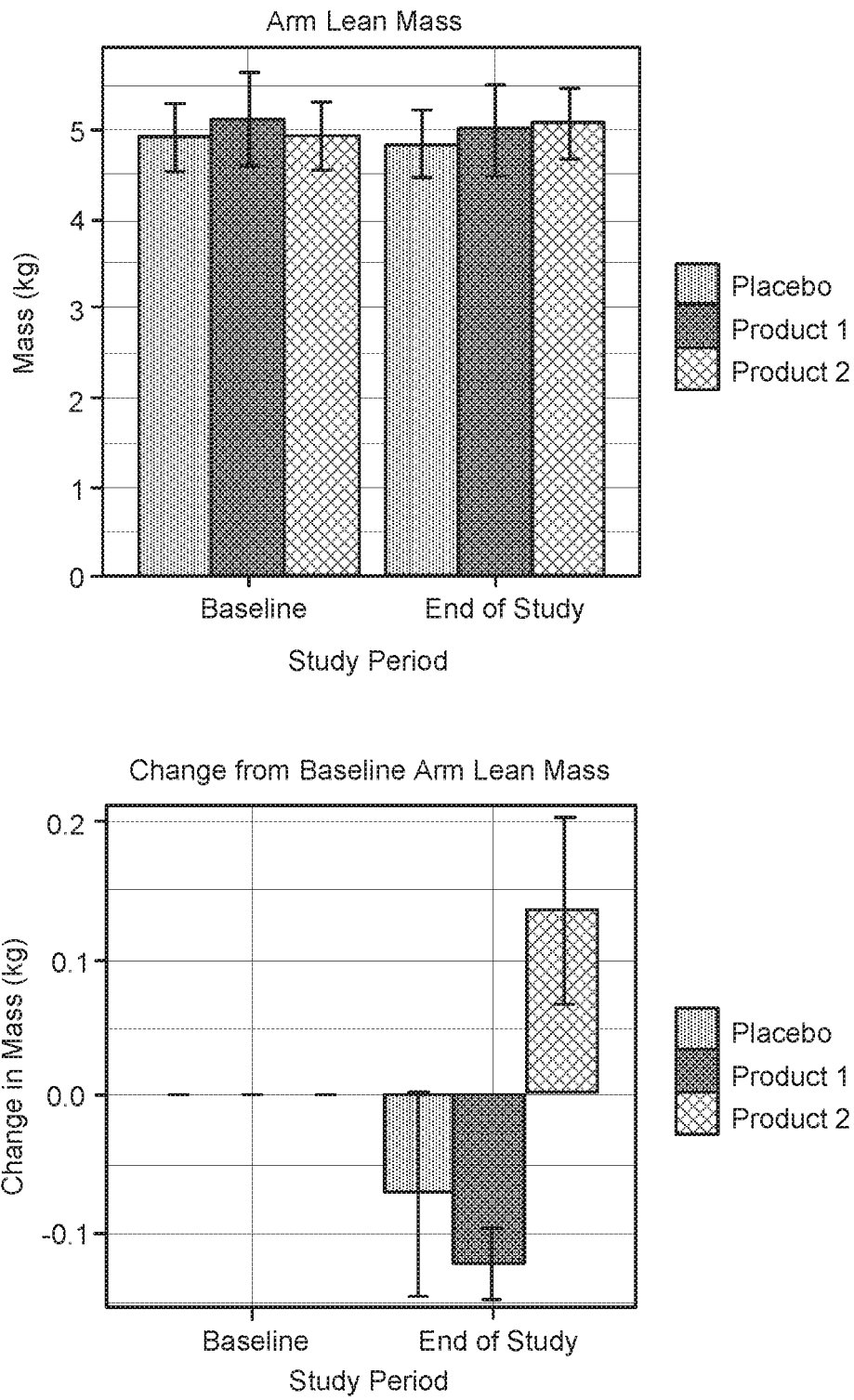
FIG. 2 shows results obtained by the procedure described in Example 1.

The Figures are graphical representations of the results obtained in the example described below.

Definitions

The term "MET," or "metabolic equivalent," means the ratio of the rate of energy expended during an activity to the rate of energy expended at rest. A body at rest has a rate of energy expenditure of 1 MET. If a body performs a 2 MET activity, the body has expended 2 times the energy used by the body at rest. The term "physical activity" means bodily movement with an energy expenditure rate equal to or greater than 3 MET. Non-limiting examples of "physical activity" include bicycling, sexual activity, giving birth, jogging, walking at a speed of about 3 mph or greater, calisthenics, jumping rope, running, sprinting, or any combinations thereof.

In one embodiment, "physical activity" can mean a negative energy balance in the mammal, such as weight loss, diets, aging, gestation, and lactation.

The term "physically active" means regularly participating in body movements with an energy expenditure rate of greater than or equal to 3 MET.

In one embodiment, "physically active" can mean regularly meeting medically recommended standards for amount, intensity, and type of physical activity performed by a mammal.

The terms "sedentary" or "sedentary activity" mean participating mainly or exclusively in body movements with an energy expenditure rate of less than 3 MET. Non-limiting examples of "sedentary" activities include sleeping, resting, sitting or reclining, watching television, writing, working at a desk, using a computer, typing, walking at a speed of less than about 3 mph, or any combinations thereof.

In one embodiment, "sedentary" can mean a failure to regularly meet medically recommended standards for amount, intensity, and type of physical activity performed by a mammal.

The term "L-carnitine" may contain L-carnitine and derivatives and/or salts thereof. L-carnitine can include L-carnitine base or derivatives and/or salts thereof including substantially pure crystalline L-carnitine, any fatty acid derivatives thereof, acetyl L-carnitine, valeryl L-carnitine, isovaleryl L-carnitine, benzyl L-carnitine, L-leucyl L-carnitine, L-valyl L-carnitine, other L-amino acyl carnitines, salts of L-amino acyl L-carnitine, L-carnitine HCL, L-carnitine L-tartrate, L-carnitine fumarate, propionyl L-carnitine, L-carnitine phosphate, acetyl L-carnitine L-aspartate, acetyl L-carnitine citrate, acetyl L-carnitine maleate, acetyl L-carnitine phosphate, acetyl L-carnitine fumarate, propionyl L-carnitine orotate, acetyl L-carnitine orotate, butyryl L-carnitine orotate, propionyl L-carnitine fumarate, L-carnitine oxalate, L-carnitine sulfate, GPLC glycine propionyl L-carnitine, and the like.

The term "mammal" includes any mammal that may experience skeletal muscle degradation or synthesis and includes human, canine, equine, feline, bovine, ovine, or porcine mammals.

The phrase "effective amount" means an amount of a compound that promotes, improves, stimulates, or encourages a response to the particular condition or disorder or the particular symptom of the condition or disorder.

The term "supplement" means a product in addition to the normal diet of the mammal but may be combined with a mammal's normal food or drink composition. The supplement may be in any form but not limited to a solid, liquid, gel, capsule, or powder. A supplement may also be administered simultaneously with or as a component of a food composition which may comprise a food product, a beverage, a pet food, a snack, or a treat. In one embodiment, the beverage may be an activity drink.

The term "functional strength" means an individual's ability to competently and safely perform daily life activities. In one embodiment, functional strength may be associated with energy, muscle potency, agility, flexibility, balance, and injury resistance.

DETAILED DESCRIPTION

It is to be understood by one of ordinary skill in the art that the present discussion is a description of exemplary embodiments only, and is not intended as limiting the broader aspects of the present disclosure.

The present disclosure is directed to a method and composition for increasing muscle protein synthesis and/or functional strength in mammals. As will be explained below, the present disclosure is generally directed to a protein building composition that when administered to a mammal in an effective amount preserves or increases muscle mass and function by increasing muscle protein synthesis and/or functional strength and/or decreasing protein degradation. The present disclosure is further generally directed to administering to a mammal an effective amount of a protein building composition that increases muscle protein synthesis and/or functional strength.

In one embodiment, the protein building composition comprises an amino acid derivative combined with at least one other component. For instance, the amino acid derivative may be combined with an amino acid, an organic acid, or both an amino acid and an organic acid. The amino acid derivate may comprise a carnitine, such as L-carnitine. The amino acid may comprise an essential amino acid. In one embodiment, the amino acid may comprise leucine. The protein building composition may further comprise an organic acid, such as a nitrogenous organic acid. The organic acid may comprise creatine.

The inventors of the present disclosure unexpectedly discovered that the components of the protein building composition disclosed herein synergistically work together to increase muscle protein synthesis and/or functional strength. Surprisingly, it was discovered that administering a protein building composition containing L-carnitine, combined with leucine, creatine, or both leucine and creatine to a mammal can increase muscle protein synthesis and/or functional strength while also preventing muscle degradation, decreasing inflammation, and improving upper and lower body strength. In one embodiment, the protein building composition may also contain vitamin D3. Of particular advantage, the above results can be achieved without administering the high dosage of amino acids required in previous compositions. In addition, the protein building composition of the present disclosure produces no noticeable side effects. For instance, administering the protein building composition regularly can be done without showing any clinically significant change in kidney function.

The protein building composition of the present disclosure can be a nutritional supplement in the form of a pill, tablet or capsule. Alternatively, the protein building composition may be incorporated into a food or beverage. For instance, the protein building composition may be incorporated in to a milkshake drink, a juice, a cereal bar, a vitamin such as a gummy vitamin, or a powder. The powder can be mix with any suitable liquid for ingestion.

The amino acid derivative may be any suitable carnitine, such as L-carnitine and any derivatives and/or salts thereof. L-carnitine is a quaternary amine that can be biosynthesized from lysine and methionine. L-carnitine is known to promote beta-oxidation of long-chain fatty acids by facilitating their transfer across the mitochondrial membrane. L-carnitine may be present in a substantially pure crystalline form or as salts, metabolites, and/or lipid and non-lipid derivatives of L-carnitine.

In one embodiment, L-carnitine may be present in the composition at a concentration greater than about 5% by mass, such as greater than about 10% by mass, such as greater than about 15% by mass, such as greater than about 20% by mass, such as greater than about 25% by mass, such as greater than about 30% by mass, such as greater than about 35% by mass, such as greater than about 40% by mass, such as greater than about 45% by mass, such as greater than about 50% by mass, such as greater than about 55% by mass, such as greater than about 60% by mass, such as greater than about 65% by mass, such as greater than about 70% by mass, such as greater than about 75% by mass. In general, L-carnitine may be present in the composition at a concentration less than about 75% by mass, such as less than about 70% by mass, such as less than about 65% by mass, such as less than about 60% by mass, such as less than about 55% by mass, such as less than about 50% by mass, such as less than about 45% by mass, such as less than about 40% by mass, such as less than about 35% by mass, such as less than about 30% by mass, such as less than about 25% by mass, such as less than about 20% by mass, such as less than about 15% by mass, such as less than about 10% by mass.

As stated above, the composition may comprises an amino acid in combination with the amino acid derivate. The amino acid may be leucine and any derivatives, metabolites, and/or salts thereof. Leucine is a branched-chain α-amino acid. Leucine is known to stimulate protein synthesis via association with eukaryotic initiation factors in translation. In one embodiment, the amino acid may comprise a metabolite of leucine, such as HMB.

In one embodiment, leucine may be present in the amino acid component at a concentration greater than about 10% by mass, such as greater than about 15% by mass, such as greater than about 20% by mass, such as greater than about 25% by mass, such as greater than about 30% by mass, such as greater than about 35% by mass, such as greater than about 40% by mass, such as greater than about 45% by mass, such as greater than about 50% by mass, such as greater than about 55% by mass, such as greater than about 60% by mass, such as greater than about 65% by mass, such as greater than about 70% by mass, such as greater than about 75% by mass. In general, leucine may be present in the amino acid component at a concentration less than about 75% by mass, such as less than about 70% by mass, such as less than about 65% by mass, such as less than about 60% by mass, such as less than about 55% by mass, such as less than about 50% by mass, such as less than about 45% by mass, such as less than about 40% by mass, such as less than about 35% by mass, such as less than about 30% by mass, such as less than about 25% by mass, such as less than about 20% by mass, such as less than about 15% by mass.

As described above, the protein building composition may comprise the amino acid derivative in combination with either an amino acid or an organic acid or may comprise an amino acid derivative in combination with both an amino acid or an organic acid. The organic acid may be creatine and derivatives and/or salts thereof. Creatine is a nitrogenous organic acid that can be biosynthesized from glycine and arginine. Creatine increases the formation of ATP and in a phosphorylated form serves as an energy reserve in skeletal muscles. Creatine can improve the physiological response to high-intensity and resistance exercise.

In one embodiment, the composition may include creatine and derivatives and analogs and/or salts thereof. In one embodiment, the composition may include creatine phosphate; creatine monohydrate; creatine ethyl ester; magnesium creatine chelate; creatine HCL; creatine-MG-complex (acetate); phosphocreatine-Mg-complex (acetate); creatine sugar amides and salts thereof as described in U.S. Pat. No. 8,546,369, incorporated by reference herein; (Boc)2-creatine and derivatives thereof as described in PCT Publication WO 2014/097335, incorporated by reference herein; other derivatives and salts of creatine; and any combinations thereof.

In one embodiment, creatine may be present in the amino acid component at a concentration greater than about 15% by mass, such as greater than about 20% by mass, such as greater than about 25% by mass, such as greater than about 30% by mass, such as greater than about 35% by mass, such as greater than about 40% by mass, such as greater than about 45% by mass, such as greater than about 50% by mass, such as greater than about 55% by mass, such as greater than about 60% by mass, such as greater than about 65% by mass, such as greater than about 70% by mass, such as greater than about 75% by mass, such as greater than about 80% by mass. In general, creatine may be present in the amino acid component at a concentration less than about 80% by mass, such as less than about 75% by mass, such as less than about 70% by mass, such as less than about 65% by mass, such as less than about 60% by mass, such as less than about 55% by mass, such as less than about 50% by mass, such as less than about 45% by mass, such as less than about 40% by mass, such as less than about 35% by mass, such as less than about 30% by mass, such as less than about 25% by mass, such as less than about 20% by mass, such as less than about 15% by mass, such as less than about 10% by mass.

In one embodiment, the composition may comprise one or more vitamins. In one particular embodiment, the composition may comprise vitamin D3. Vitamin D can regulate muscle contractility. Other vitamins may include but are not limited to vitamin A, vitamin B1, vitamin B2, vitamin B3, vitamin B6, vitamin B9, vitamin B12, vitamin C, vitamin E, vitamin K, riboflavin, niacin, folic acid, pyridoxine, thiamine, pantothenic acid, biotin, and any combinations thereof. The composition may further comprise other minerals, herbs, botanicals, and essential fatty acids. In one embodiment, the protein building composition may comprise magnesium and/or salts thereof.

In one embodiment, the one or more vitamins may be present in the composition in an amount of about 1 to about 5,000 IU per dose, such as about 10 to about 2,500 IU per dose, such as about 50 to about 1,500 IU per dose, such as about 100 IU to about 1,000 IU per dose, such as about 250 IU to about 750 IU per dose, such as about 300 IU to about 600 IU per dose.

In one embodiment, the amino acids, amino acid derivatives, and/or organic acids and derivatives and/or salts thereof may be included in the composition as free form organic compounds. Alternately, the components may be included in the composition as intact proteins and/or other macromolecules. In a further embodiment, the amino acids, amino acid derivatives, and/or organic acids and derivatives and/or salts thereof may be included in the composition as a combination of free form organic compounds and intact protein and/or other macromolecules.

The different components can be present in the protein building composition at various ratios depending upon the particular application and the desired result. The weight ratio between the amino acid derivative and the amino acid, for instance, can generally be from about 1:10 to about 10:1, such as from about 1:3 to about 3:1. In one embodiment, the weight ratio between the amino acid derivative and the amino acid may be from about 1:1 to about 1:2.

The weight ratio between the amino acid derivative and the organic acid, on the other hand, can generally be from about 1:10 to about 5:1, such as from about 1:1 to about 1:5, such as from about 1:1 to about 1:3. In one particular embodiment, the protein building composition contains the amino acid derivative combined with the amino acid and the organic acid. The weight ratio between the amino acid derivative and the amino acid can be about 3:4, while the weight ratio between the amino derivative and the organic acid can be about 1:2.

The present disclosure is also directed to methods of administering the protein building composition disclosed herein. L-carnitine in combination with leucine and creatine has been discovered to increase protein synthesis and/or functional strength in mammals. In order to increase muscle protein synthesis and/or functional strength, the present disclosure is directed to a method of administering to a mammal an effective amount of a protein building composition. The above advantages and benefits may be realized without any adverse consequences. In addition, in one embodiment, the mammal may experience no clinically substantial difference in kidney function.

In one embodiment, a mammal is administered an effective amount of an protein building composition containing an amino acid component. The amino acid component may comprise leucine. Leucine may be administered in a dosage from about 5 to 10,000 milligrams per day, such as from about 5 to about 5,000 milligrams per day, such as from about 50 milligrams to about 3,000 milligrams per day. The dosage, for instance, can be greater than about 100 milligrams per day, such as greater than about 250 milligrams per day, such as greater than about 500 milligrams per day, such as greater than about 750 milligrams per day. Based on body mass, the dosage can be from about 1 milligram per kilogram of body weight per day to about 1,000 milligrams per kilogram body weight per day. For example, the dosage may be from about 5 milligrams per kilogram body weight per day to about 750 milligrams per kilogram body weight per day. In one particular embodiment, the dosage can be from about 10 milligrams per kilogram body weight per day to about 500 milligrams per kilogram body weight per day. In another particular embodiment, the dosage can be greater than about 1 milligrams per kilogram body weight per day, greater than about 5 milligrams per kilogram body weight per day, greater than about 10 milligrams per kilogram body weight per day, greater than about 15 milligrams per kilogram body weight per day, greater than about 20 milligrams per kilogram body weight per day, greater than about 25 milligrams per kilogram body weight per day, greater than about 30 milligrams per kilogram body weight per day, or greater than about 35 milligrams per kilogram body weight per day.

The mammal can also be administered an effective amount of an amino acid derivative. The amino acid derivative may comprise L-carnitine. L-carnitine may be administered in a dosage from about 5 to 10,000 milligrams per day, such as from about 5 to about 5,000 milligrams per day, such as from about 50 milligrams to about 3,000 milligrams per day. The dosage, for instance, can be greater than about 100 milligrams per day, such as greater than about 250 milligrams per day, such as greater than about 500 milligrams per day, such as greater than about 750 milligrams per day. Based on body mass, the dosage can be from about 1 milligram per kilogram of body weight per day to about 1,000 milligrams per kilogram body weight per day. For example, the dosage may be from about 5 milligrams per kilogram body weight per day to about 750 milligrams per kilogram body weight per day. In one particular embodiment, the dosage can be from about 10 milligrams per kilogram body weight per day to about 500 milligrams per kilogram body weight per day. In another particular embodiment, the dosage can be greater than about 1 milligrams per kilogram body weight per day, greater than about 5 milligrams per kilogram body weight per day, greater than about 10 milligrams per kilogram body weight per day, greater than about 15 milligrams per kilogram body weight per day, greater than about 20 milligrams per kilogram body weight per day, greater than about 24 milligrams per kilogram body weight per day, greater than about 28 milligrams per kilogram body weight per day, or greater than about 30 milligrams per kilogram body weight per day.

In one embodiment, a mammal is administered an effective amount of an protein building composition containing an organic acid and derivative and/or salt thereof. The organic acid may comprise creatine. Creatine may be administered in a dosage from about 5 to 15,000 milligrams per day, such as from about 5 to about 10,000 milligrams per day, such as from about 50 milligrams to about 5,000 milligrams per day. The dosage, for instance, can be greater than about 100 milligrams per day, such as greater than about 500 milligrams per day, such as greater than about 1,000 milligrams per day, such as greater than about 1,250 milligrams per day. Based on body mass, the dosage can be from about 1 milligram per kilogram of body weight per day to about 1,000 milligrams per kilogram body weight per day. For example, the dosage may be from about 5 milligrams per kilogram body weight per day to about 750 milligrams per kilogram body weight per day. In one particular embodiment, the dosage can be from about 10 milligrams per kilogram body weight per day to about 500 milligrams per kilogram body weight per day. In another particular embodiment, the dosage can be greater than about 1 milligrams per kilogram body weight per day, greater than about 5 milligrams per kilogram body weight per day, greater than about 10 milligrams per kilogram body weight per day, greater than about 15 milligrams per kilogram body weight per day, greater than about 20 milligrams per kilogram body weight per day, greater than about 30 milligrams per kilogram body weight per day, greater than about 40 milligrams per kilogram body weight per day, or greater than about 50 milligrams per kilogram body weight per day.

The protein building composition can be administered regularly, such as at least two to four times a week. For instance, the protein building composition may be administered to the mammal at least every one to three days. Further, the protein building composition may be administered more than one time per day. For instance, the protein building composition may be administered to the mammal one to four times per day. In one particular embodiment, the protein building composition is administered daily. The dosage can be from about 5 to 30,000 milligrams per day, such as from about 5 to about 20,000 milligrams per day, such as from about 10 milligrams to about 10,000 milligrams per day, such as from about 20 milligrams to about 5,000 milligrams per day, such as from about 50 milligrams to about 2,500 milligrams per day. Based on body mass, the dosage can be from about 1 milligram per kilogram of body weight per day to about 10,000 milligrams per kilogram body weight per day. For example, the dosage may be from about 5 milligrams per kilogram body weight per day to about 7,500 milligrams per kilogram body weight per day, such as from about 10 milligrams per kilogram body weight per day to about 5,000 milligrams per kilogram body weight per day, such as from about 15 milligrams per kilogram body weight per day to about 2,500 milligrams per kilogram body weight per day, such as from about 20 milligrams per kilogram body weight per day to about 1,000 milligrams per kilogram body weight per day, such as from about 25 milligrams per kilogram body weight per day to about 750 milligrams per kilogram body weight per day, such as from about 30 milligrams per kilogram body weight per day to about 500 milligrams per kilogram body weight per day, such as from about 35 milligrams per kilogram body weight per day to about 250 milligrams per kilogram body weight per day.

The protein building composition can be administered to the mammal in any suitable form using any suitable administration route. For example, the composition can be administered orally alone, in combination with a food composition, or as part of a food composition. The composition may also be part of a dietary supplement or as a nutraceutical composition.

The protein building composition can be administered orally as a solid, liquid, suspension, or gas. The composition may be administered via buccal or sublingual administration. In one embodiment, the protein building composition may be administered as a capsule, tablet, caplet, pill, troche, drop, lozenge, powder, granule, syrup, tea, drink, thin film, seed, paste, herb, botanical, and the like.

In addition to being administered orally, the supplement dose can also be administered using other routes including intranasal, intravenous, intramuscular, intragastric, and the like.

When the protein building composition is combined with a food or beverage composition, the food or beverage composition may comprise any suitable composition for consumption by the mammal. Such compositions include complete foods or beverages intended to supply the necessary dietary requirements for mammal or food supplements such as treats and snacks. The food composition may comprise pellets, a drink, a bar, a prepared food contained in a can, a milk shake drink, a juice, a dairy food product, or any other functional food composition. The food composition may also comprise any form of a supplement such as a pill, soft gel, gummy figurine, wafer, or the like.

A food composition ingested by the mammal in addition to the protein building composition may also be rich in L-carnitine, leucine, and/or creatine. The protein building composition of the present disclosure, for instance, is intended to provide additional L-carnitine, leucine, and/or creatine in addition to the normal amounts contained in a standard diet and/or the amounts produced by the body.

The mammal treated in accordance with the present disclosure can comprise any suitable mammal. For instance, the mammal may be human or canine. The protein building composition can be fed to a mammal of any age such as from parturition through the adult life in the mammal. In various embodiments the mammal may be a human, dog, a cat, a horse, a pig, a sheep, or a cow. In many embodiments, the mammal can be in early to late adulthood. For instance, the active mammal may have an age that is at least 10%, such as least 15%, such as least 20%, such as least 25%, such as least 30%, such as least 35%, such as least 40%, such as least 45%, such as least 50%, such as least 55%, such as least 60%, such as least 65%, such as least 70%, such as least 75%, such as least 85%, such as least 90%, such as least 95% of its expected life span. The mammal may have an age such that it is less than about 95%, such as less than about 90%, such as less than about 85%, such as less than about 80%, such as less than about 75%, such as less than about 70%, such as less than about 65%, such as less than about 60%, such as less than about 55%, such as less than about 50%, such as less than about 45%, such as less than about 40%, such as less than about 35%, such as less than about 30%, such as less than about 25%, such as less than about 20%, such as less than about 15%, such as less than about 10% of its expected life span. A determination of life span may be based on actuarial tables, calculations, or the like.

The protein building composition may be administered to the mammal according to the present disclosure regardless of the frequency, intensity, or type of physical activity performed by the mammal. The mammal may participate in physical activities with various MET values. In one embodiment, the mammal may regularly participate in light to intense physical activity. Light physical activity may have a MET of from about 3 MET to about 6 MET. Moderate physical activity may have a MET of from about 6 MET to about 10 MET, Intense physical activity may have a MET of about 10 MET or greater. In another embodiment, the mammal may infrequently participate in physical activity. In yet another embodiment, the mammal may lead a sedentary lifestyle, wherein the mammal may rarely or never participate in physical activity. In a sedentary lifestyle, a mammal may participate mainly or exclusively in sedentary activities.

The protein building composition may be administered to the mammal before, during, or after a period of physical activity. Alternately, the composition may be administered to the mammal before, during, or after a period of sedentary activity. For instance, the composition may be administered to the mammal during an extended period of bed rest or other extended period of inactivity.

The protein building composition is administered in an amount sufficient to increase muscle protein synthesis, increase functional strength, or increase both muscle protein synthesis and functional strength without requiring the mammal to participate in physical activity.

Muscle protein synthesis, in one embodiment, can be determined by monitoring the biomarkers, mTOR expression and phosphorylation and its related upstream and downstream proteins in the pathway, in skeletal muscle. Specifically, mTOR expression can be determined and recorded before and after a period of activity. For a mammal treated in accordance with the present disclosure, mTOR expression before and after a period of time may vary by more than 10%, such as by more than 20%, such as by more than 40%, such as by more than 60%, such as by more than 80%, such as by more than 100%, such as by more than 150%, such as by more than 200%.

In one embodiment, the mammals treated in accordance with the present disclosure may have total mTOR values after a period of activity that are at least 10%, such as at least 20%, such as at least 30%, such as at least 40%, such as at least 50%, such as at least 60%, such as at least 100% greater than the same mammal that is not administered the protein building composition.

Protein synthesis can be monitored by androgens, androgen receptors, insulin, IGF-1, IGF-1 receptors and any known stimulator of protein synthesis.

In addition to increased muscle protein synthesis, the protein building composition can also increase functional strength. In particular, the protein building composition can increase lean muscle mass and upper and lower body strength. Functional strength can be measured by a composite endpoint of strength and muscle measures. The composite endpoint may be the product of the values for muscle mass (kg), upper extremity strength by dynamometer (kg), lower extremity strength by dynamometer (kg), and 6-minute walk test (meters). Comparative measurements can be taken prior to and after a period of activity.

In one embodiment, mammals treated in accordance with the present disclosure may have composite endpoints after a certain period of time that are at least 10%, such as at least 25%, such as at least 50%, such as at least 75%, such as at least 100% more than the same mammal that is not administered the L-carnitine supplement.

The protein building composition of the present disclosure may also reduce inflammation. Inflammation, in one embodiment, can be determined by monitoring the biomarker, TNF-α, in skeletal muscle. TNF-α is an inflammatory marker involved in protein degradation. Reduction in TNF-α values may indicate a reduction in protein degradation and muscle wasting. TNF-α values can be determined and recorded before and after a period of activity. For a mammal treated in accordance with the present disclosure, TNF-α values before and after a period of time may vary by more than 0.5%, such as by more than 1%, such as by more than 5%, such as by more than 10%, such as by more than 20%, such as by more than 40%, such as by more than 60%, such as by more than 80%, such as by more than 100%, such as by more than 150%, such as by more than 200%.

In one embodiment, the mammals treated in accordance with the present disclosure may have total TNF-α values after a period of activity that are at least 0.5%, such as at least 1%, such as at least 5%, such as at least 10%, such as at least 20%, such as at least 30%, such as at least 40%, such as at least 50%, such as at least 60%, such as at least 100% less than the same mammal that is not administered the protein building composition.

Reduced inflammation can lead to decreased protein degradation.

In one embodiment, the compositions of the present disclosure may contain other amino acids, including but not limited to alanine, arginine, asparagine, aspartate, cysteine, glutamic acid, glutamine, glycine, proline, serine, tyrosine, histidine, isoleucine, lysine, methionine, phenylalanine, threonine, tryptophan, valine, and any combinations thereof.

The protein building composition of the present disclosure may further comprise one or more excipients. Exemplary but non-limiting excipients include antiadherents, such as magnesium stearate; binders, such as saccharides, sugar alcohols, gelatin, and synthetic polymers; coatings, such as cellulose ether hydroxypropyl methylcellulose (HPMC), shellac, corn protein zein, gelatin, fatty acids, and waxes; coloring agents, such as titanium oxide and azo dyes; disintegrants, such as modified starch sodium starch glycolate and crosslinked polymers including polyvinylpyrrolidone and sodium carboxymethyl cellulose; fillers, such as maltodextrin; flavoring agents, such as mint, liquorice, anise, vanilla, and fruit flavors including peach, banana, grape, strawberry, blueberry, raspberry, and mixed berry; glidants, such as fumed silica, talc, and magnesium carbonate; lubricants, such as talc, silica, and fats including vegetable stearin, magnesium stearate, and stearic acid; preservatives, such as antioxidants, vitamins, retinyl palmitate, selenium, the amino acids cysteine and methionine, citric acid, sodium citrate, and parabens; sorbents; sweeteners, such as sucrose and sucralose; and vehicles, such as petrolatum and mineral oil.

In one embodiment, the protein building composition of the present disclosure may be combined with various additives and components that can improve one or more properties of the composition. For example, in one embodiment, the additive composition may be combined with a stabilizer package that may serve to stabilize at least one property of the composition. In one particular embodiment, for instance, a stabilizer package may be added to the composition in an amount sufficient to reduce the hydroscopic properties of the composition and/or prevent the composition from absorbing moisture. A stabilizer composition may also be combined with the protein building composition in order to improve the handling properties of the composition. For instance, the stabilizer package may allow the composition to have better flow properties, especially when in granular form.

In one embodiment, the protein building composition may be combined with a polymer binder in conjunction with a stabilizer package. In addition, a coating material may also be applied to the composition after the composition has been combined with the polymer binder and the stabilizer package. The coating material, for instance, may contain at least one fat. In accordance with the present disclosure, the above components can be added to any suitable pharmaceutical composition in addition to the protein building composition of the present disclosure. For instance, the above components may be added to any pharmaceutical composition containing a carnitine or an amino acid.

The polymer binder and the stabilizer package may be combined with the protein building composition in a manner that homogeneously incorporates the stabilizer package into the product. In one embodiment, for instance, the protein building composition of the present disclosure is first combined with a polymer binder, such as through a spray dry process, and then combined with the stabilizer package. The polymer binder may comprise any suitable pharmaceutically acceptable polymer, such as film-forming polymers and/or polysaccharides. Particular examples of polymer binders that may be used in accordance with the present disclosure include starch, maltodextrin, gum arabic, arabinogalactan, gelatin, and mixtures thereof. In one embodiment, the polymer binder is added to the pharmaceutical composition in an amount of at least about 5% by weight, such as at least about 8% by weight, such as at least about 10% by weight, such as at least about 15% by weight. One or more polymer binders are present in the composition in an amount less than about 50% by weight, such as in an amount less than about 45% by weight, such as in an amount less than about 40% by weight, such as in an amount less than about 35% by weight, such as in an amount less than about 30% by weight.

In one embodiment, the polymer binder may comprise a starch, such as a modified starch. The starch, for instance, may be derived from corn or waxy maize. In one embodiment, the starch may comprise HI-CAP100 starch sold by National Starch and Chemical Company.

In an alternative embodiment, the polymer binder may comprise arabinogalactan. Arabinogalactan is a soluble polysaccharide that not only can serve as a polymer binder but may also provide other benefits. For instance, arabinogalactan may enhance the adaptive immune response in some circumstances. Arabinogalactan is described, for instance, in U.S. Pat. No. 8,784,844, which is incorporated herein by reference.

In one embodiment, larch arabinogalactan may be used as the polymer binder. Larch arabinogalactan is a highly branched polysaccharide that is composed of galactose units and arabinose units in the approximate ratio of 6:1. Larch arabinogalactan is extracted from large trees. The polysaccharide has a galactan backbone with side chains of galactose and arabinose. Arabinogalactan is commercially available from Lonza Ltd.

Once the polymer binder is combined with the protein building composition such as through a spray dry process, the resulting mixture can then be combined with a stabilizer package. In one embodiment, the stabilizer package comprises oxide particles in combination with a salt of a carboxylic acid. In one particular embodiment, the stabilizer package may comprise a dry product, such as a powder or granular product that is combined with the protein building composition and polymer binder. The combination of oxide particles and a salt of a carboxylic acid have been found to provide numerous advantages and benefits when combined with the protein building composition. For instance, the stabilizer package has been found to stabilize the protein building composition and make the composition less hydroscopic. The composition is also easier to handle and, when in granular form, produces a free-flowing product.

The oxide particles that may be added to the pharmaceutical composition may comprise silica. For instance, the oxide particles may comprise precipitated silica particles. The silica particles may have a particle size (d50, laser defraction following ISO Test 13320) of less than about 55 microns, such as less than about 40 microns, such as less than about 30 microns, such as less than about 25 microns, such as less than about 20 microns, such as less than about 15 microns, such as less than about 12 microns, such as less than about 10 microns, such as less than about 8 microns, such as less than about 6 microns, such as less than about 4 microns, such as less than about 2 microns, such as less than about 1 micron. The particle size is typically greater than about 0.5 microns, such as greater than about 1 micron. The particles may have a specific surface area (ISO Test 9277) of greater than about 120 $m^2/g$, such as greater than about 130 $m^2/g$, such as greater than about 150 $m^2/g$, such as greater than about 170 $m^2/g$, such as greater than about 200 $m^2/g$, such as greater than about 220 $m^2/g$. The specific surface area is generally less than about 500 $m^2/g$. The oxide particles, such as the silica particles, can be present in the pharmaceutical composition in an amount greater than about 0.01% by weight, such as in an amount greater than about 0.05% by weight, such as in an amount greater than about 0.1% by weight. The oxide particles are generally present in an amount less than 5% by weight, such as in an amount less than about 2% by weight, such as in an amount less than about 1.5% by weight, such as in an amount less than 0.5% by weight.

In addition to the oxide particles, the stabilizer package may also include a salt of a carboxylic acid. The salt of a carboxylic acid may comprise a salt of a fatty acid. The fatty acid, for instance, may have a carbon chain length of from about 6 carbon atoms to about 40 carbon atoms, such as from about 12 carbon atoms to about 28 carbon atoms. In one embodiment, the salt of the carboxylic acid may comprise a stearate salt. The stearate salts that may be used include calcium stearate, sodium stearate, magnesium stearate, mixtures thereof, and the like. In one embodiment, the salts of the carboxylic acid may include both hydrophilic groups and hydrophobic groups. The salt of the carboxylic acid may be present in the pharmaceutical composition in an amount greater than about 0.5% by weight, such as in an amount greater than about 1% by weight, such as in an amount greater than about 1.5% by weight. The salt of the carboxylic acid is generally present in an amount less than about 5% by weight, such as in an amount less than about 4% by weight, such as in an amount less than about 3% by weight.

In addition to the polymer binder and the stabilizer package, the composition may include various other components and ingredients. In one embodiment, for instance, the composition may contain a citric acid ester, such as a citric acid ester of a mono and/or diglyceride of a fatty acid. The composition may also contain a lecithin, such as a lecithin obtained from rapeseed, sunflower, and the like. The above components can be present in the composition in relatively minor amounts, such as less than about 2% by weight, such as less than about 1.5% by weight, such as less than about 1% by weight. The above components are generally present in an amount greater than about 0.05% by weight, such as in an amount greater than about 0.1% by weight.

Once the above components are combined together to form the pharmaceutical composition, the composition can optionally be combined with a coating material. In one embodiment, for instance, the pharmaceutical composition may comprise a granular composition to which a coating material is applied that contains a fat. The coating material, for instance, may comprise a hydrogenated oil, such as hydrogenated palm oil. In one particular embodiment, the coating material may comprise hydrogenated palm oil combined with palm stearine. In one embodiment, the hydrogenated oil may be present in the pharmaceutical composition in an amount from about 5% to about 35% by weight. The palm stearine, on the other hand, may be present in the pharmaceutical composition in an amount from about 2% to about 10% by weight. When present together, the weight ratio between the hydrogenated palm oil and the palm stearine may be from about 10:1 to about 1:1, such as from about 6:1 to about 2:1. In one embodiment, the hydrogenated palm oil and the palm stearine are present at a weight ratio of about 4:1.

The present disclosure may be better understood with reference to the following examples.

Example No. 1

A randomized, double-blind, placebo-controlled study was conducted to evaluate the effects of two protein building compositions formulated according to the present disclosure on muscle protein synthesis, functional strength, lean body mass, and overall quality of life in healthy older adults.

The study was conducted with a sample size of 42 healthy older adults, with 14 subjects randomized to each study arm in a double-blind manner at a ratio of 1:1:1. Each subject was selected for compliance with the inclusion and exclusion criteria shown in Tables 1 and 2.

TABLE 1

| Inclusion Criteria For Test Subjects |
| --- |
| Healthy male or female adults, aged 55 to 70 years |
| BMI of 21 kg/m$^2$ to 33 kg/m$^2$ |
| Subjects in good physical condition such that they can perform exercise testing safely, as determined by the Qualified Investigator based on medical history, physical examination, electrocardiogram and laboratory results |
| Subjects who are sedentary and not currently engaging in any regular exercise. |
| Subjects who agree to maintain their current level of activity and current dietary habits throughout the trial period. |
| Subjects who have given voluntary, written, informed consent to participate in the study. |

TABLE 2

| Exclusion Criteria For Test Subjects |
| --- |
| Subjects who are smokers or have been a smoker within the past 1 year from screening. |
| Subjects who are pregnant or breastfeeding |
| Subjects who have experienced weight loss or gain of greater than 4.5 kg (approximately 10 lbs) within 3 months of randomization |
| Subjects diagnosed with active heart disease |
| Subjects with uncontrolled hypertension (≥140 mmHg) |
| Subjects with renal or hepatic impairment or disease |
| Subjects with any major diseases of the gastrointestinal, pulmonary or endocrine systems |
| Subjects with a history of seizures |
| Subjects with Type I and Type II Diabetes |
| Subjects with active cancer (excluding basal cell carcinoma) |
| Subjects with neurological or significant psychiatric illnesses, including Parkinson's disease and bi-polar disorder |
| Subjects with unstable thyroid disease |
| Subjects who are immuno-compromised (HIV positive, on anti-rejection medication, rheumatoid arthritis) |
| Subjects with metal fixation plates or screws from a previous surgery |
| Subjects who are taking oral anticoagulants (blood thinners) such as warfarin (Coumadin) or Dabigatran (Pradaxa) or antiplatelet agents such as Clopidogrel (Plavix) |
| Subjects who are regularly taking NSAID medications such as aspirin, must stop at least one week prior to the micro-needle muscle biopsy procedures. |
| Subjects with a known allergy to anesthetic |
| Subjects who currently experience any medical condition that interferes with the ability to undergo physical strength testing during the study |
| Subjects currently taking NHPs must have been using their current dosing regimen for at least one month prior to baseline and must maintain their current dosing regimen throughout the trial and must not begin taking any new NHPs throughout the trial. If the subject wishes to stop taking the NHP prior to beginning the trial, they must do so at least 1 week prior to randomization. |
| Subjects who use illicit drugs or have a history of alcohol or drug abuse within the past 6 months |
| Subjects who currently consume greater than 2 standard alcoholic drinks per day. |
| Subjects who have participated in a clinical research trial within 30 days prior to randomization. |
| Subjects with an allergy or sensitivity to the investigational product ingredient. |
| Subjects who are cognitively impaired and/or who are unable to give informed consent |
| Subjects who have abnormal laboratory results or any other medical or psychological condition which, in the opinion of the Qualified Investigator, may adversely affect the subject's ability to complete the study or its measures or which may pose significant risk to the subject. |

The compositions of the three nutritional supplements are shown in Table 3. Subjects received one of the three supplements based on whether they were in the Sample 1, Sample 2, or the placebo group. The Sample 1 group received 4 grams of the designated composition per day. The Sample 2 group received 8 grams of the designated composition per day. The placebo group received 3 grams of the designated composition per day. Subjects were instructed to empty the contents of the sachet of the designated composition into one bottle of orange juice and shake vigorously for 1 min, then drink the entire bottle. Each sachet for Sample 1 and Sample 2 contained 2.2 g of L-carnitine tartrate. Subjects were instructed to start taking the product the day after randomization (Day 1). The subjects continued to take the product for an 8 week period.

Subjects were asked to maintain their current physical activity levels and dietary habits throughout the trial.

TABLE 3

L-Carnitine and Placebo Supplement Compositions

| | | |
|---|---|---|
| Sample 1 | Active Ingredients<br>L-carnitine (1500 mg) | Other Ingredients<br>Maltodextrin<br>Sucrose<br>Colloidal Silicon Dioxide<br>Mixed Berry Flavor<br>Sucralose |
| Sample 2 | Active Ingredients<br>L-carnitine (1500 mg)<br>L-Leucine (2000 mg)<br>Creatine monohydrate (3000 mg)<br>Vitamin D3 (400 IU) | Other Ingredients<br>Sucrose<br>Colloidal Silicon Dioxide<br>Mixed Berry Flavor<br>Sucralose |
| Placebo | | Tartaric Acid<br>Maltodextrin<br>Sucrose<br>Colloidal Silicon Dioxide<br>Mixed Berry Flavor<br>Sucralose |

Assessments were conducted at Day 0, Day 29±3, and Day 57±3 of the study. On Day 29, subjects were contacted via phone to monitor adverse events and changes in concomitant medications as well as to foster compliance with the study dosing regimen.

Data was analyzed for the per protocol population, which consisted of all participants who consumed at least 80% of treatment or placebo doses, did not have any major protocol violations and completed all study visits and procedures connected with measurement of the primary variable. The per-protocol population contained 39 subjects, as 3 subjects were excluded from the original 42 subject population for protocol violations. For statistical analysis, within-group changes over 8 weeks of supplementation, and pre-to-post-strength testing changes, were tested for significance by the paired Student t test or the non-parametric Wilcoxon Signed-ranks test, Between-group differences in 8-week changes were tested for significance by the unpaired Student t test or the non-parametric Mann-Whitney U test. In the following tables, treatment groups with differing letter superscripts are significantly different. Probability values $P \leq 0.05$ are statistically significant.

Total lean mass was measured for each participant on Day 0 and Day 57±3 via dual-energy X-ray absorptiometry (DXA). As shown in FIG. 1 and Table 4, total lean mass was significantly increased (+1.01 kg, P=0.013) in the Sample 2 group, but not in Sample 1 (−0.03 kg, P=0.915) or the placebo (0.0 kg, P=0.986) groups.

As revealed in FIG. 2, arm lean mass significantly differed between Sample 1 and 2 (P=0.012) by the end of 8 weeks, with Sample 1 showing a slight reduction (−0.137 kg) in arm mass and Sample 2 demonstrating a minor increase (+0.135 kg) in arm mass.

FIG. 3 demonstrated that participants supplemented with Sample 2 also had enhanced leg muscle mass (+0.35 kg, P=0.005), which was not reflected in the placebo group (−0.03 kg, P=0.811). Subjects on Sample 1 did exhibit a small, but non-significant increase in leg lean mass (+0.17 kg, P=0.256) as well.

Illustrated in FIG. 4, total non-trunk lean mass increased significantly in the Sample 2 group by the end of the study (+0.48 kg, P=0.006). This change was significantly greater than the placebo group (P<0.05), which tended to lose total non-trunk lean mass (−0.10 kg, P=0.560). Sample 1 group maintained their total non-trunk lean mass for the duration of the study (+0.03 kg, P=837).

TABLE 4

DXA Lean Masses at Baseline and at End of the Study for All Participants in the PP Population (N = 39).

| | Placebo<br>Mean ± SD (n)<br>Median (Min-Max)<br>Within Group P Value[‡] | Sample 1<br>Mean ± SD (n)<br>Median (Min-Max)<br>Within Group P Value[‡] | Sample 2<br>Mean ± SD (n)<br>Median (Min-Max)<br>Within Group P Value[‡] | Between Group P Values | | | |
|---|---|---|---|---|---|---|---|
| | | | | Overall[Δ] | Placebo vs Sample 1[δ] | Placebo vs Sample 2[δ] | Sample 1 vs Sample 2[δ] |
| Total Lean Mass (kg) | | | | | | | |
| Baseline (Week 0) | 43.7 ± 9.1 (14)<br>40.8 (30.4-60.1) | 44.8 ± 8.8 (11)<br>40.5 (33-60.1) | 45.2 ± 8.6 (14)<br>42.2 (34.9-65.2) | — | — | — | — |
| Visit 3 (Week 8) | 43.7 ± 9.2 (14)<br>40.8 (29.7-60.6) | 45.0 ± 8.9 (11)<br>40.9 (33.5-61.6) | 46.2 ± 9.7 (14)<br>43 (35-68.6) | — | — | — | — |
| Change from Baseline to Week 8 | −0.00 ± 1.04 (14)<br>0.23 (−2.11-1.36)<br>p = 0.986 | 0.14 ± 1.22 (11)<br>0.48 (−1.61-1.6)<br>p = 0.716 | 1.01 ± 1.30 (14)<br>0.98 (−1.37-3.41)<br>p = 0.013 | 0.074 | 0.978 | 0.088 | 0.169 |
| Arm Lean Mass (kg) | | | | | | | |
| Baseline (Week 0) | 4.91 ± 1.47 (14)<br>4.8 (3.29-7.69) | 5.11 ± 1.72 (11)<br>4.11 (3.21-7.42) | 4.93 ± 1.43 (14)<br>4.4 (3.5-7.9) | — | — | — | — |
| Visit 3 (Week 8) | 4.84 ± 1.40 (14)<br>4.37 (3.06-7.22) | 4.99 ± 1.68 (11)<br>4.09 (3.12-7.3) | 5.07 ± 1.52 (14)<br>4.66 (3.39-7.98) | | | | |

TABLE 4-continued

DXA Lean Masses at Baseline and at End of the Study for All Participants in the PP Population (N = 39).

| | Placebo Mean ± SD (n) Median (Min-Max) Within Group P Value‡ | Sample 1 Mean ± SD (n) Median (Min-Max) Within Group P Value‡ | Sample 2 Mean ± SD (n) Median (Min-Max) Within Group P Value‡ | Between Group P Values | | | |
|---|---|---|---|---|---|---|---|
| | | | | Overall<sup>Δ</sup> | Placebo vs Sample 1<sup>δ</sup> | Placebo vs Sample 2<sup>δ</sup> | Sample 1 vs Sample 2<sup>δ</sup> |
| Change from Baseline to Week 8 | −0.071 ± 0.276 (14) 0.015 (−0.55-0.42) p = 0.351 | −0.123 ± 0.088 (11) −0.12 (−0.3--0.02) p < 0.001 | 0.135 ± 0.252 (14) 0.15 (−0.45-0.48) p = 0.067 | 0.019 | 0.863 | 0.061 | 0.026 |
| Leg Lean Mass (kg) | | | | | | | |
| Baseline (Week 0) | 14.59 ± 3.13 (14) 13.98 (10.52-20.34) | 14.30 ± 2.88 (11) 13.07 (10.91-19.02) | 14.41 ± 3.06 (14) 13.87 (11.29-20.98) | — | — | — | — |
| Visit 3 (Week 8) | 14.6 ± 3.2 (14) 13.6 (10.2-20.1) | 14.6 ± 3.0 (11) 13.1 (11.7-20.1) | 14.8 ± 3.2 (14) 14.1 (11.1-21.6) | — | — | — | — |
| Change from Baseline to Week 8 | −0.03 ± 0.46 (14) −0.05 (−0.73-0.7) p = 0.811 | 0.29 ± 0.50 (11) 0.16 (−0.49-1.05) p = 0.086 | 0.35 ± 0.39 (14) 0.38 (−0.35-0.99) p = 0.005 | 0.069 | 0.185 | 0.076 | 0.947 |
| Total Non-Trunk Lean Mass (kg) | | | | | | | |
| Baseline (Week 0) | 19.5 ± 4.5 (14) 18.4 (14.2 −27.7) | 19.4 ± 4.5 (11) 16.8 (14.2-26.4) | 19.3 ± 4.4 (14) 17.9 (14.8-28.9) | — | — | — | — |
| Visit 3 (Week 8) | 19.4 ± 4.6 (14) 17.9 (13.3-27) | 19.6 ± 4.6 (11) 16.8 (14.8-27.4) | 19.8 ± 4.7 (14) 18.4 (14.5-29.5) | — | — | — | — |
| Change from Baseline to Week 8 | −0.10 ± 0.64 (14) 0.02 (−1.2-1.12) p = 0.560 | 0.16 ± 0.51 (11) 0.14 (−0.67-0.93) p = 0.315 | 0.48 ± 0.56 (14) 0.54 (−0.48-1.22) p = 0.006 | 0.037 | 0.499 | 0.029 | 0.360 |
| Trunk Lean Mass (kg) | | | | | | | |
| Baseline (Week 0) | 23.2 ± 10.8 (14) 20.1 (13.9-58) | 23.9 ± 6.4 (11) 23.2 (16.4-39.3) | 27.6 ± 11.0 (14) 23.6 (17.5-57.4) | — | — | — | — |
| Visit 3 (Week 8) | 22.4 ± 6.2 (14) 20.2 (14-37.9) | 22.1 ± 4.0 (11) 22.2 (16.1-29.9) | 23.0 ± 4.1 (14) 22.5 (17.7-31.9) | — | — | — | — |
| Change from Baseline to Week 8 | −0.8 ± 10.1 (14) 0.1 (−30.9-19.3) p = 0.973* | −1.7 ± 5.1 (11) −0.4 (−17.1-0.6) p = 0.271* | −4.6 ± 9.9 (14) −0.2 (−28.4-1.7) p = 0.101* | 0.943* | 0.969* | 0.942* | 0.997* |

N, number;
SD, standard deviation;
Min, minimum;
Max, maximum;
kg, kilogram
<sup>Δ</sup>Between-group comparisons were made using ANCOVA.
<sup>δ</sup>Pairwise between-group comparisons were made using the Tukey procedure.
Within-group comparisons were made using the paired Student t-test.
*Logarithmic transformation was required to achieve normality.
Treatment groups with differing letter superscripts are significantly different.
Probability values P ≤ 0.05 are statistically significant.

Lower leg strength was assessed by average leg dynamometry for each participant on Day 0 and Day 57±3. As shown in FIG. 5 and Table 5, lower leg strength was significantly increased in the Sample 2 group (+1.0 kg, P=0.029). This increase in leg dynamometry corresponds with the rise in leg muscle mass (DXA scan) and was significantly different from the placebo group (P=0.012), which exhibited reduced average leg strength (−2.8 kg, P=0.061) by the end of study. Sample 1 significantly differed from the placebo group (P=0.023) and maintained their average leg strength throughout the study duration (−0.4 kg, P=0.764). Upper body strength markers, including average left and right hand, as well as average arm strength did not significantly change for any treatment group.

TABLE 5

Dynamometry Results at Baseline and at End of the Study for All Participants in the PP Population (N = 39).

| | Placebo | Sample 1 | Sample 2 | Between Group P Values | | | |
|---|---|---|---|---|---|---|---|
| | Mean ± SD (n) Median (Min-Max) Within Group P Value | Mean ± SD (n) Median (Min-Max) Within Group P Value | Mean ± SD (n) Median (Min-Max) Within Group P Value | Overall[Δ] | Placebo vs Sample 1[δ] | Placebo vs Sample 2[δ] | Sample 1 Vs Sample 2[δ] |
| Average Right Hand (kg) | | | | | | | |
| Baseline (Week 0) | 28.3 ± 10.3 (14) 27.5 (4.5-45.6) | 26.5 ± 10.3 (11) 26.3 (11.2-45.9) | 24.0 ± 9.9 (14) 26 (7.6-40.8) | — | — | — | — |
| Visit 3 (Week 8) | 28.6 ± 11.6 (14) 25.2 (3.9-49.8) | 24.9 ± 10.7 (11) 23.3 (10.3-42.3) | 25.6 ± 9.4 (14) 25.7 (10-41.1) | — | — | — | — |
| Change from Baseline to Week 8 | 0.3 ± 4.9 (14) −0.7 (−4.8-14.2) p = 0.819 | −1.5 ± 4.2 (11) 0.3 (−11.6-4.2) p = 0.257 | 1.7 ± 6.3 (14) 0.3 (−6.8 −19.5) p = 0.345 | 0.383 | 0.619 | 0.884 | 0.358 |
| Average Left Hand (kg) | | | | | | | |
| Baseline (Week 0) | 27.1 ± 11.2 (14) 26.8 (4.7-48.2) | 26.2 ± 12.1 (11) 24.8 (9.4-52.1) | 23.8 ± 10.6 (14) 25.3 (8.3-41.5) | — | — | — | — |
| Visit 3 (Week 8) | 27.3 ± 10.2 (14) 26.2 (5.1-42) | 25.8 ± 12.1 (11) 26.1 (9.8-50.9) | 26.2± 9.6 (14) 25.3 (10.1-40.8) | — | — | — | — |
| Change from Baseline to Week 8 | 0.2 ± 4.3 (14) 1.1 (−7.6-7.7) p = 0.869 | −0.3 ± 4.1 (11) −0.6 (−10.6-4.1) p = 0.791 | 2.3 ± 4.9 (14) 1.9 (−3.3-16.2) p = 0.095 | 0.363 | 0.921 | 0.552 | 0.366 |
| Average Arm (kg) | | | | | | | |
| Baseline (Week 0) | 27.7 ± 10.7 (14) 27.1 (4.6-46.9) | 26.3 ± 11.2 (11) 25.7 (10.3-49) | 23.9 ± 10.1 (14) 26.1 (7.9-41.1) | — | — | — | — |
| Visit 3 (Week 8) | 27.9 ± 10.8 (14) 25.3 (4.5-45.9) | 25.4 ± 11.3 (11) 24.1 (10-46.6) | 25.9 ± 9.3 (14) 25.6 (10-39.9) | — | — | — | — |
| Change from Baseline to Week 8 | 0.2 ± 4.2 (14) 0 (−5.5-10) p = 0.828 | −0.9 ± 4.0 (11) −0.1 (−11.1-4.2) p = 0.455 | 2.0 ± 5.3 (14) 0.9 (−3.8-17.8) p = 0.186 | 0.354 | 0.744 | 0.725 | 0.322 |
| Average Leg (kg) | | | | | | | |
| Baseline (Week 0) | 13.5 ± 6.4 (14) 12.4 (4.5-24.5) | 15.7 ± 5.1 (11) 16.8 (6.9-23.6) | 12.3 ± 7.2 (14) 10.5 (4.5-24.6) | — | — | — | — |
| Visit 3 (Week 8) | 10.7 ± 3.6 (14) 9.9 (6.5-19.3) | 15.7 ± 5.1 (11) 15.1 (9.4-26.6) | 13.4 ± 6.2 (14) 13.1 (6-23.3) | — | — | — | — |
| Change from Baseline to Week 8 | −2.8 ± 4.8 (14)[a] −2 (−14.8-2.4) p = 0.061[†] | 0.0 ± 4.5 (11)[b] 1.1 (−8.6-5.2) p = 0.952[†] | 1.0 ± 2.0 (14)[b] 1.2 (−3.8-4.5) p = 0.029[†] | 0.006[†] | 0.016[†] | 0.014[†] | 0.988[†] |

N, number;
SD, standard deviation;
Min, minimum;
Max, maximum;
kg, kilogram
[Δ]Between-group comparisons were made using ANCOVA.
[δ]Pairwise between-group comparisons were made using the Tukey procedure.
Within-group comparisons were made using the paired Student t-test.
[†]Square root transformation required to achieve normality.
Treatment groups with differing letter superscripts are significantly different.
Probability values $P \leq 0.05$ are statistically significant.

The participants completed the six minute walk test on Day 0 and Day 57±3. Table 6 shows that participants taking placebo had a significant reduction in their out of breath score after walking at the end of study relative to baseline (−0.43, P<0.05). There were no notable changes in the total meters walked, out of breath score before walking, and fatigue score before/after walking in all treatment groups.

TABLE 6

Six Minute Walk Test at Baseline and at End of the Study for All Participants in the PP Population (N = 39).

| | Placebo | Sample 1 | Sample 2 | Between Group P Values | | | |
|---|---|---|---|---|---|---|---|
| | Mean ± SD (n) Median (Min-Max) Within Group P Value | Mean ± SD (n) Median (Min-Max) Within Group P Value | Mean ± SD (n) Median (Min-Max) Within Group P Value | Overall[Δ] | Placebo vs Sample 1[δ] | Placebo vs Sample 2[δ] | Sample 1 Vs Sample 2[δ] |
| Meters Walked in Six Minutes (m) | | | | | | | |
| Baseline (Week 0) | 526 ± 80 (14) 542 (336-633) | 458 ± 127 (11) 442 (239-695) | 432 ± 109 (14) 460 (220-540) | — | — | — | — |
| Visit 3 (Week 8) | 530 ± 100 (14) 560 (220-627) | 444 ± 119 (11) 497 (220-560) | 462 ± 113 (14) 490 (238-600) | — | — | — | — |
| Change from Baseline to Week 8 | 3 ± 69 (14) −3 (−116-140) p = 0.704[†] | −14 ± 107 (11) −8 (−222-135) p = 0.617[†] | 30 ± 70 (14) 27 (−120-138) p = 0.126[†] | 0.310[†] | 0.326[†] | 0.961[†] | 0.449[†] |
| Out of Breath Score Before Walking | | | | | | | |
| Baseline (Week 0) | 0.00 ± 0.00 (14) 0 (0-0) | 0.09 ± 0.30 (11) 0 (0-1) | 0.21 ± 0.80 (14) 0 (0-3) | — | — | — | — |
| Visit 3 (Week 8) | 0.000 ± 0.000 (14) 0 (0-0) | 0.045 ± 0.151 (11) 0 (0-0.5) | 0.036 ± 0.134 (14) 0 (0-0.5) | — | — | — | — |
| Change from Baseline to Week 8 | 0.00 ± 0.00 (14) 0 (0-0) p = 1.000[‡] | −0.05 ± 0.15 (11) 0 (−0.5-0) p = 1.000[‡] | −0.18 ± 0.67 (14) 0 (−2.5-0) p = 1.000[‡] | 0.555[□] | 0.93[□] | 0.94[□] | 1.00[□] |
| Out of Breath Score After Walking | | | | | | | |
| Baseline (Week 0) | 1.04 ± 0.91 (14) 1 (0-3) | 0.55 ± 0.79 (11) 0 (0-2) | 1.07 ± 2.16 (14) 0 (0-7) | — | — | — | — |
| Visit 3 (Week 8) | 0.61 ± 0.56 (14) 0.5 (0-2) | 0.41 ± 0.58 (11) 0.5 (0-2) | 1.00 ± 1.79 (14) 0 (0-5) | — | — | — | — |
| Change from Baseline to Week 8 | −0.43 ± 0.70 (14) −0.5 (−2-0.5) p = 0.044[‡] | −0.14 ± 0.64 (11) 0 (−1.5-0.5) p = 0.590[‡] | −0.07 ± 0.87 (14) 0 (−2-2) p = 0.730[‡] | 0.347[□] | 0.45[□] | 0.46[□] | 1.00[□] |
| Change in Out of Breath Score After Waking | | | | | | | |
| Baseline (Week 0) | 1.04 ± 0.91 (14) 1 (0-3) | 0.45 ± 0.65 (11) 0 (0-2) | 0.86 ± 1.60 (14) 0 (0-5) | — | — | — | — |
| Visit 3 (Week 8) | 0.61 ± 0.56 (14) 0.5 (0-2) | 0.36 ± 0.45 (11) 0.5 (0-1.5) | 0.96 ± 1.70 (14) 0 (0-5) | — | — | — | — |
| Change from Baseline to Week 8 | −0.43 ± 0.70 (14) −0.5 (−2-0.5) p = 0.044[‡] | −0.09 ± 0.66 (11) 0 (−1.5 -0.5) p = 0.792[‡] | 0.11 ± 0.68 (14) 0 (−1-2) p = 0.792[‡] | 0.155[□] | 0.33[□] | 0.20[□] | 0.98[□] |
| Fatigue Score Before Walking | | | | | | | |
| Baseline (Week 0) | 0.54 ± 0.93 (14) 0 (0-3) | 0.50 ± 1.02 (11) 0 (0-3) | 0.21 ± 0.54 (14) 0 (0-2) | — | — | — | — |
| Visit 3 (Week 8) | 0.39 ± 0.92 (14) 0 (0-3) | 0.18 ± 0.60 (11) 0 (0-2) | 0.25 ± 0.80 (14) 0 (0-3) | — | — | — | — |
| Change from Baseline to Week 8 | −0.14 ± 0.57 (14) 0 (−1-1) p = 0.387[‡] | −0.32 ± 1.27 (11) 0 (−3-2) p = 0.461[‡] | 0.04 ± 0.95 (14) 0 (−1.5-3) p = 0.854[‡] | 0.929[□] | 0.98[□] | 0.99[□] | 0.94[□] |
| Fatigue Score After Walking | | | | | | | |
| Baseline (Week 0) | 0.82 ± 0.91 (14) 0.5 (0-3) | 0.82 ± 1.03 (11) 0.5 (0-3) | 0.64 ± 1.36 (14) 0 (0-5) | — | — | — | — |

TABLE 6-continued

Six Minute Walk Test at Baseline and at End of the Study for All Participants in the PP Population (N = 39).

| | Placebo | Sample 1 | Sample 2 | Between Group P Values | | | |
|---|---|---|---|---|---|---|---|
| | Mean ± SD (n) Median (Min-Max) Within Group P Value | Mean ± SD (n) Median (Min-Max) Within Group P Value | Mean ± SD (n) Median (Min-Max) Within Group P Value | Overall[A] | Placebo vs Sample 1[δ] | Placebo vs Sample 2[δ] | Sample 1 Vs Sample 2[δ] |
| Visit 3 (Week 8) | 0.61 ± 0.86 (14) 0.5 (0-3) | 0.45 ± 0.88 (11) 0 (0-3) | 0.93 ± 1.25 (14) 0.25 (0-3) | — | — | — | — |
| Change from Baseline to Week 8 | −0.21 ± 0.64 (14) −0.25 (−1.5-1) p = 0.266[‡] | −0.36 ± 1.38 (11) 0 (−3-2.5) p = 0.348[‡] | 0.29 ± 1.17 (14) 0 (−2-3) p = 0.394[‡] | 0.254[□] | 0.98[□] | 0.38[□] | 0.33[□] |
| Change in Fatigue Score After Walking | | | | | | | |
| Baseline (Week 0) | 0.29 ± 0.64 (14) 0.25 (−1-2) | 0.32 ± 0.64 (11) 0 (−0.5-2) | 0.43 ± 1.33 (14) 0 (0-5) | — | — | — | — |
| Visit 3 (Week 8) | 0.21 ± 0.26 (14) 0 (0-0.5) | 0.27 ± 0.34 (11) 0 (0-1) | 0.68 ± 1.05 (14) 0 (0-3) | — | — | — | — |
| Change from Baseline to Week 8 | −0.07 ± 0.68 (14) 0 (−1.5-1.5) p = 0.660[‡] | −0.05 ± 0.65 (11) 0 (−1.5-1) p = 1.000[‡] | 0.25 ± 1.03 (14) 0 (−2-2.5) p = 0.341[‡] | 0.437[□] | 0.92[□] | 0.47[□] | 0.75[□] |

N, number;
SD, standard deviation;
Min, minimum;
Max, maximum
[A]Between-group comparisons were made using ANCOVA.
[δ]Pairwise between-group comparisons were made using the Tukey procedure.
Within-group comparisons were made using the paired Student t-test.
[†]Square root transformation required to achieve normality.
[□]Between-group comparisons were made using the Kruskal Wallis test.
[‡]Within-group comparisons were made using the signed-rank test.
Probability values P ≤ 0.05 are statistically significant.

Quality of life was determined by the participants' responses to the RAND SF-36 questionnaire on Day 0 and Day 57±3 shown in Table 7. The SF-36 questionnaire was developed at RAND as part of the Medical Outcomes Study. The Sample 1 group showed a trend towards increasing their energy/fatigue ratio (+6.1, P=0.073) by the end of the study relative to baseline. All other quality of life measures, including physical functioning, role functioning (physical or emotional), emotional well-being, social functioning, pain, and general health were not significantly changed by any intervention.

TABLE 7

SF-36 Questionnaire Results at Baseline and at End of the Study for All Participants in the PP Population (N = 39).

| | Placebo Mean ± SD (n) Median (Min-Max) Within Group P Value[‡] | Sample 1 Mean ± SD (n) Median (Min-Max) Within Group P Value[‡] | Sample 2 Mean ± SD (n) Median (Min-Max) Within Group P Value[‡] | P Values[□] | | | |
|---|---|---|---|---|---|---|---|
| | | | | Overall[□] | Placebo vs Sample 1[δ] | Placebo vs Sample 2[δ] | Sample 1 Vs Sample 2[δ] |
| Physical Functioning | | | | | | | |
| Baseline (Week 0) | 88.6 ± 16.2 (14) 97.5 (50-100) | 86.4 ± 15.2 (11) 95 (60-100) | 81.1 ± 19.0 (14) 90 (35-100) | — | — | — | — |
| Visit 3 (Week 8) | 88.6 ± 14.6 (14) 97.5 (65-100) | 85.9 ± 12.0 (11) 85 (60-100) | 80.7 ± 13.4 (14) 82.5 (50-100) | — | — | — | — |
| Change from Baseline to Week 8 | 0.0 ± 8.3 (14) 0 (−15-20) p = 1.000 | −0.5 ± 7.2 (11) 0 (−15-15) p = 0.890 | −0.4 ± 14.9 (14) −2.5 (−25-35) p = 0.720 | 0.713 | 0.78 | 0.21 | 0.63 |
| Role Functioning/Physical | | | | | | | |
| Baseline (Week 0) | 90.2 ± 19.7 (14) 100 (50-100) | 97.7 ± 5.1 (11) 100 (87.5-100) | 90.2 ± 17.1 (14) 100 (50-100) | — | — | — | — |
| Visit 3 | 93.8 ± 12.7 (14) | 95.5 ± 11.6 (11) | 92.9 ± 16.0 (14) | — | — | — | — |

TABLE 7-continued

SF-36 Questionnaire Results at Baseline and at End of the Study for All Participants in the PP Population (N = 39).

| | Placebo Mean ± SD (n) Median (Min-Max) Within Group P Value‡ | Sample 1 Mean ± SD (n) Median (Min-Max) Within Group P Value‡ | Sample 2 Mean ± SD (n) Median (Min-Max) Within Group P Value‡ | P Values□ | | | |
|---|---|---|---|---|---|---|---|
| | | | | Overall□ | Placebo vs Sample 1δ | Placebo vs Sample 2δ | Sample 1 Vs Sample 2δ |
| (Week 8) | 100 (62.5-100) | 100 (62.5-100) | 100 (50-100) | | | | |
| Change from Baseline to Week 8 | 3.6 ± 19.9 (14) 0 (−25-50) p = 0.588 | −2.3 ± 7.5 (11) 0 (−25-0) p = 1.000 | 2.7 ± 25.6 (14) 0 (−50-50) p = 0.833 | 0.596 | 0.99 | 1.00 | 0.98 |
| | | | Role Functioning/Emotional | | | | |
| Baseline (Week 0) | 96.4 ± 13.4 (14) 100 (50-100) | 100.0 ± 0.0 (11) 100 (100-100) | 97.6 ± 6.1 (14) 100 (83.3-100) | — | — | — | — |
| Visit 3 (Week 8) | 100.0 ± 0.0 (14) 100 (100-100) | 93.9 ± 13.5 (11) 100 (66.7-100) | 95.2 ± 12.1 (14) 100 (66.7-100) | — | — | — | — |
| Change from Baseline to Week 8 | 3.6 ± 13.4 (14) 0 (0-50) p = 1.000 | −6.1 ± 13.5 (11) 0 (−33.3-0) p = 0.346 | −2.4-14.4 (14) 0 (−33.3-16.7) p = 0.577 | 0.319 | 0.72 | 0.79 | 0.99 |
| | | | Energy/Fatigue | | | | |
| Baseline (Week 0) | 68.9 ± 21.0 (14) 72.5 (25-90) | 68.2 ± 17.4 (11) 70 (35-90) | 58.2 ± 20.1 (14) 60 (10-80) | — | — | — | — |
| Visit 3 (Week 8) | 68.6 ± 16.5 (14) 65 (35-100) | 77.3 ± 11.7 (11) 80 (60-100) | 57.5 ± 19.3 (14) 60 (20-85) | — | — | — | — |
| Change from Baseline Week 8 | −0.4 ± 19.6 (14)$^{a,b}$ 0 (−40-45) p = 0.780 | 9.1 ± 10.0 (11)$^{b}$ 10 (−5-25) p = 0.025 | −0.7 ± 15.8 (14)$^{a}$ 0 (−45-15) p = 0.691 | 0.135 | 0.419 | 0.341 | 0.027 |
| | | | Emotional Well-Being | | | | |
| Baseline (Week 0) | 84.9 ± 15.2 (14) 88 (40-100) | 81.5 ± 7.4 (11) 88 (76-100) | 76.3 ± 14.2 (14) 82 (48-96) | — | — | — | — |
| Visit 3 (Week 8) | 84.3 ± 12.8 (14) 86 (52-100) | 87.3 ± 12.2 (11) 92 (60-100) | 81.1 ± 10.2 (14) 84 (60-92) | — | — | — | — |
| Change from Baseline to Week 8 | −0.6 ± 13.8 (14) 0 (−32-36) p = 0.670 | 0.7 ± 10.1 (11) 4 (−24-12) p = 0.509 | 4.9 ± 12.8 (14) 4 (−12-28) p = 0.261 | 0.432 | 0.70 | 0.54 | 0.17 |
| | | | Social Functioning | | | | |
| Baseline (Week 0) | 51.8 ± 4.5 (14) 50 (50-62.5) | 50.0 ± 5.6 (11) 50 (37.5-62.5) | 48.2 ± 8.3 (14) 50 (25-62.5) | — | — | — | — |
| Visit 3 (Week 8) | 50.0 ± 0.0 (14) 50 (50-50) | 52.3 ± 9.4 (11) 50 (37.5-75) | 56.2 ± 19.5 (14) 50 (25-100) | — | — | — | — |
| Change from Baseline to Week 8 | −1.8 ± 4.5 (14) 0 (−12.5-0) p = 0.346 | 2.3 ± 10.9 (11) 0 (−12.5-25) p = 0.572 | 8.0 ± 20.0 (14) 0 (−12.5-50) p = 0.202 | 0.368 | 0.93 | 0.78 | 0.96 |
| | | | Pain | | | | |
| Baseline (Week 0) | 84.1 ± 18.3 (14) 90 (45-100) | 83.4 ± 12.3 (11) 80 (57.5-100) | 77.7 ± 15.1 (14) 78.8 (42.5-100) | — | — | — | — |
| Visit 3 (Week 8) | 84.8 ± 14.6 (14) 90 (67.5-100) | 83.0 ± 15.4 (11) 90 (57.5-100) | 78 ± 20.6 (14) 85 (35-100) | — | — | — | — |
| Change from Baseline to Week 8 | 0.7 ± 11.0 (14) 0 (−12.5-22.5) p = 1.000 | −0.5 ± 13.0 (11) 0 (−22.5-12.5) p = 1.000 | 0.4 ± 23.3 (14) −5 (−32.5-57.5) p = 0.944 | 0.900 | 0.90 | 0.66 | 0.92 |
| | | | General Health | | | | |
| Baseline (Week 0) | 85.4 ± 14.3 (14) 90 (55-100) | 85.9 ± 14.3 (11) 90 (50-100) | 75.7 ± 16.9 (14) 82.5 (40-95) | — | — | — | — |
| Visit 3 (Week 8) | 83.2 ± 12.3 (14) 80 (60-100) | 86.0 ± 8.2 (11) 85 (70-100) | 77.5 ± 13.7 (14) 80 (55-100) | — | — | — | — |
| Change from Baseline to Week 8 | −2.1 ± 11.4 (14) 0 (−30-10) p = 0.892 | 0.1 ± 12.2 (11) 0 (−15-31.2) p = 0.733 | 1.8 ± 11.9 (14) −2.5 (−15-30) p = 0.662 | 0.930 | 0.78 | 0.59 | 0.25 |

N, number;
SD, standard deviation;
Min, minimum;
Max; maximum
□Between-group comparisons were made using the Kruskal Wallis test.
δPairwise between-group comparisons were made using the Tukey procedure.
†Within-group comparisons were made using the paired Student t-test.
Probability values P ≤ 0.05 are statistically significant.

For mRNA analysis, muscle biopsies were taken from participants (n=38) at Day 0 and at Day 57±3 to evaluate the effect of Sample 1 and 2 or placebo on mRNA expression levels within the Ubiquitin-proteasome pathway, growth factor/protein signaling, and pro-inflammatory signaling pathways. mRNA was isolated from muscle tissue collected at baseline and end-of-study. From the mRNA, cDNA was synthesis and analyzed using RT-PCR techniques. Anabolic/protein synthesis signaling genes (androgen receptor, insulin receptor, IGF-1 & IGF-1 receptor), catabolic/protein degradation signaling genes (atrogin-1 & MuFR1) and cytokines/cytokine receptors (IL-6, IL-6 receptor, TNFα, TNFrSF1A, TNFrSF1B) genes were assayed along with GAPDH as the endogenous control. The mRNA expression for the muscle biopsies collected suggests that the Samples affect both the anabolic and catabolic pathways.

For the growth factor/protein signaling genes, Table 8 reveals that there were no significant between group differences observed; however, there was a trend for both Carnitine groups to have greater transcription of these genes compared to placebo.

The subject number (N=38) for Table 8 is reflected by the processing and isolation of mRNA from subjects' muscle biopsies taken on Day 0 and Day 57±3. Baseline and end of study muscle samples were required for this analysis (to see relative changes in the requested markers) and some of the subjects did not have enough skeletal muscle to yield the amount of mRNA required to run the molecular analysis.

TABLE 8

Relative Changes in Quantity of Gene Transcription (mRNA) from Baseline to End of the Study for All Participants in the PP Population (N = 38).

| | Placebo | Sample 1 | Sample 2 | P Value□ | | | |
|---|---|---|---|---|---|---|---|
| | Mean ± SD (n) Median (Min-Max) Within Group P Value | Mean ± SD (n) Median (Min-Max) Within Group P Value | Mean ± SD (n) Median (Min-Max) Within Group P Value | Overall□ | Placebo vs Sample 1^δ | Placebo vs Sample 2^δ | Sample 1 Vs Sample 2^δ |
| Androgen Receptor | | | | | | | |
| Relative Quantity change in Gene Transcription (normalized to GAPDH) Baseline compared to End of Study | 0.93 ± 0.43 (14) 0.82 (0.47-1.67) p = 0.192* | 0.94 ± 0.37 (11) 1.01 (0.24-1.41) p = 0.335* | 1.10 ± 0.42 (13) 1.08 (0.61-2.26) p = 0.703* | 0.421* | 0.529* | 0.999* | 0.459* |
| Atrogin-1 | | | | | | | |
| Relative Quantity change in Gene Transcription (normalized to GAPDH) Baseline compared to End of Study | 0.98 ± 0.44 (14) 0.94 (0.38-1.68) p = 0.375* | 1.51 ± 0.61 (11) 1.25 (0.97-2.68) p = 0.013* | 1.25 ± 0.46 (13) 1.1 (0.57-2.17) p = 0.142* | 0.030* | 0.545* | 0.025* | 0.205* |
| Insulin-like Growth Factor-1 | | | | | | | |
| Relative Quantity change in Gene Transcription (normalized to GAPDH) Baseline compared to End of Study | 0.52 ± 0.28 (14) 0.52 (0.14-1.23) p < 0.001* | 0.74 ± 0.53 (11) 0.62 (0.04-1.52) p = 0.070* | 1.04 ± 0.72 (13) 0.86 (0.19-2.82) p = 0.404* | 0.122* | 0.223* | 0.990* | 0.143* |
| Insulin-like Growth Factor-1 Receptor | | | | | | | |
| Relative Quantity change in Gene Transcription (normalized to GAPDH) Baseline compared to End of Study | 1.05 ± 0.65 (14) 0.99 (0.29-2.99) p = 0.515* | 1.37 ± 1.21 (11) 1.21 (0.11-4.51) p = 0.817* | 1.41 ± 0.86 (13) 1.13 (0.3-3.03) p = 0.422* | 0.647* | 0.745* | 0.996* | 0.663* |
| IL-6 | | | | | | | |
| Relative Quantity change in Gene Transcription (normalized to GAPDH) | 0.56 ± 0.37 (14) 0.57 (0.05-1.3) p = 0.005* | 1.64 ± 2.09 (11) 0.77 (0.03-7.08) p = 0.460* | 1.06 ± 0.69 (13) 0.8 (0.22-2.47) p = 0.473* | 0.194* | 0.870* | 0.453* | 0.183* |

TABLE 8-continued

Relative Changes in Quantity of Gene Transcription (mRNA) from Baseline to End of the Study for All Participants in the PP Population (N = 38).

| | Placebo | Sample 1 | Sample 2 | P Value[□] | | | |
|---|---|---|---|---|---|---|---|
| | Mean ± SD (n) Median (Min-Max) Within Group P Value | Mean ± SD (n) Median (Min-Max) Within Group P Value | Mean ± SD (n) Median (Min-Max) Within Group P Value | Overall[□] | Placebo vs Sample 1[δ] | Placebo vs Sample 2[δ] | Sample 1 Vs Sample 2[δ] |
| Baseline compared to End of Study | | | | | | | |
| | | | IL-6 Receptor | | | | |
| Relative Quantity change in Gene Transcription (normalized to GAPDH) Baseline compared to End of Study | 1.06 ± 1.07 (14) 0.74 (0.27-4.28) p = 0.249* | 1.29 ± 0.88 (11) 1.17 (0.31-3.3) p = 0.885* | 1.28 ± 0.68 (13) 1.2 (0.39-2.84) p = 0.455* | 0.371* | 0.949* | 0.584* | 0.368* |
| | | | Insulin Receptor | | | | |
| Relative Quantity change in Gene Transcription (normalized to GAPDH) Baseline compared to End of Study | 0.97 ± 0.58 (14) 1.02 (0.1-2.29) p = 0.235* | 1.26 ± 1.36 (11) 0.91 (0.22-4.96) p = 0.556* | 1.18 ± 0.83 (13) 0.92 (0.09-3.49) p = 0.744* | 0.813* | 0.966* | 0.933* | 0.799* |
| | | | MuRF1 | | | | |
| Relative Quantity change in Gene Transcription (normalized to GAPDH) Baseline compared to End of Study | 1.23 ± 0.76 (14) 1.02 (0.48-3.24) p = 0.679* | 2.00 ± 1.27 (11) 1.8 (0.9-5.44) p = 0.005* | 1.40 ± 1.10 (13) 1.2 (0.37-4.68) p = 0.503* | 0.092* | 0.178* | 0.100* | 0.957* |
| | | | TNF-α | | | | |
| Relative Quantity change in Gene Transcription (normalized to GAPDH) Baseline compared to End of Study | 0.43 ± 0.37 (14) 0.32 (0.02-1.28) p = 0.001* | 0.76 ± 1.13 (11) 0.48 (0.02-3.99) p = 0.033* | 1.13 ± 1.17 (13) 0.57 (0.28-4.44) p = 0.320* | 0.054* | 0.188* | 0.873* | 0.053* |
| | | | TNF Receptor Superfamily 1A | | | | |
| Relative Quantity change in Gene Transcription (normalized to GAPDH) Baseline compared to End of Study | 0.61 ± 0.31 (14) 0.57 (0.17-1.15) p = 0.001* | 0.83 ± 0.54 (11) 0.74 (0.18-1.91) p = 0.097* | 1.00 ± 0.61 (13) 0.86 (0.35-2.67) p = 0.385* | 0.145* | 0.501* | 0.722* | 0.124* |
| | | | TNF Receptor Superfamily 1B | | | | |
| Relative Quantity change in Gene Transcription (normalized to GAPDH) | 0.67 ± 0.38 (14) 0.58 (0.18-1.44) p = 0.004* | 0.75 ± 0.58 (11) 0.58 (0.09-1.92) p = 0.056* | 1.04 ± 0.70 (13) 0.93 (0.21-3.1) p = 0.432* | 0.217* | 0.237* | 0.936* | 0.353* |

TABLE 8-continued

Relative Changes in Quantity of Gene Transcription (mRNA) from Baseline to
End of the Study for All Participants in the PP Population (N = 38).

| | Placebo | Sample 1 | Sample 2 | P Value[a] | | | |
|---|---|---|---|---|---|---|---|
| | Mean ± SD (n)<br>Median (Min-Max)<br>Within Group P<br>Value | Mean ± SD (n)<br>Median (Min-Max)<br>Within Group P<br>Value | Mean ± SD (n)<br>Median (Min-Max)<br>Within Group P<br>Value | Overall[a] | Placebo<br>vs Sample<br>1[b] | Placebo<br>vs<br>Sample<br>2[b] | Sample 1<br>Vs Sample<br>2[b] |
| Baseline<br>compared to<br>End of Study | | | | | | | |

N, number;
SD, standard deviation;
Min, minimum;
Max, maximum
[A]Between-group comparisons were made using ANCOVA.
[b]Pairwise between-group comparisons were made using the Tukey procedure.
Within-group comparisons were made using the paired Student t-test.
Within-group comparisons were made using the paired Student t-test.
Probability values P ≤ 0.05 are statistically significant.

The muscle biopsies taken on Day 0 and Day 57±3 from participants (n=33) were used to evaluate the effect of Sample 1 and 2 or placebo on protein expression/activity of the mTOR/S6K/4EBP1 protein synthesis and NFκβ (p65/p50) pro-inflammatory signaling pathways. Protein was isolated from muscle tissue collected at baseline and end-of-study, when pre- and post-exercise biopsies were collected. Post-exercise muscle biopsies were obtained approximately 1 h following the pre-exercise biopsies. Western blotting was done with equal concentrations (40 μg) of protein separated on 8-12% SDS-PAGE gels, which were then transferred onto nitrocellulose membranes, and immune-labeled with antibodies specific to each protein of interest. Detection of these antibodies was done using enhanced chemiluminescence (ECL).

As shown in Table 9, there were notable changes in the muscle protein levels of participants taking Sample 1 and Sample 2 from week 0 (baseline) to week 8 (end of study) pre-exercise. In Table 9, in order to minimize variability between runs, the areas under of the curve were standardized relative to the micrograms of protein.

FIGS. 6-9 illustrate changes in mTOR expression from baseline to week 8 in each treatment group. As seen in Table 9 and FIG. 9, within group, participants on Sample 2 showed a significant 81% increase in total mTOR expression (p=0.017) at week 8—pre-exercise relative to baseline mTOR levels.

FIGS. 14-17 illustrate changes in Phospho-4EBP1 and Total-4EBP1 from baseline to week 8 in each treatment group. As shown in Table 9 and FIG. 15, Sample 2 had a trend towards a 24% reduction in the phosphorylation of 4EBP-1 protein (p=0.057) at week 8—pre-exercise compared to week 0.

FIGS. 18-21 illustrate changes in Phospho-P65 and Total-P65 from baseline to week 8 in each treatment group. As seen in Table 9 and FIG. 22, the Sample 1 group showed a significant within group decrease of 38% for p65 phosphorylation of the NF-κβ complex (p=0.021) when comparing week 0 to week 8—pre-exercise. As shown in FIG. 21, there was a trend towards the Sample 1 group having a significantly reduced amount of total p65 expression compared to the placebo group when comparing week 0 to week 8—pre-exercise (p=0.087).

As shown in Table 9 and FIG. 6, there were also significant within group changes in muscle protein levels of participants taking Sample 1 and Sample 2 from week 0 (baseline) to week 8 (end of study) post-exercise. As illustrated in FIGS. 6-9, phosphorylation of mTOR was significantly increased by 41% (p=0.015) in the Sample 1 group and reduced by 35% (p=0.051) in the Sample 2 group. However, as FIG. 9 shows, total mTOR expression was increased by 56% (p=0.058) in the Sample 2 group, which was borderline significant and may compensate for the decrease in its phosphorylation for this group at week 8—post-exercise relative to baseline. As seen in FIG. 7, between groups, there was a significant difference between the Sample 1 and Sample 2 groups when comparing the changes from week 0 to week 8—post-exercise of phospho-mTOR (p=0.016).

FIGS. 10-13 illustrate changes in Phospho-S6K and Total-S6K from baseline to week 8 in each treatment group. As seen in FIG. 11, S6K phosphorylation was significantly decreased by 36% (p=0.019) in the Sample 1 group when comparing week 0 to week 8—post-exercise. On the other hand, as shown in FIG. 13, total S6K protein expression was significantly increased by 101% (p=0.038) in the Sample 1 group when comparing week 0 to week 8—post-exercise, and trended towards a significant increase of 47% in the Sample 2 group (p=0.098) as well.

As illustrated in FIGS. 14 and 15, the phosphorylation of 4EBP-1 was significantly decreased by 56% (p=0.04) and 38% (p=0.019), respectively in Sample 1 and Sample 2 groups when comparing within group changes at week 0 to week 8—post-exercise.

As shown in FIG. 19, phosphorylation of the p65 subunit of NF-κβ was significantly reduced by 56% (p=0.017) in the Sample 1 group at week 8—post-exercise relative to baseline.

Figure 25:
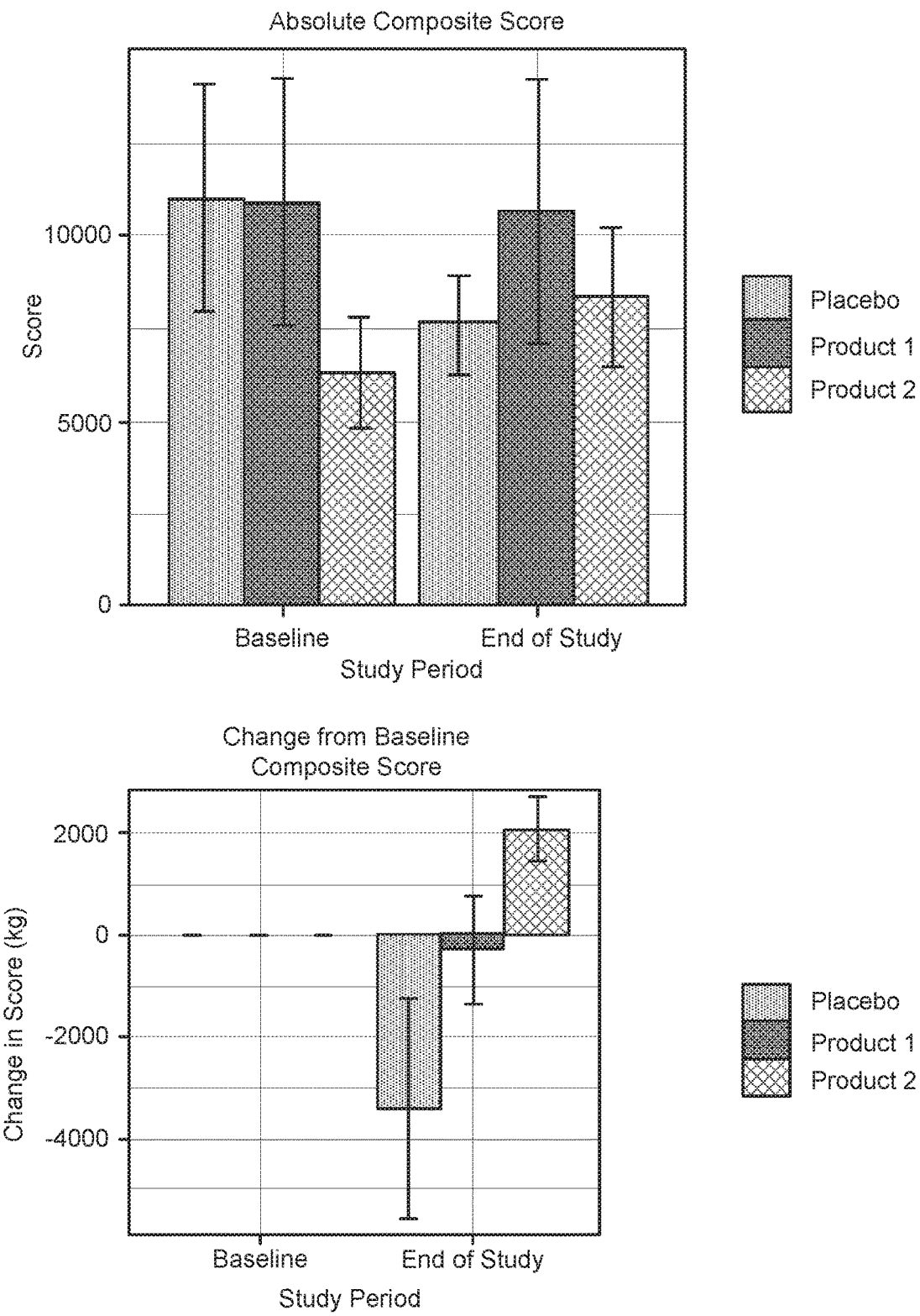
FIG. 25 shows results obtained by the procedure described in Example 1.

FIGS. 22 and 23 illustrate changes in Total-P50 from baseline to week 8 in each treatment group. As seen in FIGS. 25 and 26, there were no significant changes in total p50 expression from baseline to week 8 in any of the treatment groups.

Figure 24:
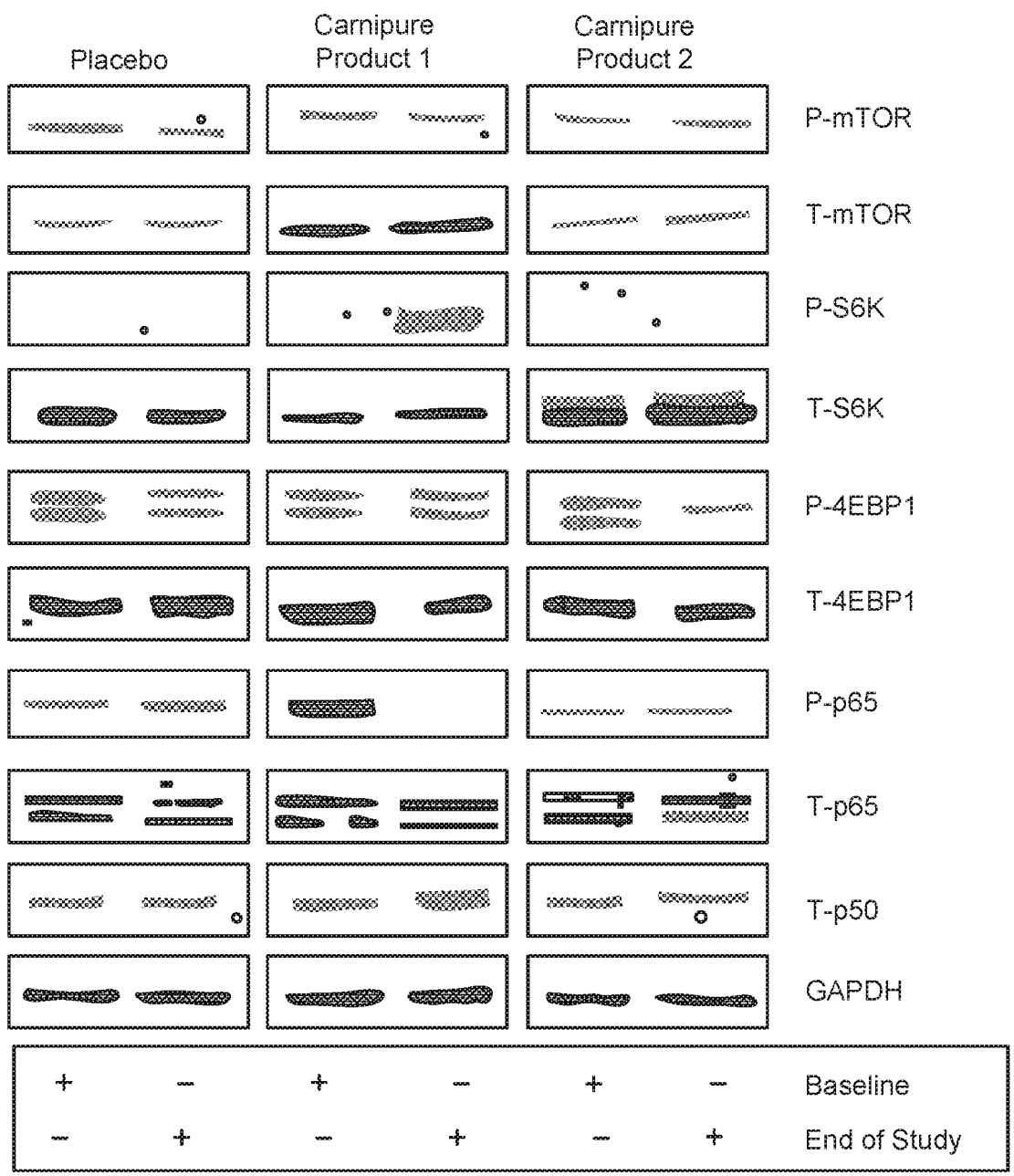
FIG. 24 shows results obtained by the procedure described in Example 1.

In FIG. 24, a representative immuno-blot for each indicated protein is shown for each treatment group (at baseline vs. end of study, 8 weeks). GAPDH was used as an internal loading control. In FIG. 14, T=total and P=phospho antibodies.

The subject number (N=33) for Table 9 is reflected by the processing and isolation of protein from subjects muscle biopsies. Baseline and end of study muscle samples were required for this analysis (to see relative changes in the requested markers) and some of the subjects did not have enough skeletal muscle to yield the amount of protein required to run the molecular analysis.

TABLE 9

Quantity of Proteins at Week 0 and Pre and Post Exercise at Week 8 for All Participants in the PP Population (N = 33).

| | Placebo Mean ± SD (n) Median (Min-Max) Within Group P Value | Carnipure Product 1 Mean ± SD (n) Median (Min-Max) Within Group P Value | Carnipure Product 2 Mean ± SD (n) Median (Min-Max) Within Group P Value | P Value[a] | | | |
|---|---|---|---|---|---|---|---|
| | | | | Overall[A] | Placebo vs Carnipure Product 1[δ] | Placebo vs Carnipure Product 2[δ] | Carnipure Product 1 vs Carnipure Product 2[δ] |
| AUC of Phospho-mTOR per Microgram Protein (×10$^1$) | | | | | | | |
| Week 0 Baseline Pre-Exercise | 8.5 ± 4.4 (10) 6.8 (2.4-15.9) | 6.8 ± 4.5 (11) 4.5 (2.3-17) | 7.6 ± 3.4 (12) 6.9 (2.4-15) | — | — | — | — |
| Week 8 Pre-Exercise | 8.5 ± 3.9 (10) 8 (2.8-13.3) | 7.9 ± 5.4 (11) 5.9 (2.6-19) | 8.7 ± 4.2 (12) 9.5 (2.7-14.7) | — | — | — | — |
| Week 8 Post-Exercise | 7.0 ± 4.8 (10) 5.8 (1.5-15.7) | 9.6 ± 4.6 (11) 9.7 (2.4-16) | 5.1 ± 2.1 (11) 4.4 (2-8.8) | — | — | — | — |
| Change from Week 0 to Week 8 Pre-Exercise | 0.0 ± 5.5 (10) 0.7 (-10.5-7) p = 0.938* | 1.1 ± 5.7 (11) 1.5 (-13-9.6) p = 0.442* | 1.1 ± 4.7 (12) 0.4 (-8.3-8.8) p = 0.556* | 0.978* | 1.000* | 0.985* | 0.980* |
| Change from Week 0 to Week 8 Post-Exercise | -1.5 ± 3.4 (10) -0.9 (-9.5-3.1) p = 0.255* | 2.8 ± 3.3 (11) 2.3 (-2.5-7.2) p = 0.015* | -2.7 ± 3.5 (11) -2 (-8.5-2.1) p = 0.051* | 0.016* | 0.078* | 0.800* | 0.016* |
| Change from Pre-Exercise to Post-Exercise Week 8 | -1.5 ± 5.6 (10) -2.8 (-9.8-9.8) p = 0.245* | 1.7 ± 5.5 (11) 2.8 (-11.1-10.5) p = 0.237* | -3.4 ± 5.3 (11) -1.2 (-11.8-3.9) p = 0.105* | 0.067* | 0.246* | 0.776* | 0.061* |
| AUC of Total mTOR per Microgram Protein (×10$^1$) | | | | | | | |
| Week 0 Baseline Pre-Exercise | 5.6 ± 4.7 (10) 5.1 (0.2-13.5) | 6.0 ± 5.3 (11) 5.9 (0.5-17.9) | 4.3 ± 4.7 (12) 2.8 (0.7-17.7) | — | — | — | — |
| Week 8 Pre-Exercise | 5.0 ± 5.2 (10) 3.3 (0.1-15.9) | 7.5 ± 7.0 (11) 6 (0.3-18.5) | 7.8 ± 7.7 (12) 4.7 (1.4-26.1) | — | — | — | — |
| Week 8 Post-Exercise | 6.7 ± 4.4 (10) 5.7 (1.4-15.7) | 7.4 ± 6.4 (11) 5.6 (1-18.7) | 7.0 ± 5.5 (11) 4.2 (1.1-18.3) | — | — | — | — |
| Change from Week 0 to Week 8 Pre-Exercise | -0.7 ± 4.7 (10) -0.3 (-10.7-6.7) p = 0.590* | 1.5 ± 5.5 (11) 0.5 (-8.5-9.8) p = 0.795* | 3.5 ± 4.3 (12) 2.7 (-0.8-10.9) p = 0.017* | 0.122* | 0.758* | 0.112* | 0.364* |
| Change from Week 0 to Week 8 Post-Exercise | 1.0 ± 3.6 (10) 0.8 (-6.6-6.5) p = 0.121* | 1.5 ± 5.8 (11) 0.8 (-6.7-13.7) p = 0.487* | 2.4 ± 5.6 (11) 2.1 (-9-10.6) p = 0.058* | 0.858* | 0.864* | 0.994* | 0.905* |
| Change from Pre-Exercise to Post-Exercise Week 8 | 1.7 ± 4.2 (10) 1.3 (-7.5-7.1) p = 0.057* | -0.0 ± 7.0 (11) 1.1 (-16.5-10) p = 0.650* | -1.3 ± 7.5 (11) -0.3 (-17.3-8) p = 0.537* | 0.591* | 0.721* | 0.587* | 0.967* |
| AUC of Phospho-S6K per Microgram Protein (×10$^1$) | | | | | | | |
| Week 0 Baseline Pre-Exercise | 8.3 ± 4.1 (10) 8 (1.7-14.3) | 10.8 ± 3.4 (11) 9.7 (8.1-18) | 8.4 ± 4.3 (12) 8 (1.6-17.4) | — | — | — | — |
| Week 8 Pre-Exercise | 8.2 ± 4.5 (10) 8.2 (2.8-15.9) | 11.4 ± 3.6 (11) 11.7 (4.8-15.2) | 11.2 ± 8.9 (12) 8.4 (3.9-35.2) | — | — | — | — |

TABLE 9-continued

Quantity of Proteins at Week 0 and Pre and Post Exercise at Week 8 for All Participants in the PP Population (N = 33).

| | Placebo Mean ± SD (n) Median (Min-Max) Within Group P Value | Carnipure Product 1 Mean ± SD (n) Median (Min-Max) Within Group P Value | Carnipure Product 2 Mean ± SD (n) Median (Min-Max) Within Group P Value | P Value | | | |
|---|---|---|---|---|---|---|---|
| | | | | Overall[A] | Placebo vs Carnipure Product 1[δ] | Placebo vs Carnipure Product 2[δ] | Carnipure Product 1 vs Carnipure Product 2[δ] |
| Week 8 Post-Exercise | 9.4 ± 9.4 (10) 7.1 (1.1-34.3) | 6.9 ± 1.8 (11) 7.2 (4.9-10.6) | 7.3 ± 4.6 (11) 6 (2-17.8) | — | — | — | — |
| Change from Week 0 to Week 8 Pre-Exercise | −0.1 ± 4.0 (10) 1.4 (−6.2-5.3) p = 0.959* | 0.5 ± 4.5 (11) 0.2 (−9-6.5) p = 0.816* | 2.7 ± 7.5 (12) 1.8 (−5.3-24.6) p = 0.159* | 0.449* | 0.546* | 0.482* | 0.999* |
| Change from Week 0 to Week 8 Post-Exercise | 1.1 ± 11.1 (10) −0.3 (−8-30.8) p = 0.774* | −3.9 ± 4.0 (11) −2.4 (−13-0.9) p = 0.005* | −0.8 ± 3.4 (11) 0.4 (−9.4-4) p = 0.384* | 0.864* | 0.852* | 0.972* | 0.943* |
| Change from Pre-Exercise to Post-Exercise Week 8 | 1.1 ± 10.5 (10) −2.8 (−7.9-28.9) p = 0.812* | −4.4 ± 4.8 (11) −3.8 (−9.9-5.8) p = 0.019* | −4.0 ± 7.8 (11) −3.1 (−25.6-3.4) p = 0.046* | 0.870* | 0.946* | 0.858* | 0.977* |
| AUC of Total S6K per Microgram Protein (×10¹) | | | | | | | |
| Week 0 Baseline Pre-Exercise | 18.6 ± 14.0 (10) 16.1 (4.7-44) | 17.7 ± 12.5 (11) 17.3 (0.4-41.9) | 19.2 ± 9.0 (12) 18.9 (7.5-31.7) | — | — | — | — |
| Week 8 Pre-Exercise | 26.6 ± 14.7 (10) 24.1 (1.3-57.6) | 20.3 ± 12.2 (11) 23 (2-43) | 19.5 ± 7.3 (12) 20.4 (8.1-29.8) | — | — | — | — |
| Week 8 Post-Exercise | 28.3 ± 28.0 (10) 20.3 (6.4-102.4) | 35.6 ± 37.1 (11) 18.2 (6.1-122.5) | 28.3 ± 17.5 (11) 28.2 (6.8-57) | — | — | — | — |
| Change from Week 0 to Week 8 Pre-Exercise | 8.0 ± 13.8 (10) 10.8 (−17.8-26.9) p = 0.373* | 2.6 ± 13.9 (11) 1.6 (−25.4-20.5) p = 0.310* | 0.2 ± 13.0 (12) −0.1 (−23.5-20.1) p = 0.833* | 0.825* | 0.841* | 0.861* | 0.998* |
| Change from Week 0 to Week 8 Post-Exercise | 9.8 ± 29.5 (10) 1.3 (−24.1-83.4) p = 0.180* | 17.9 ± 34.5 (11) 7 (−11.3-104.8) p = 0.038* | 9.1 ± 13.3 (11) 4.3 (−11.7-31.5) p = 0.098* | 0.665* | 0.692* | 0.996* | 0.739* |
| Change from Pre-Exercise to Post-Exercise Week 8 | 2 ± 37 (10) −11 (−27-101) p = 0.965* | 15 ± 37 (11) 4 (−30-99) p = 0.162* | 10 ± 16 (11) 1 (−12-35) p = 0.218* | 0.919* | 0.920* | 0.946* | 0.997* |
| AUC of Phospho-4EBP1 per Microgram Protein (×10¹) | | | | | | | |
| Week 0 Baseline Pre-Exercise | 23.1 ± 14.6 (10) 21.8 (2-41.2) | 27.5 ± 20.6 (11) 28.4 (4.3-64) | 22.9 ± 12.6 (12) 23.3 (6.8-52.4) | — | — | — | — |
| Week 8 Pre-Exercise | 14.8 ± 11.1 (10) 12.5 (3.9-34) | 21.0 ± 21.8 (11) 12.8 (0.4-62) | 17.5 ± 14.6 (12) 13.2 (2-46) | — | — | — | — |
| Week 8 Post-Exercise | 16.2 ± 10.5 (10) 17.3 (3.4-31.1) | 12.2 ± 6.5 (11) 9.7 (4.8-22.9) | 13.9 ± 11.9 (11) 10.9 (1.8-33.9) | — | — | — | — |
| Change from Week 0 to Week 8 Pre-Exercise | −8.5 ± 15.4 (10) −1.3 (−34.8-6) p = 0.276* | −6.5 ± 12.7 (11) −2 (−29.8-14.3) p = 0.153* | −5.5 ± 16.6 (12) −4.8 (−39-21.5) p = 0.057* | 0.924* | 0.918* | 0.985* | 0.968* |
| Change from | −6.9 ± 14.2 (10) | −15.3 ± 19.8 (11) | −8.8 ± 11.1 (11) | 0.583* | 0.802* | 0.556* | 0.908* |

TABLE 9-continued

Quantity of Proteins at Week 0 and Pre and Post Exercise at Week 8 for All Participants in the PP Population (N = 33).

| | Placebo Mean ± SD (n) Median (Min-Max) Within Group P Value | Carnipure Product 1 Mean ± SD (n) Median (Min-Max) Within Group P Value | Carnipure Product 2 Mean ± SD (n) Median (Min-Max) Within Group P Value | P Value[c] Overall[A] | Placebo vs Carnipure Product 1[δ] | Placebo vs Carnipure Product 2[δ] | Carnipure Product 1 vs Carnipure Product 2[δ] |
|---|---|---|---|---|---|---|---|
| Week 0 to Week 8 Post-Exercise | −8 (−35.2-11.7) p = 0.316* | −5.5 (−56.1-4.3) p = 0.040* | −4.9 (−25-4.2) p = 0.019* | | | | |
| Change from Pre-Exercise to Post-Exercise Week 8 | 1.6 ± 15.0 (10) 2.5 (−28-24.7) p = 0.816* | −8.8 ± 23.6 (11) −0.7 (−54.1-17.9) p = 0.898* | −0.9 ± 15.9 (11) −0.1 (−26.2-25.2) p = 0.865* | 0.765* | 0.915* | 0.745* | 0.938* |
| AUC of Total 4EBP1 per Microgram Protein (×10$^1$) | | | | | | | |
| Week 0 Baseline Pre-Exercise | 10.1 ± 5.2 (10) 8.3 (4.8-19.9) | 20.0 ± 10.6 (11) 18.2 (3.5-38.8) | 20.8 ± 11.4 (12) 18.7 (3.9-47.1) | — | — | — | — |
| Week 8 Pre-Exercise | 21.1 ± 32.3 (10) 10.3 (1.8-110.6) | 16.4 ± 13.5 (11) 12.4 (5.7-42.9) | 13.8 ± 7.0 (12) 14.7 (0.8-28.2) | — | — | — | — |
| Week 8 Post-Exercise | 14.6 ± 11.0 (10) 11.7 (1.1-34.3) | 17.8 ± 7.3 (11) 17.9 (3.8-27.9) | 16.1 ± 13.6 (11) 12.8 (3.3-51.4) | — | — | — | — |
| Change from Week 0 to Week 8 Pre-Exercise | 11.0 ± 33.1 (10) 1.9 (−4.8-104.7) p = 0.619* | −3.6 ± 10.9 (11) −4.3 (−19.7-17.6) p = 0.170* | −7.0 ± 14.3 (12) −2.6 (−38.8-10.2) p = 0.151* | 0.827* | 0.967* | 0.821* | 0.916* |
| Change from Week 0 to Week 8 Post-Exercise | 4.5 ± 8.9 (10) 2.6 (−7.4-21.3) p = 0.819* | −2.2 ± 12.6 (11) −3 (−23.6-17.3) p = 0 817* | −5.0 ± 11.4 (11) −3.2 (−27.1-15.7) p = 0.114* | 0.713* | 0.873* | 0.972* | 0.698* |
| Change from Pre-Exercise to Post-Exercise Week 8 | −6.5 ± 31.4 (10) 3.6 (−92.7-19.6) p = 0.725* | 1.4 ± 16.5 (11) 5 (−30-20.5) p = 0.497* | 3.6 ± 15.5 (11) 0.5 (−10.9-43.1) p = 0.607* | 0.461* | 0.428* | 0.773* | 0.828* |
| AUC of Phospho-p65 per Microgram Protein (×10$^1$) | | | | | | | |
| Week 0 Baseline Pre-Exercise | 9.0 ± 10.1 (10) 5.4 (2.1-30.9) | 9.4 ± 15.2 (11) 16.1 (4.3-54.4) | 10.9 ± 10.2 (12) 10.3 (2-40.3) | — | — | — | — |
| Week 8 Pre-Exercise | 10.0 ± 8.9 (10) 5.3 (1-23.8) | 12.1 ± 8.2 (11) 9.3 (4.6-26.5) | 11.1 ± 10.2 (12) 7.9 (1.6-32.2) | — | — | — | — |
| Week 8 Post-Exercise | 7.4 ± 7.0 (10) 8.1 (0.4-20.6) | 8.6 ± 4.3 (11) 9.5 (1.2-18.6) | 7.4 ± 4.1 (11) 6.6 (1.2-15.4) | — | — | — | — |
| Change from Week 0 to Week 8 Pre-Exercise | 1.0 ± 6.8 (10) −0.5 (−10.6-15) p = 0.837* | −7.4 ± 12.0 (11) −4 (−37-9.8) p = 0.021* | 0.2 ± 6.6 (12) −0.6 (−8.1-16.8) p = 0.705* | 0.488* | 0.508* | 0.973* | 0.574* |
| Change from Week 0 to Week 8 Post-Exercise | −1.7 ± 10.5 (10) −1.6 (−22.8-18.5) p = 0.272* | −10.8 ± 15.2 (11) −6.6 (−48.9-5.3) p = 0.017* | −3.3 ± 10.9 (11) 0.5 (−33.7-6.2) p = 0.444* | 0.522* | 0.737* | 0.497* | 0.946* |
| Change from | −2.6 ± 9.5 (10) | −3.5 ± 9.0 (11) 1.5 (−19.8-5.4) | −3.2 ± 11.3 (11) | 0.302* | 0.330* | 0.407* | 0.982* |

TABLE 9-continued

Quantity of Proteins at Week 0 and Pre and Post Exercise at Week 8 for All Participants in the PP Population (N = 33).

| | Placebo<br>Mean ± SD<br>(n)<br>Median (Min-Max)<br>Within<br>Group P<br>Value | Carnipure<br>Product 1<br>Mean ± SD (n)<br>Median (Min-Max)<br>Within Group<br>P Value | Carnipure<br>Product 2<br>Mean ± SD (n)<br>Median (Min-Max)<br>Within Group<br>P Value | P Value | | | |
|---|---|---|---|---|---|---|---|
| | | | | Overall[Δ] | Placebo<br>vs Carnipure<br>Product 1[δ] | Placebo<br>vs Carnipure<br>Product 2[δ] | Carnipure<br>Product 1<br>vs Carnipure<br>Product 2[δ] |
| Pre-Exercise to Post-Exercise Week 8 | −4.8 (−12.3-19.3)<br>p = 0.303* | p = 0.275* | −0.1 (−25.6-8.1)<br>p = 0.701* | | | | |
| *AUC of Total p65 per Microgram Protein (×10¹)* | | | | | | | |
| Week 0 Baseline Pre-Exercise | 13.8 ± 11.8 (10)<br>9.2 (1.7-31) | 6.8 ± 5.6 (11)<br>3.5 (1.4-18.2) | 11.4 ± 8.2 (12)<br>10.3 (1-26.1) | — | — | — | — |
| Week 8 Pre-Exercise | 14.2 ± 9.2 (10)<br>13.2 (2.6-26.5) | 6.0 ± 4.6 (11)<br>5 (1.51-6.7) | 9.0 ± 5.4 (12)<br>7.7 (1.5-21.1) | — | — | — | — |
| Week 8 Post-Exercise | 11.1 ± 8.1 (10)<br>8.3 (3.1-27.5) | 8.6 ± 7.1 (11)<br>6 (1.3-21.1) | 8.8 ± 6.8 (11)<br>5.8 (2.9-26.6) | — | — | — | — |
| Change from Week 0 to Week 8 Pre-Exercise | 0.4 ± 9.1 (10)<br>1.5 (−14.7-17.6)<br>p = 0.245* | −0.8 ± 5.9 (11)<br>0.1 (−11.4-9.1)<br>p = 0.775* | −2.4 ± 8.4 (12)<br>−0.5 (−19.7-6)<br>p = 0.787* | 0.103* | 0.087* | 0.372* | 0.617* |
| Change from Week 0 to Week 8 Post-Exercise | −2.7 ± 13.5 (10)<br>−1.9 (−25.2-19.3)<br>p = 0.952* | 1.8 ± 7.1 (11)<br>2.7 (−6-19.7)<br>p = 0.565* | −3.5 ± 9.1 (11)<br>−2.2 (−20.9-10.4)<br>p = 0.367* | 0.671* | 0.667* | 0.796* | 0.969* |
| Change from Pre-Exercise to Post-Exercise Week 8 | −3.1 ± 9.4 (10)<br>−3.3 (−18.7-9.5)<br>p = 0.323 | 2.6 ± 9.4 (11)<br>1 (−9.6-19.6)<br>p = 0.379 | −0.9 ± 10.5 (11)<br>−2.6 (−15.3-23.3)<br>p = 0.787 | 0.509* | 0.478* | 0.773* | 0.821* |
| *AUC of Total p50 per Microgram Protein (×10¹)* | | | | | | | |
| Week 0 Baseline Pre-Exertise | 15.7 ± 6.0 (10)<br>16.8 (7.7-21.9) | 13.9 ± 9.2 (11)<br>9.5 (5.7-33.6) | 11.6 ± 6.3 (12)<br>8.5 (3.3-21.6) | — | — | — | — |
| Week 8 Pre-Exercise | 18.2 ± 6.5 (10)<br>19.1 (7.8-27.7) | 13.8-8.0 (11)<br>14.3 (6-34.7) | 12.8 ± 5.3 (12)<br>11.7 (4.4-21.6) | — | — | — | — |
| Week 8 Post-Exercise | 21.6 ± 14.1 (10)<br>21.6 (3.2-48.4) | 10.6 ± 6.7 (11)<br>9.1 (3.2-21.6) | 17.4 ± 12.6 (11)<br>15.5 (4.5-41.1) | — | — | — | — |
| Change from Week 0 to Week 8 Pre-Exercise | 2.5 ± 6.0 (10)<br>1.8 (−9-12)<br>p = 0.237* | −0.0 ± 4.4 (11)<br>0.5 (7.1-9.6)<br>p = 0.599* | 1.2 ± 5.1 (12)<br>0.4 (−7.6-9.6)<br>p = 0.352* | 0.380* | 0.397* | 0.487* | 0.986* |
| Change from Week 0 to Week 8 Post-Exercise | 5.8 ± 15.2 (10)<br>1.7 (−12.9-37.7)<br>p = 0.683* | −3.2 ± 10.3 (11)<br>−0.3 (−27.7-6.7)<br>p = 0.294* | 5.4 ± 11.7 (11)<br>1.2 (−10-33)<br>p = 0.248* | 0.209* | 0.243* | 0.967* | 0.331* |

TABLE 9-continued

Quantity of Proteins at Week 0 and Pre and Post Exercise at Week 8 for All Participants in the PP Population (N = 33).

| | Placebo Mean ± SD (n) Median (Min-Max) Within Group P Value | Carnipure Product 1 Mean ± SD (n) Median (Min-Max) Within Group P Value | Carnipure Product 2 Mean ± SD (n) Median (Min-Max) Within Group P Value | P Value[◇] | | | |
|---|---|---|---|---|---|---|---|
| | | | | Overall[Δ] | Placebo vs Carnipure Product 1[δ] | Placebo vs Carnipure Product 2[δ] | Carnipure Product 1 vs Carnipure Product 2[δ] |
| Change from Exercise to Post-Exercise Week 8 | 3.3 ± 15.6 (10) 2.1 (−14.5-37) p = 0.912* | −3.2 ± 11.2 (11) 0.9 (−28.8-7.1) p = 0.240* | 4.2 ± 13.4 (11) 4.6 (−11.5-33.3) p = 0.727* | 0.174* | 0.165* | 0.778* | 0.419* |

N, number;
SD, standard deviation;
Min, minimum;
Max, maximum;
AUC, area under the curve
[Δ]Between-group comparisons were made using ANCOVA.
[δ]Pairwise between-group comparisons were made using the Tukey procedure.
Within-group comparisons were made using the paired Student t-test.
*Logarithmic transformation required to achieve normality.
Probability values P ≤ 0.05 are statistically significant.

Anthropometrics and vital signs were taken for each participant prior to Day 0 and on Day 57±3, As seen in Table 10, there were no significant between-group differences for both systolic and diastolic blood pressure as well as heart rate, weight, and BMI for all post randomization time points.

Within groups, there was a significant change in diastolic blood pressure for the Sample 1 group, as well as mean heart rate in the Sample 2 group relative to baseline. All blood pressure and heart rate values were within acceptable clinical range.

TABLE 10

Vital Signs for All Participants Enrolled in the Study at Baseline and Week 8 (N = 42).

| | Placebo Mean ± SD (n) Median (Min-Max) Within Group P Value | Sample 1 Mean ± SD (n) Median (Min-Max) Within Group P Value | Sample 2 Mean ± SD (n) Median (Min-Max) Within Group P Value | P Value[Δ] |
|---|---|---|---|---|
| Mean Systolic Blood Pressure (mmHg) | | | | |
| Baseline (Week 0) | 112.2 ± 9.5 (14) 112.7 (97.3-131.3) | 119.1 ± 10.3 (14) 117.5 (104.7-141.7) | 115.7 ± 12.9 (14) 115.7 (96-138.3) | — |
| Visit 3 (Week 8) | 112.0 ± 11.1 (13) 112.7 (94-134.3) | 121.2 ± 11.1 (14) 121.3 (101.3-140) | 118.3 ± 12.9 (14) 118.7 (94-142) | — |
| Change from Baseline to Week 8 | 0.4 ± 11.0 (13) 0.3 (−18.7-20) p = 0.902 | 2.1 ± 8.5 (14) 2.7 (−14-21) p = 0.373 | 2.6 ± 12.3 (14) 1.7 (−18-20) p = 0.435 | 0.447 |
| Mean Diastolic Blood Pressure (mmHg) | | | | |
| Baseline (Week 0) | 69.2 ± 6.9 (14) 70.2 (54.7-78.7) | 70.0 ± 7.0 (14) 70.8 (60.7-84.7) | 71.9 ± 9.1 (14) 73.3 (52.3-85.7) | — |
| Visit 3 (Week 8) | 69.3 ± 6.1 (13) 69.3 (60-80) | 74.1 ± 6.3 (14) 73.5 (62.7-88) | 74.9 ± 11.9 (14) 75.5 (55.3-96.7) | — |
| Change from Baseline to Week 8 | 0.1 ± 7.4 (13) −0.3 (−10.7-19.3) p = 0.952 | 4.1 ± 6.0 (14) 5.8 (−11.3-11.3) p = 0.024 | 3.0 ± 7.6 (14) 3.5 (9.7-16.7) p = 0.162 | 0.223 |
| Mean Heart Rate (BPM) | | | | |
| Baseline (Week 0) | 73.6 ± 12.6 (14) 69.8 (52-103.3) | 71.6 ± 7.3 (14) 72 (56.3-83.3) | 71.7 ± 6.9 (14) 72.5 (54.7-81.3) | — |
| Visit 3 (Week 8) | 68.1 ± 7.2 (13) 69.3 (53.3-81.3) | 69.9 ± 7.1 (14) 69.2 (56-85) | 66.6 ± 5.2 (14) 66.7 (54.7-74.7) | — |
| Change from Baseline to Week 8 | −3.2 ± 10.6 (13) −3.3 (−20.7-13.3) p = 0.297 | −1.7 ± 8.4 (14) −1.3 (−16-13.3) p = 0.464 | −5.1 ± 7.6 (14) −4.7 (−22.7-8) p = 0.024 | 0.391 |
| Weight (kg) | | | | |
| Baseline (Week 0) | 72.1 ± 8.3 (14) 71.2 (60.5-86.2) | 74.8 ± 13.4 (14) 75.3 (55.8-98.2) | 76.5 ± 14.2 (14) 72.8 (56-102) | — |
| Visit 3 (Week 8) | 73.1 ± 8.0 (13) 73 (61.5-88) | 75.3 ± 13.4 (14) 75 (57-97.9) | 77.0 ± 14.1 (14) 74.5 (56.5-102.3) | — |

TABLE 10-continued

Vital Signs for All Participants Enrolled in the Study at Baseline and Week 8 (N = 42).

| | Placebo<br>Mean ± SD (n)<br>Median (Min-Max)<br>Within Group P Value | Sample 1<br>Mean ± SD (n)<br>Median (Min-Max)<br>Within Group P Value | Sample 2<br>Mean ± SD (n)<br>Median (Min-Max)<br>Within Group P Value | P Value[Δ] |
|---|---|---|---|---|
| Change from<br>Baseline to<br>Week 8 | 0.23 ± 0.82 (13)<br>0.2 (−1.5-1.8)<br>p = 0.294[‡] | 0.46 ± 1.89 (14)<br>0.65 (−3.2-4.6)<br>p = 0.330[‡] | 0.48 ± 1.23 (14)<br>0.5 (−2.2-3)<br>p = 0.116[‡] | 0.678[□] |
| | | BMI (kg/m$^2$) | | |
| Baseline<br>(Week 0) | 26.00 ± 1.83 (14)<br>25.16 (23.49-30.18) | 26.54 ± 3.03 (14)<br>26.78 (21.8-31.56) | 27.60 ± 3.05 (14)<br>27.31 (22.58-32.48) | — |
| Visit 3<br>(Week 8) | 26.22 ± 2.00 (13)<br>25.6 (23.67-30.81) | 26.70 ± 2.96 (14)<br>26.89 (22.27-31.46) | 27.77 ± 2.89 (14)<br>27.69 (22.66-32.58) | — |
| Change from<br>Baseline to<br>Week 8 | 0.10 ± 0.28 (13)<br>0.07 (−0.45-0.63)<br>p = 0.239 | 0.16 ± 0.66 (14)<br>0.24 (−1.17-1.51)<br>p = 0.372 | 0.17 ± 0.47 (14)<br>0.18 (−0.88-1.13)<br>p = 0.195 | 0.820 |

N, number;
SD, standard deviation;
Min, minimum;
Max, maximum;
mmHg, millimeters of mercury;
BPM, beats per minute.
[Δ]Between-group comparisons were made using ANCOVA.
[□]Between group were made using the Kruskal Wallis test. Within-group comparisons were made using the paired Student t-test.
[‡]Within group were made using the Sign Rank test. Probability values P ≤ 0.05 are statistically significant.

Blood samples were taken for each participant taken prior to Day 0 and on Day 57±3 to measure hematology and clinical chemistry parameters. Table 11 demonstrates that there were no significant between group changes in hematology and clinical chemistry parameters for participants, with the exception of creatinine (P=0.027), estimated globular filtration rate (P=0.029), and aspartate transaminase (P=0.034) concentrations. However, these markers remained within their established clinical reference ranges.

There were five safety parameters that showed significant within group change from screening to the end of study (week 8). White blood cell count (P=0.021), lymphocyte count (P=0.022), and aspartate transaminase levels (P=0.033) increased for subjects on Sample 1, while chloride levels decreased significantly (P=0.013) for this group. The creatinine concentration (P=0.05) was significantly increased for the Sample 2 group. Estimated globular filtration rate (P=0.069) was not significantly changed for subjects within the Sample 2 group. Overall, all hematological and clinical parameters were within acceptable clinical range for this population.

TABLE 11

Haematology and Clinical Chemistry Parameters for All Enrolled Participants at Screening and Week 8 (N = 42).

| | | Placebo<br>Mean ± SD (n)<br>Median (Min-Max)<br>Within Group P Value | Sample 1<br>Mean ± SD (n)<br>Median (Min-Max)<br>Within Group P Value | Sample 2<br>Mean ± SD (n)<br>Median (Min-Max)<br>Within Group P Value | P Value[Δ] |
|---|---|---|---|---|---|
| | | Hemoglobin Concentration (g/L) | | | |
| | Screening | 138.4 ± 7.9 (14)<br>137.5 (128-156) | 144.0 ± 10.0 (14)<br>143.5 (131-159) | 140.3 ± 12.6 (14)<br>136 (124-167) | — |
| | Visit 3<br>(Week 8) | 138.6 ± 6.5 (14)<br>138 (128-151) | 141.6 ± 9.3 (13)<br>140 (124-154) | 137.9 ± 12.2 (14)<br>138 (116-159) | — |
| | Change from<br>Screening to<br>Week 8 | 0.3 ± 7.6 (14)<br>1.5 (−15-11)<br>p = 0.834[‡] | −1.2 ± 6.5 (13)<br>1 (−14-12)<br>p = 0.505[‡] | −2.4 ± 7.1 (14)<br>0 (−18-7)<br>p = 0.307[‡] | 0.559[□] |
| | | Hematocrit (L/L) | | | |
| | Screening | 0.4021 ± 0.0236 (14)<br>0.4 (0.37-0.45) | 0.4229 ± 0.0246 (14)<br>0.43 (0.39-0.46) | 0.4093 ± 0.0300 (14)<br>0.4 (0.37-0.47) | — |
| | Visit 3<br>(Week 8) | 0.4064 ± 0.0178 (14)<br>0.41 (0.38-0.44) | 0.4162 ± 0.0260 (13)<br>0.41 (0.37-0.46) | 0.4036 ± 0.0310 (14)<br>0.405 (0.34-0.45) | — |
| | Change from<br>Screening to<br>Week 8 | 0.0043 ± 0.0217 (14)<br>0.005 (−0.04-0.04)<br>p = 0.420[‡] | −0.0046 ± 0.0176 (13)<br>−0.01 (−0.04-0.03)<br>p = 0.337[‡] | −0.0057 ± 0.0187 (14)<br>0 (−0.05-0.02)<br>p = 0.262[‡] | 0.374[□] |
| | | White Blood Cell Count (×E9/L) | | | |
| | Screening | 5.91 ± 1.16 (14)<br>5.65 (4.6-7.9) | 5.88 ± 1.88 (14)<br>5.3 (3.8-9.3) | 6.25 ± 1.86 (14)<br>6 (3.8-10.8) | — |
| | Visit 3<br>(Week 8) | 5.64 ± 1.32 (14)<br>5.6 (3.7-8.7) | 6.59 ± 1.75 (13)<br>6.4 (4.3-10.5) | 6.17 ± 1.91 (14)<br>6.15 (3.9-11) | — |

TABLE 11-continued

Haematology and Clinical Chemistry Parameters for All Enrolled Participants at Screening and Week 8 (N = 42).

| | Placebo<br>Mean ± SD (n)<br>Median (Min-Max)<br>Within Group P Value | Sample 1<br>Mean ± SD (n)<br>Median (Min-Max)<br>Within Group P Value | Sample 2<br>Mean ± SD (n)<br>Median (Min-Max)<br>Within Group P Value | P Value$^\Delta$ |
|---|---|---|---|---|
| Change from Screening to Week 8 | −0.28 ± 1.10 (14)<br>−0.3 (−2.2-1.3)<br>p = 0.441‡ | 0.68 ± 0.83 (13)<br>0.5 (−0.4-2.3)<br>p = 0.021‡ | −0.08 ± 0.87 (14)<br>0 (−1.4-1.2)<br>p = 0.753‡ | 0.054$^\square$ |
| Red Blood Cell Count (×E12/L) | | | | |
| Screening | 4.48 ± 0.26 (14)<br>4.47 (3.94-5.04) | 4.72 ± 0.40 (14)<br>4.7 (4.01-5.34) | 4.55 ± 0.35 (14)<br>4.49 (4.08-5.12) | — |
| Visit 3 (Week 8) | 4.58 ± 0.22 (14)<br>4.56 (4.23-4.95) | 4.66 ± 0.44 (13)<br>4.61 (3.96-5.4) | 4.44 ± 0.34 (14)<br>4.42 (3.87-5.01) | — |
| Change from Screening to Week 8 | 0.09 ± 0.35 (14)<br>0.03 (−0.41-0.93)<br>p = 0.329* | −0.07 ± 0.21 (13)<br>−0.05 (−0.48-0.31)<br>p = 0.244* | −0.11 ± 0.30 (14)<br>−0.07 (−0.97-0.21)<br>p = 0.212* | 0.222* |
| Mean Corpuscular Volume (fL) | | | | |
| Screening | 89.9 ± 3.0 (14)<br>89 (85.1-96.3) | 89.7 ± 4.6 (14)<br>88.2 (83.3-100.2) | 89.9 ± 3.5 (14)<br>90.8 (81.2-93.6) | — |
| Visit 3 (Week 8) | 88.6 ± 3.7 (14)<br>89 (80.5-96.3) | 89.2 ± 3.0 (13)<br>89 (84.6-93.8) | 90.8 ± 3.0 (14)<br>91.2 (84.4-95.3) | — |
| Change from Screening to Week 8 | −1.28 ± 3.55 (14)<br>−0.15 (−12.6-1.4)<br>p = 0.221‡ | 0.40 ± 1.16 (13)<br>0.8 (−3-1.5)<br>p = 0.077‡ | 0.86 ± 2.21 (14)<br>0.4 (−1.9-7.2)<br>p = 0.116‡ | 0.091$^\square$ |
| Mean Corpuscular Hemoglobin (pg) | | | | |
| Screening | 30.89 ± 1.08 (14)<br>30.9 (28.9-33) | 30.61 ± 1.75 (14)<br>30.15 (28.3-35.2) | 30.86 ± 1.40 (14)<br>31.15 (27.7-33.3) | — |
| Visit 3 (Week 8) | 30.32 ± 1.40 (14)<br>30.35 (27.3-33.2) | 30.45 ± 1.10 (13)<br>30.4 (28.5-32.1) | 31.04 ± 1.25 (14)<br>31.35 (28.7-33.6) | — |
| Change from Screening to Week 8 | −0.56 ± 1.42 (14)<br>−0.15 (−5.2-0.4)<br>p = 0.162* | 0.19 ± 0.36 (13)<br>0.2 (−0.6-0.8)<br>p = 0.070* | 0.19 ± 0.74 (14)<br>0.1 (−0.5-2.3)<br>p = 0.371* | 0.093* |
| Mean Corpuscular Hemoglobin Concentration (g/L) | | | | |
| Screening | 343.6 ± 5.6 (14)<br>342.5 (336-356) | 341.1 ± 5.6 (14)<br>340 (331-351) | 342.9 ± 6.7 (14)<br>342.5 (333-356) | — |
| Visit 3 (Week 8) | 342.2 ± 5.5 (14)<br>341 (333-353) | 341.2 ± 5.4 (13)<br>341 (331-349) | 342.1 ± 6.0 (14)<br>340 (335-353) | — |
| Change from Screening to Week 8 | −1.4 ± 6.2 (14)<br>−3 (−11-11)<br>p = 0.362‡ | 0.9 ± 3.9 (13)<br>1 (−7-9)<br>p = 0.331‡ | −0.9 ± 5.1 (14)<br>−1.5 (−9-6)<br>p = 0.599‡ | 0.449$^\square$ |
| Red Cell Distribution Width (%) | | | | |
| Screening | 13.61 ± 0.40 (14)<br>13.45 (13.1-14.4) | 13.91 ± 0.47 (14)<br>13.9 (12.8-14.5) | 13.58 ± 0.51 (14)<br>13.55 (12.8-14.4) | — |
| Visit 3 (Week 8) | 13.56 ± 0.34 (14)<br>13.6 (13-14.3) | 13.83 ± 0.48 (13)<br>13.7 (13.1-14.7) | 13.61 ± 0.56 (14)<br>1.75 (12.3-14.4) | — |
| Change from Screening to Week 8 | −0.06 ± 0.30 (14)<br>−0.05 (−0.9-0.4)<br>p = 0.778* | −0.10 ± 0.43 (13)<br>0 (−1.2-0.6)<br>p = 0.123* | 0.03 ± 0.41 (14)<br>0.15 (−0.9-0.6)<br>p = 0.685* | 0.838 |
| Platelet Count (×E9/L) | | | | |
| Screening | 239 ± 34 (14)<br>246 (186-305) | 265 ± 63 (14)<br>254 (190-424) | 271 ± 65 (14)<br>268 (145-371) | — |
| Visit 3 (Week 8) | 235 ± 29 (14)<br>238 (190-273) | 275 ± 68 (13)<br>266 (171-430) | 258 ± 63 (14)<br>262 (140-362) | — |
| Change from Screening to Week 8 | −4.6 ± 20.9 (14)<br>3 (−36-42)<br>p = 0.615‡ | 5.4 ± 15.4 (13)<br>5 (−19-33)<br>p = 0.289‡ | −13.0 ± 28.3 (14)<br>−5 (−67-41)<br>p = 0.090‡ | 0.118$^\square$ |
| Neutrophil Count (×E9/L) | | | | |
| Screening | 3.41 ± 0.64 (14)<br>3.3 (2.4-4.5) | 3.17 ± 1.36 (14)<br>2.95 (1.6-6.4) | 3.59 ± 1.21 (14)<br>3.25 (2-6.4) | — |
| Visit 3 (Week 8) | 3.15 ± 0.77 (14)<br>3.15 (1.6-4.8) | 3.63 ± 1.32 (13)<br>3.7 (1.5-6) | 3.34 ± 1.35 (14)<br>3.15 (1.6-6.8) | — |
| Change from Screening to Week 8 | −0.26 ± 0.72 (14)<br>−0.55 (−1.1-1.1)<br>p = 0.184‡ | 0.44 ± 0.89 (13)<br>0.2 (−0.8-1.9)<br>p = 0.146‡ | −0.25 ± 0.89 (14)<br>−0.2 (−2.4-1)<br>p = 0.421‡ | 0.104$^\square$ |
| Lymphocyte Count (×E9/L) | | | | |
| Screening | 1.84 ± 0.58 (14)<br>1.95 (0.8-2.9) | 1.91 ± 0.59 (14)<br>1.7 (1.3-3) | 1.96 ± 0.76 (14)<br>2 (0.6-3.5) | — |
| Visit 3 (Week 8) | 1.94 ± 0.56 (14)<br>1.75 (0.9-3) | 2.13 ± 0.65 (13)<br>2 (1.2-3.3) | 2.03 ± 0.97 (14)<br>1.8 (0.6-4.1) | — |

TABLE 11-continued

Haematology and Clinical Chemistry Parameters for All Enrolled
Participants at Screening and Week 8 (N = 42).

| | Placebo<br>Mean ± SD (n)<br>Median (Min-Max)<br>Within Group P Value | Sample 1<br>Mean ± SD (n)<br>Median (Min-Max)<br>Within Group P Value | Sample 2<br>Mean ± SD (n)<br>Median (Min-Max)<br>Within Group P Value | P Value$^\Delta$ |
|---|---|---|---|---|
| Change from<br>Screening to<br>Week 8 | 0.00 ± 0.53 (14)<br>0.05 (−1.1-0.9)<br>p = 0.944$^\ddagger$ | 0.18 ± 0.23 (13)<br>0.2 (−0.3-0.5)<br>p = 0.022$^\ddagger$ | 0.07 ± 0.95 (14)<br>−0.05 (−0.8-3.1)<br>p = 0.555$^\ddagger$ | 0.208$^a$ |
| | | Monocyte Count (×E9/L) | | |
| Screening | 0.457 ± 0.165 (14)<br>0.4 (0.3-0.9) | 0.564 ± 0.165 (14)<br>0.55 (0.3-0.9) | 0.514 ± 0.141 (14)<br>0.5 (0.3-0.7) | — |
| Visit 3<br>(Week 8) | 0.450 ± 0.170 (14)<br>0.4 (0.3-0.8) | 0.600 ± 0.153 (13)<br>0.6 (0.4-1) | 0.564 ± 0.128 (14)<br>0.55 (0.3-0.7) | — |
| Change from<br>Screening to<br>Week 8 | −0.007 ± 0.138 (14)<br>0 (−0.3-0.2)<br>p = 0.928$^\ddagger$ | 0.031 ± 0.111 (13)<br>0 (−0.1-0.3)<br>p = 0.518$^\ddagger$ | 0.050 ± 0.151 (14)<br>0 (−0.2-0.4)<br>p = 0.276$^\ddagger$ | 0.732$^a$ |
| | | Eosinophil Count (×E9/L) | | |
| Screening | 0.164 ± 0.101 (14)<br>0.15 (0-0.4) | 0.186 ± 0.196 (14)<br>0.1 (0.1-0.8) | 0.171 ± 0.114 (14)<br>0.1 (0.1-0.5) | — |
| Visit 3<br>(Week 8) | 0.164 ± 0.108 (14)<br>0.1 (0-0.4) | 0.169 ± 0.063 (13)<br>0.2 (0.1-0.3) | 0.186 ± 0.146 (14)<br>0.15 (0-0.6) | — |
| Change from<br>Screening to<br>Week 8 | −0.000 ± 0.068 (14)<br>0 (−0.1-0.1)<br>p = 0.824$^\ddagger$ | −0.000 ± 0.191 (13)<br>0 (−0.6-0.2)<br>p = 0.388$^\ddagger$ | 0.014 ± 0.077 (14)<br>0 (−0.1-0.1)<br>p = 0.774$^\ddagger$ | 0.405$^a$ |
| | | Basophil Count (×E9/L) | | |
| Screening | 0.007 ± 0.027 (14)<br>0 (0-0.1) | 0.036 ± 0.050 (14)<br>0 (0-0.1) | 0.036 ± 0.050 (14)<br>0 (0-0.1) | — |
| Visit 3<br>(Week 8) | 0.007 ± 0.027 (14)<br>0 (0-0.1) | 0.038 ± 0.051 (13)<br>0 (0-0.1) | 0.036 ± 0.063 (14)<br>0 (0-0.2) | — |
| Change from<br>Screening to<br>Week 8 | 0.000 ± 0.000 (14)<br>0 (0-0)<br>p = 1.000$^\ddagger$ | 0.008 ± 0.028 (13)<br>0 (0-0.1)<br>p = 1.000$^\ddagger$ | 0.000 ± 0.078 (14)<br>0 (−0.1-0.2)<br>p = 1.000$^\ddagger$ | 0.626$^a$ |
| | | Fasting Glucose Concentration (mmol/L) | | |
| Screening | 5.50 ± 0.33 (14)<br>5.45 (5-6.1) | 5.20 ± 0.44 (14)<br>5.15 (4.6-6) | 5.33 ± 0.53 (14)<br>5.2 (4.6-6.2) | — |
| Visit 3<br>(Week 8) | 5.37 ± 0.56 (14)<br>5.3 (4.6-6.9) | 5.28 ± 0.70 (14)<br>5.1 (4.3-7.1) | 5.06 ± 0.76 (14)<br>5.05 (2.7-5.8) | — |
| Change from<br>Screening to<br>Week 8 | −0.13 ± 0.47 (14)<br>−0.1 (−1.2-0.8)<br>p = 0.344$^\ddagger$ | 0.08 ± 0.68 (14)<br>0 (−0.8-1.9)<br>p = 0.969$^\ddagger$ | 0.27 ± 0.79 (14)<br>0.15 (−2.5-0.6)<br>p = 0.209$^\ddagger$ | 0.762$^a$ |
| | | Creatinine Concentration (μmol/L) | | |
| Screening | 71.7 ± 13.8 (14)<br>74 (49-90) | 72.3 ± 11.1 (14)<br>73 (53-88) | 63.8 ± 7.8 (14)<br>64.5 (49-77) | — |
| Visit 3<br>(Week 8) | 73.1 ± 13.1 (14)<br>72.5 (53-92) | 71.6 ± 11.4 (14)<br>69 (53-95) | 70.7 ± 17.8 (14)<br>70.5 (33-105) | — |
| Change from<br>Screening to<br>Week 8 | 1.4 ± 7.7 (14)$^{a,b}$<br>1.5 (21-12)<br>p = 0.161$^\ddagger$ | −0.7 ± 7.4 (14)$^a$<br>−0.5 (−17-15)<br>p = 0.623$^\ddagger$ | 6.9 ± 15.5 (14)$^b$<br>5 (−34-34)<br>p = 0.050$^\ddagger$ | 0.027$^a$ |
| | | Estimated Globular Filtration Rate (mL/min/1.73 m$^2$) | | |
| Screening | 84.1 ± 17.9 (14)<br>81 (59-113) | 81.0 ± 10.4 (14)<br>80.5 (64-103) | 91.5 ± 15.8 (14)<br>87.5 (69-119) | — |
| Visit 3<br>(Week 8) | 81.4 ± 15.4 (14)<br>84.5 (54-102) | 83.6 ± 11.1 (14)<br>78.5 (67-105) | 83.8 ± 15.7 (14)<br>81 (62-121) | — |
| Change from<br>Screening to<br>Week 8 | 2.8 ± 15.0 (14)$^{a,b}$<br>3 (−30-34)<br>p = 0.345$^\ddagger$ | 2.6 ± 11.0 (14)$^b$<br>4 (−26-24)<br>p = 0.147$^\ddagger$ | 7.7 ± 18.9 (14)$^a$<br>9.5 (−38-43)<br>p = 0.069$^\ddagger$ | 0.029$^a$ |
| | | Sodium Concentration (mmol/L) | | |
| Screening | 144.36 ± 2.37 (14)<br>144 (141-148) | 144.57 ± 2.50 (14)<br>145 (141-150) | 142.79 ± 2.49 (14)<br>143.5 (138-146) | — |
| Visit 3<br>(Week 8) | 145.36 ± 2.17 (14)<br>145 (142-150) | 144.64 ± 3.18 (14)<br>145 (140-152) | 142.86 ± 2.28 (14)<br>143 (140-148) | — |
| Change from<br>Screening to<br>Week 8 | 1.00 ± 2.60 (14)<br>1.5 (−2-5)<br>p = 0.163$^\ddagger$ | 0.07 ± 3.00 (14)<br>−1 (−3-7)<br>p = 0.944$^\ddagger$ | 0.07 ± 3.38 (14)<br>0 (−5-9)<br>p = 0.918$^\ddagger$ | 0.549$^a$ |
| | | Potassium Concentration (mmol/L) | | |
| Screening | 5.10 ± 0.47 (14)<br>5.15 (4-5.7) | 5.11 ± 0.29 (14)<br>5.1 (4.8-5.6) | 4.85 ± 0.46 (14)<br>4.9 (3.8-5.7) | — |
| Visit 3<br>(Week 8) | 5.04 ± 0.59 (14)<br>5 (4-6.4) | 5.04 ± 0.38 (14)<br>5 (4.5-5.6) | 4.75 ± 0.57 (13)<br>4.8 (3.6-5.9) | — |

TABLE 11-continued

Haematology and Clinical Chemistry Parameters for All Enrolled Participants at Screening and Week 8 (N = 42).

| | Placebo<br>Mean ± SD (n)<br>Median (Min-Max)<br>Within Group P Value | Sample 1<br>Mean ± SD (n)<br>Median (Min-Max)<br>Within Group P Value | Sample 2<br>Mean ± SD (n)<br>Median (Min-Max)<br>Within Group P Value | P Value$^\Delta$ |
|---|---|---|---|---|
| Change from Screening to Week 8 | −0.06 ± 0.67 (14)<br>−0.05 (−1.3-1)<br>p = 0.861‡ | −0.08 ± 0.46 (14)<br>−0.1 (−1-0.6)<br>p = 0.637‡ | −0.08 ± 0.49 (13)<br>−0.1 (−1.1-0.6)<br>p = 0.806‡ | 0.599 |
| | | Chloride Concentration (mmol/L) | | |
| Screening | 107.64 ± 1.86 (14)<br>107 (105-112) | 108.29 ± 1.77 (14)<br>109 (105-111) | 105.50 ± 1.91 (14)<br>105.5 (103-108) | — |
| Visit 3 (Week 8) | 106.86 ± 2.35 (14)<br>106 (103-110) | 106.50 ± 2.59 (14)<br>106 (101-110) | 105.00 ± 2.04 (14)<br>106 (1.2-1.8) | — |
| Change from Screening to Week 8 | −0.79 ± 1.85 (14)<br>−1 (−3-3)<br>p = 0.152‡ | −1.79 ± 2.04 (14)<br>−2 (−5-2)<br>p = 0.013‡ | −0.50 ± 2.24 (14)<br>−1 (−5-4)<br>p = 0.393‡ | 0.241$^\square$ |
| | | Total Bilirubin (μmol/L) | | |
| Screening | 9.4 ± 2.7 (14)<br>9 (6-15) | 10.2 ± 3.0 (14)<br>9.5 (7-19) | 10.9 ± 3.5 (14)<br>11 (6-18) | — |
| Visit 3 (Week 8) | 10.4 ± 4.3 (14)<br>9 (5-23) | 8.8 ± 2.4 (14)<br>8 (7-15) | 11.4 ± 3.3 (14)<br>11.5 (7-18) | — |
| Change from Screening to Week 8 | 1.0 ± 4.1 (14)<br>0.5 (−3-14)<br>p = 0.671‡ | −1.4 ± 3.8 (14)<br>−0.5 (−12-4)<br>p = 0.219‡ | 0.5 ± 3.2 (14)<br>1 (−3-7)<br>p = 0.776‡ | 0.315$^\square$ |
| | | Aspartate Transminase (U/L) | | |
| Screening | 24.3 ± 4.5 (14)<br>24 (16-34) | 23.0 ± 3.6 (14)<br>22 (18-29) | 26.1 ± 5.5 (14)<br>27 (17-33) | — |
| Visit 3 (Week 8) | 24.3 ± 3.8 (14)<br>24 (18-31) | 27.1 ± 7.4 (14)<br>25 (20-48) | 26.5 ± 10.1 (13)<br>24 (17-57) | — |
| Change from Screening to Week 8 | 0.0 ± 4.1 (14)$^a$<br>0.5 (−11-6)<br>p = 0.506‡ | 4.1 ± 6.7 (14)$^b$<br>2.5 (−4-23)<br>p = 0.033‡ | 0.9 ± 11.2 (13)$^a$<br>−1 (−9-36)<br>p = 0.503‡ | 0.034$^\square$ |
| | | Alanine Transminase (U/L) | | |
| Screening | 24.9 ± 9.8 (14)<br>22.5 (12-47) | 23.1 ± 5.9 (14)<br>22 (15-35) | 25.5 ± 7.7 (14)<br>26 (13-38) | — |
| Visit 3 (Week 8) | 24.3 ± 5.6 (14)<br>25 (15-35) | 25.9 ± 7.3 (14)<br>24.5 (14-41) | 25.0 ± 12.2 (14)<br>22 (14-63) | — |
| Change from Screening to Week 8 | −0.6 ± 7.0 (14)<br>1 (−17-6)<br>p = 0.753‡ | 2.9 ± 6.2 (14)<br>4 (−7-15)<br>p = 0.150‡ | −0.5 ± 14.0 (14)<br>−1.5 (−17-43)<br>p = 0.223‡ | 0.566* |
| | | Gamma-Glutamyltransferase (U/L) | | |
| Screening | 24.3 ± 12.9 (14)<br>19.5 (10-48) | 19.2 ± 10.2 (14)<br>16 (9-50) | 23.5 ± 14.0 (14)<br>19 (9-61) | — |
| Visit 3 (Week 8) | 23.6 ± 10.0 (14)<br>20.5 (9-44) | 20.8 ± 15.9 (14)<br>14 (10-69) | 21.7 ± 14.5 (14)<br>18 (9-58) | — |
| Change from Screening to Week 8 | −0.7 ± 12.9 (14)<br>−2 (−38-16)<br>p = 0.801‡ | 1.6 ± 6.4 (14)<br>0.5 (−5-19)<br>p = 0.779‡ | −1.8 ± 4.6 (14)<br>−2.5 (−7-11)<br>p = 0.074‡ | 0.281$^\square$ |

N, number;
SD, standard deviation;
Min, minimum;
Max, maximum;
g, gram;
L, liter;
fL, femtoliter;
pg, picogram;
mmol, millimoles;
μmol, micromoles;
mL, milliliter;
min, minutes;
m, meters;
U, units;
μg, microgram; nmol, nanomoles.

$^\Delta$Between-group comparisons were made using ANCOVA. Within-group comparisons were made using the paired Student t-test.
*Logarithmic transformation was required to achieve normality.
$^\square$Between-group comparisons were made using the Kruskal Wallis test.
‡Within group were made using the Wilcoxon signed-rank test. Treatment groups with differing letter superscript are significantly different. Probability values P ≤ 0.05 are statistically significant.

A model was run on creatinine concentration with compliance, treatment group and their interaction as covariates. Table 12 reveals that compliance was not related to creatinine concentration.

TABLE 12

Clinical Creatinine Parameters as a Function of Compliance for PP Participants at Screening and Week 8 (N = 39).
Creatinine Concentration (μmol/L)

| | | | | |
|---|---|---|---|---|
| Screening | 71.7 ± 13.8 (14) | 69.5 ± 10.3 (11) | 63.8 ± 7.8 (14) | — |
| | 74 (49-90) | 70 (53-84) | 64.5 (49-77) | |
| Visit 3 | 73.1 ± 13.1 (14) | 69.5 ± 7.6 (11) | 70.7 ± 17.8 (14) | — |
| (Week 8) | 72.5 (53-92) | 68 (53-81) | 70.5 (33-105) | |
| Change from | 1.4 ± 7.7 (14)$^{a,\,b}$ | 0.0 ± 6.1 (11)$^a$ | 6.9 ± 15.5 (14)$^b$ | 0.030$^\square$ |
| Screening to | 1.5 (−21-12) | 0 (−7-15) | 5 (−34-34) | |
| Week 8 | p = 0.161$^\ddagger$ | p = 0.572$^\ddagger$ | p = 0.050$^\ddagger$ | |

The primary endpoint was a composite endpoint of the changes in Lean Body Mass (as assessed by DM scan) and functional muscle strength (as assessed by 6 Minute Walk Test, Lower Body Dynamometry and Upper Body Dynamometry) of subjects administered Sample 2 compared to those administered placebo from baseline to week 8. The composite endpoint was calculated by multiplying the results of each component score (kg lean muscle mass× meters walked×kg resistance lower body×kg resistance upper body) to derive a composite score (expressed in arbitrary units). The percent change in composite score between baseline and week 8 was derived for comparison between Sample 2 and Placebo.

As revealed in FIG. 25 and Table 11, there was a significant absolute change (P=0.008) in the primary composite endpoint [MM (kg)×US (kg)×LS (kg)×6W (m)] for participants taking Sample 2 (n=42, ITT population). This absolute change was significant compared to the placebo group (P=0.016) and approached significance when compared to the Sample 1 group (P=0.077). Notably, when expressed as a percentage, the absolute change in composite endpoints for the Sample 2 group translated into a 63.5 percentage point increase over placebo.

Example No. 2

As described above, in one embodiment, the protein building composition of the present disclosure may be combined with a stabilizer package for improving one or more properties of the composition. The following example provides exemplary formulations, but is not intended to limit the invention. In fact, the stabilizer package and the process for incorporating the stabilizer package into the composition may be used in any suitable pharmaceutical composition and may not be limited solely to the protein building composition of the present disclosure.

In one embodiment, the following components may be first mixed together. The components include a protein building composition in accordance with the present disclosure combined with a polymer binder. In Sample No. 1, the polymer binder is modified starch. In Sample No. 2, the polymer binder is larch arabinogalactan. The below components can be spray dried into a granule to form a granular

TABLE 13

Absolute and Percentage Change in the Composite Endpoint at Baseline and at End of the Study for All Participants in the PP Population (N = 39).

| | Placebo | Sample 1 | Sample 2 | Between Group P Values | | | |
|---|---|---|---|---|---|---|---|
| | Mean ± SD (n) Median (Min-Max) Within Group P Value | Mean ± SD (n) Median (Min-Max) Within Group P Value | Mean ± SD (n) Median (Min-Max) Within Group P Value | Overall$^\Delta$ | Placebo vs Sample 1$^\delta$ | Placebo vs Sample 2$^\delta$ | Sample 1 vs Sample 2$^\delta$ |
| Composite Endpoint (×10$^3$) | | | | | | | |
| Baseline (Week 0) | 11,032 ± 11,501 (14) 7,870 (559-39,977) | 10,921 ± 11,142 (11) 5,997 (1,269-37,560) | 6,313 ± 5,485 (14) 4,466 (677-19,276) | — | — | — | — |
| Visit 3 (Week 8) | 7,611 ± 4,893 (14) 6,334 (360-16,803) | 10,620 ± 11,893 (11) 6,734 (1,404-42,706) | 8,367 ± 7,025 (14) 6,475 (1,135-26,858) | — | — | — | — |
| Change from Baseline to Week 8 | −3,421 ± 8,073 (14)$^a$ −1,231 (−26,672-4,814) p = 0.232* | −301 ± 3,467 (11)$^{a,b}$ −374 (−8,681-5,146) p = 0.534* | 2,054 ± 2,359 (14)$^b$ 858 (−406-7,582) p = 0.008* | 0.022* | 0.826* | 0.021* | 0.113* |

N, number;
SD, standard deviation;
Min, minimum;
Max, maximum;
BMI, body mass index;
kg, kilogram;
m, meter;
cm, centimeter
$^\Delta$Between-group comparisons were made using ANCOVA.
$^\delta$Pairwise between-group comparisons were made using the Tukey procedure.
Within-group comparisons were made using the paired Student t-test.
*Logarithmic transformation was required to achieve normality.
$^\square$Between-group comparisons were made using the Kruskal Wallis test.
$^\ddagger$Within-group comparisons were made using the signed-rank test.
Treatment groups with differing letter superscripts are significantly different.
Probability values P ≤ 0.05 are statistically significant.

product. For instance, the spray pressure can be about 2 bar while the spray rate can be from about 10 to about 20 grams per minute.

|  | Sample No. 1 | | | | Sample No. 2 | | | |
| --- | --- | --- | --- | --- | --- | --- | --- | --- |
|  | Quant. g | Assay % | (dry) Product g | (incl. moisture) Product % | Quant. g | Assay % | (dry) Product g | (incl. moisture) Product % |
| Water | 1900 | 0.0% | 5 | 0.50% | 1700 | 0.0% | 5 | 0.50% |
| L-Carnitine | 185 | 99.9% | 185 | 18.46% | 185 | 99.9% | 185 | 18.46% |
| Creatine monohydrate | 420 | 87.9% | 369 | 36.92% | 420 | 87.9% | 369 | 36.92% |
| L-Leucine | 246 | 100.0% | 246 | 24.62% | 246 | 100.0% | 246 | 24.62% |
| vitamin D3 | 0.10 | 100.0% | 0 | 0.01% | 0.10 | 100.0% | 0 | 0.01% |
| Sodium stearate/citric acid esters/rapeseed lecithin | 10 | 100.0% | 10 | 1.00% | 20 | 100.0% | 20 | 2.00% |
| Modified Starch | 195 | 95.0% | 185 | 18.50% | 0 | 95.0% | 0 | 0.00% |
| Larch arabinogalactan | 0 | 94.7% | 0 | 0.00% | 195 | 94.7% | 185 | 18.50% |
|  | 0 | 100.0% | 0 | 0.00% | 0 | 100.0% | 0 | 0.00% |
| Isolated product [g] | 560.00 | 1'400.00 | 800 |  | 2'000.00 |  |  |  |
| Properties (granulate, agglom.) | granulate | granulate | granulate |  | granulate |  |  |  |
| Particlesize d10 [μm] | 204.59 | 235.73 | 136.86 |  | 235.96 |  |  |  |
| Particlesize d50 [μm] | 300.39 | 331.22 | 226.10 |  | 262.65 |  |  |  |
| Particlesize d90 [μm] | 450.04 | 472.33 | 411.51 |  | 363.10 |  |  |  |
| Bulk density [kg/L] | 0.56 | 0.52 | 0.58 |  | 0.68 |  |  |  |
| Moisture [%] (100° C./25 min) | 2.30 | 2.18 | 4.28 |  | 3.90 |  |  |  |
| Moisture [%] (KFT) | 0.93 | 0.86 | 1.88 |  | 2.55 |  |  |  |

After the above granular product is produced, the product can be mixed with a stabilizer package. The stabilizer package may comprise a dry mix of calcium stearate and silica. The calcium stearate can be added in an amount of about 2.5% by weight, while the silica may be added in an amount of about 0.2% by weight. Because the stabilizer package is a dry mix, a pharmaceutical composition is produced that comprises a granular mixture. The stearate and silica serve to stabilize the granular particles.

To the granular mixture, a fat coating material can be applied. The fat coating material may comprise a combination of hydrogenated palm oil and palm stearine. In one embodiment, hydrogenated palm oil is added in an amount of 16% by weight, while palm stearine is added in an amount of 4% by weight of the resulting pharmaceutical composition. In an alternative embodiment, the hydrogenated palm oil is added in an amount of 24% by weight, while the palm stearine is added in an amount of 6% by weight of the pharmaceutical composition.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A method for preserving muscle mass and function by increasing skeletal muscle protein synthesis and/or decreasing skeletal muscle protein degradation in healthy mammals, the method comprising administering to the healthy mammal a protein building composition, said protein building composition comprising an amino acid derivative, wherein the amino acid derivative is L-carnitine, derivatives of L-carnitine, and/or salts thereof, combined with an amino acid component, wherein the amino acid component is Leucine, metabolites of Leucine, and/or salts thereof, and a nitrogenous organic acid, wherein the nitrogenous organic acid is Creatine, derivatives and/or analogs of Creatine, or salts thereof;

wherein the protein building composition is administered in an amount sufficient to increase skeletal muscle protein synthesis, increase functional strength, or increase both skeletal muscle protein synthesis and functional strength, without requiring the healthy mammal to participate in physical activity; and wherein the nitrogenous organic acid is present in the protein building composition at a concentration of about 30% to about 80% by mass based on the mass of the amino acid derivative, amino acid component, and nitrogenous organic acid, and the amino acid component is present in the protein building composition at a concentration of about 20% to 30.8% by mass based on the mass of the amino acid derivative, amino acid component, and nitrogenous organic acid.

2. A method as defined in claim 1, wherein the nitrogenous organic acid comprises magnesium chelated creatine.

3. A method as defined in claim 1, wherein the protein building composition further comprises magnesium or salts thereof.

4. A method as defined in claim 1, wherein the protein building composition further comprises vitamin D.

5. A method as defined in claim 1, wherein the healthy mammal that is administered the protein building composition has an age of more than about 50% of its expected life span.

6. A method as defined in claim 1, wherein the protein building composition is contained in a food product or beverage.

7. A method as defined in claim 1, wherein the protein building composition is administered at least every one to three days.

8. A method as defined in claim 1, wherein the protein building composition is administered for at least 50 consecutive days.

9. A method as defined in claim 1, wherein the protein building composition is administered one to four times a day.

10. A method as defined in claim 1, wherein the amino acid derivative is L-carnitine, wherein the L-carnitine is administered to the healthy mammal in an amount from 50 milligrams to 5,000 milligrams per dose.

11. A method as defined in claim 1, wherein the amino acid component is leucine, wherein the leucine is administered to the healthy mammal in an amount from 50 milligrams to 5,000 milligrams per dose.

12. A method as defined in claim 1, wherein the healthy mammal is a human.

13. A method as defined in claim 1, wherein the healthy mammal is sedentary.

14. A method as defined in claim 1, wherein the amino acid derivative is L-carnitine, wherein the L-carnitine is administered to the healthy mammal in an amount from 100 milligrams to 3,000 milligrams per dose.

15. A method as defined in claim 1, wherein the amino acid component is leucine, wherein the leucine is administered to the healthy mammal in an amount from 100 milligrams to 4,000 milligrams per dose.

16. A method as defined in claim 1, wherein the protein building composition contains the nitrogenous organic acid which comprises creatine, wherein the creatine is administered to the healthy mammal in an amount from 5 milligrams to 20,000 milligrams per dose.

17. A method as defined in claim 1, wherein the protein building composition is administered to the healthy mammal in an amount sufficient to increase lean muscle mass in the healthy mammal.

18. A method as defined in claim 1, wherein the protein building composition is administered to the healthy mammal in an amount sufficient to treat or prevent sarcopenia.

19. A method as defined in claim 1, wherein the protein building composition is administered to the healthy mammal in an amount sufficient to decrease the amount of TNF-α in the muscles.

20. A method as defined in claim 1, wherein the protein building composition is administered to the healthy mammal in an amount sufficient to increase mTOR expression in the muscles.

21. A method as defined in claim 1, wherein mTOR expression is increased by greater than 40% after activity in comparison to the same healthy mammal that has not received the protein building composition.

22. The method of claim 1, wherein the amino acid derivative is present in the protein building composition at a concentration of about 15% to about 30% by mass based on the mass of the amino acid derivative, amino acid component, and nitrogenous organic acid.

23. The method of claim 1, wherein the nitrogenous organic acid is creatine, wherein the creatine is administered to the healthy mammal in an amount from 50 milligrams to 10,000 milligrams per dose.

24. A method for preserving muscle mass and function by increasing skeletal muscle protein synthesis and/or decreasing skeletal muscle protein degradation in healthy mammals, the method comprising administering to the healthy mammal a protein building composition, said protein building composition consisting of:

an amino acid derivative, wherein the amino acid derivative is L-carnitine, derivatives of L-carnitine, and/or salts thereof, combined with an amino acid component, wherein the amino acid component is Leucine, metabolites of Leucine, and/or salts thereof, and a nitrogenous organic acid, wherein the nitrogenous organic acid is Creatine, derivatives and/or analogs of Creatine, or salts thereof, and optionally vitamin D and/or at least one excipient.

25. The method of claim 24, wherein the at least one excipient comprises an antiadherent, a binder, a synthetic polymer, a coating, a coloring agent, a disintegrant, a filler, a flavoring agent, a glidant, a lubricant, a preservative, a sorbent, a sweetener, a vehicle, or combinations thereof.

26. The method of claim 24, wherein the amino acid derivative is present in an amount of 10-40% by mass, the amino acid compound is present in an amount of 10-40% by mass, and the nitrogenous organic acid is present in an amount of 30-80% by mass, based on the mass of the amino acid derivative, amino acid component, and nitrogenous organic acid.

27. The method of claim 24, wherein the amino acid derivative is administered to the healthy mammal in an amount from 100 milligrams to 3,000 milligrams per dose, the amino acid component is administered to the healthy mammal in an amount from 50 milligrams to 3,000 milligrams per dose, and the nitrogenous organic acid is administered to the healthy mammal in an amount from 50 milligrams to 5,000 milligrams per dose.

\* \* \* \* \*